United States Patent
Cihlar

(10) Patent No.: US 11,491,169 B2
(45) Date of Patent: *Nov. 8, 2022

(54) REMDESIVIR TREATMENT METHODS

(71) Applicant: Gilead Sciences, Inc., Foster City, CA (US)

(72) Inventor: Tomas Cihlar, Burlingame, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/676,920

(22) Filed: Feb. 22, 2022

(65) Prior Publication Data

US 2022/0175805 A1    Jun. 9, 2022

Related U.S. Application Data

(63) Continuation of application No. 17/333,389, filed on May 28, 2021.

(60) Provisional application No. 63/032,321, filed on May 29, 2020.

(51) Int. Cl.
*A61K 31/675* (2006.01)
*A61P 31/14* (2006.01)

(52) U.S. Cl.
CPC .......... *A61K 31/675* (2013.01); *A61P 31/14* (2018.01)

(58) Field of Classification Search
CPC .............................. A61K 31/675; A61P 31/14
See application file for complete search history.

(56) References Cited

U.S. PATENT DOCUMENTS

| | | | |
|---|---|---|---|
| 4,816,570 A | 3/1989 | Farquhar | |
| 4,968,788 A | 11/1990 | Farquhar | |
| 5,663,159 A | 9/1997 | Starrett, Jr. et al. | |
| 5,792,756 A | 8/1998 | Starrett, Jr. et al. | |
| 6,312,662 B1 | 11/2001 | Erion et al. | |
| 6,475,985 B1 | 11/2002 | Wagner et al. | |
| 6,476,030 B1 | 11/2002 | Carling et al. | |
| 6,656,915 B1 | 12/2003 | Bantia et al. | |
| 6,909,011 B2 | 6/2005 | Skranc et al. | |
| 7,078,403 B1 | 7/2006 | Wu et al. | |
| 7,105,493 B2 | 9/2006 | Sommadossi et al. | |
| 7,125,855 B2 | 10/2006 | Bhat et al. | |
| 7,166,604 B2 | 1/2007 | Watson et al. | |
| 7,176,203 B2 | 2/2007 | Chambers et al. | |
| 7,268,119 B2 | 9/2007 | Cook et al. | |
| 7,285,658 B2 | 10/2007 | Cook et al. | |
| 7,368,437 B1 | 5/2008 | Bojack et al. | |
| 7,390,791 B2 | 6/2008 | Becker et al. | |
| 7,429,571 B2 | 9/2008 | Chand et al. | |
| 7,514,410 B2 | 4/2009 | Babu et al. | |
| 7,560,434 B2 | 7/2009 | Babu et al. | |
| 7,598,230 B2 | 10/2009 | Cook et al. | |
| 7,608,597 B2 | 10/2009 | Sommadossi et al. | |
| 7,713,941 B2 | 5/2010 | Cook et al. | |
| 7,803,788 B2 | 9/2010 | Becker et al. | |
| 7,807,653 B2 | 10/2010 | Cook et al. | |
| 7,842,672 B2 | 11/2010 | Boojamra et al. | |
| 7,951,787 B2 | 5/2011 | McGuigan | |
| 7,973,013 B2 | 7/2011 | Cho et al. | |
| 7,994,139 B2 | 8/2011 | Babu et al. | |
| 8,008,264 B2 | 8/2011 | Butler et al. | |
| 8,012,941 B2 | 9/2011 | Cho et al. | |
| 8,012,942 B2 | 9/2011 | Butler et al. | |
| 8,071,568 B2 | 12/2011 | Narjes et al. | |
| 8,119,607 B2 | 2/2012 | Francom et al. | |
| 8,242,085 B2 | 8/2012 | Babu et al. | |
| 8,318,682 B2 | 11/2012 | Butler et al. | |
| 8,415,308 B2 | 4/2013 | Cho et al. | |
| 8,455,451 B2 | 6/2013 | Cho et al. | |
| 8,853,171 B2 | 10/2014 | Butler et al. | |
| 8,871,737 B2 | 10/2014 | Smith et al. | |
| 8,889,159 B2 | 11/2014 | Clearly et al. | |
| 8,980,865 B2 | 3/2015 | Wang | |
| 9,090,642 B2 | 7/2015 | Cho et al. | |
| 9,243,022 B2 | 1/2016 | Beigelman et al. | |
| 9,249,174 B2 | 2/2016 | Beigelman et al. | |
| 9,278,990 B2 | 3/2016 | Smith et al. | |
| 9,388,208 B2 | 7/2016 | Clarke et al. | |
| 9,393,256 B2 | 7/2016 | Ray et al. | |
| 9,452,154 B2 | 9/2016 | Delaney et al. | |
| 9,481,703 B2 | 11/2016 | Kalayanov et al. | |
| 9,487,544 B2 | 11/2016 | Cho et al. | |
| 9,504,701 B2 | 11/2016 | Casola et al. | |
| 9,540,411 B2 | 1/2017 | Kalayanov et al. | |
| 9,549,941 B2 | 1/2017 | Cleary et al. | |
| 9,605,018 B2 | 3/2017 | Wang et al. | |

(Continued)

FOREIGN PATENT DOCUMENTS

| | | |
|---|---|---|
| CN | 111171078 | 5/2020 |
| CN | 111265532 | 6/2020 |

(Continued)

OTHER PUBLICATIONS

Agostini et al., "Coronavirus Susceptibility to the Antiviral Remdesivir (GS5734) Is Mediated by the Viral Polymerase and the Proofreading Exoribonuclease", MBIO, Mar. 6, 2018, 9(2):1-15.

Alessandrini, et al., Synthesis of Differently Protected 1-C-methyl-ribofuranoses Intermediates for the Preparation of Biologically Active 1'-C-methyl-ribonucleosides, Journal of Carbohydrate Chemistry, 2008, pp. 332-344, vol. 27, No. 5.

Ali, et al., Quantitative structure-activity relationships (QSAR) of two series of O-aryl or N-acyl O-ethyl phosphoramidate and phosphorodiamidate fungicides incorporating amino acid ethyl esters, Bulletin of Environmental Contamination and Toxicology, 2000, pp. 415-420, vol. 65, No. 4.

(Continued)

*Primary Examiner* — Kamal A Saeed
(74) *Attorney, Agent, or Firm* — Fish & Richardson P.C.

(57) ABSTRACT

Provided herein are methods of treating or preventing a viral infection in a subject comprising administering a compound of Formula I, Formula Ia, or Formula Ib, or a pharmaceutically acceptable salt thereof, wherein the subject is not being treated with chloroquine, or an analog or salt thereof.

24 Claims, 4 Drawing Sheets

(56) References Cited

U.S. PATENT DOCUMENTS

| | | |
|---|---|---|
| 9,616,076 B2 | 4/2017 | Casola et al. |
| 9,701,682 B2 | 7/2017 | Clarke et al. |
| 9,724,360 B2 | 8/2017 | Chun et al. |
| 9,828,408 B2 | 11/2017 | Kalayanov |
| RE46,762 E | 3/2018 | Butler et al. |
| 9,949,994 B2 | 4/2018 | Chun et al. |
| 10,023,600 B2 | 7/2018 | Butler et al. |
| 10,034,893 B2 | 7/2018 | Luly et al. |
| 10,059,716 B2 | 8/2018 | Clarke et al. |
| 10,065,958 B2 | 9/2018 | Mackman et al. |
| 10,251,898 B2 | 4/2019 | Chun et al. |
| 10,251,904 B2 | 4/2019 | Clarke et al. |
| 10,377,761 B2 | 8/2019 | Clarke et al. |
| RE47,589 E | 9/2019 | McGuigan |
| 10,675,296 B2 | 6/2020 | Larson |
| 10,682,368 B2 | 6/2020 | Perron et al. |
| 10,695,357 B2 | 6/2020 | Chun et al. |
| 10,695,361 B2 | 6/2020 | Clarke et al. |
| 10,696,679 B2 | 6/2020 | Mackman et al. |
| 10,836,787 B2 | 11/2020 | Brak et al. |
| 10,988,498 B2 | 4/2021 | Butler et al. |
| 11,007,208 B2 | 5/2021 | Clarke et al. |
| 11,260,070 B2 | 3/2022 | Perron et al. |
| 11,266,666 B2 | 3/2022 | Chun et al. |
| 11,266,681 B2 | 3/2022 | Larson et al. |
| 11,344,565 B2 | 5/2022 | Axt et al. |
| 11,382,926 B2 | 7/2022 | Clarke et al. |
| 2003/0050229 A1 | 3/2003 | Sommadossi et al. |
| 2003/0092775 A1 | 5/2003 | Ernst et al. |
| 2004/0006002 A1 | 1/2004 | Sommadossi et al. |
| 2004/0023901 A1 | 2/2004 | Cook et al. |
| 2004/0063658 A1 | 4/2004 | Roberts et al. |
| 2004/0067901 A1 | 4/2004 | Bhat et al. |
| 2004/0138170 A1 | 7/2004 | Montgomery et al. |
| 2005/0187180 A1 | 8/2005 | Loeb et al. |
| 2005/0209166 A1 | 9/2005 | Eckhardt et al. |
| 2005/0215513 A1 | 9/2005 | Boojamra et al. |
| 2005/0250728 A1 | 11/2005 | Bantia et al. |
| 2006/0058303 A1 | 3/2006 | Chambers et al. |
| 2006/0142238 A1 | 6/2006 | McGuigan |
| 2006/0241064 A1 | 10/2006 | Roberts et al. |
| 2008/0107628 A1 | 5/2008 | Boojamra et al. |
| 2008/0161324 A1 | 7/2008 | Johansen et al. |
| 2008/0280842 A1 | 11/2008 | MacCoss et al. |
| 2009/0004138 A1 | 1/2009 | Francom et al. |
| 2009/0221524 A1 | 9/2009 | Kotra et al. |
| 2009/0233879 A1 | 9/2009 | Reddy et al. |
| 2009/0317361 A1 | 12/2009 | Cho et al. |
| 2010/0015094 A1 | 1/2010 | Babu et al. |
| 2010/0016251 A1 | 1/2010 | Sofia et al. |
| 2010/0021425 A1 | 1/2010 | Butler et al. |
| 2010/0035835 A1 | 2/2010 | Narjes et al. |
| 2010/0035836 A1 | 2/2010 | Francom et al. |
| 2010/0065512 A1 | 3/2010 | Bjorsvik |
| 2010/0203015 A1 | 8/2010 | Butler et al. |
| 2010/0234584 A1 | 9/2010 | Chang |
| 2010/0249068 A1 | 9/2010 | Beigelman et al. |
| 2010/0291031 A2 | 11/2010 | Francom et al. |
| 2010/0298257 A1 | 11/2010 | Ross et al. |
| 2010/0305202 A1 | 12/2010 | Hwang et al. |
| 2011/0070194 A1 | 3/2011 | Cho et al. |
| 2011/0084230 A1 | 4/2011 | Knochel et al. |
| 2011/0230654 A1 | 9/2011 | Butler et al. |
| 2011/0257122 A1 | 10/2011 | Sofia et al. |
| 2011/0293563 A1 | 12/2011 | Butler et al. |
| 2012/0009147 A1 | 1/2012 | Cho et al. |
| 2012/0020921 A1 | 1/2012 | Cho et al. |
| 2012/0027752 A1 | 2/2012 | Mackman et al. |
| 2012/0071434 A1 | 3/2012 | Smith et al. |
| 2012/0107274 A1 | 5/2012 | Clarke et al. |
| 2013/0034521 A1 | 2/2013 | Butler et al. |
| 2013/0143835 A1 | 6/2013 | Eneroth et al. |
| 2013/0281686 A1 | 10/2013 | Cho et al. |
| 2013/0315868 A1 | 11/2013 | Mayes |
| 2013/0344028 A2 | 12/2013 | Butler et al. |
| 2014/0219958 A1 | 8/2014 | Luly et al. |
| 2015/0031687 A1 | 1/2015 | Guo et al. |
| 2015/0111839 A1 | 4/2015 | Mackman et al. |
| 2015/0133395 A1 | 5/2015 | Clarke et al. |
| 2015/0152116 A1 | 6/2015 | Mackman et al. |
| 2015/0210682 A1 | 7/2015 | Han et al. |
| 2015/0252057 A1 | 9/2015 | Guo et al. |
| 2016/0058779 A1 | 3/2016 | Casola et al. |
| 2016/0122344 A1 | 5/2016 | Han et al. |
| 2016/0122356 A1 | 5/2016 | Axt et al. |
| 2016/0122374 A1 | 5/2016 | Chun |
| 2016/0176899 A1 | 6/2016 | Schwitter et al. |
| 2016/0220586 A1 | 8/2016 | Andre et al. |
| 2016/0237090 A1 | 8/2016 | Hu et al. |
| 2017/0071964 A1 | 3/2017 | Clark et al. |
| 2018/0346504 A1 | 12/2018 | Brak et al. |
| 2019/0083525 A1 | 3/2019 | Larson |
| 2020/0197422 A1 | 6/2020 | Axt et al. |
| 2020/0360420 A1 | 11/2020 | Larson |
| 2020/0376014 A1 | 12/2020 | Perron et al. |
| 2021/0052613 A1 | 2/2021 | Chun et al. |
| 2021/0061806 A1 | 3/2021 | Mackman et al. |
| 2021/0283150 A1 | 9/2021 | Cihlar et al. |
| 2021/0309689 A1 | 10/2021 | Badalov et al. |
| 2021/0330685 A1 | 10/2021 | Ellis et al. |
| 2021/0393653 A1 | 12/2021 | Cihlar et al. |
| 2021/0393659 A1 | 12/2021 | O'Neil et al. |
| 2021/0403497 A1 | 12/2021 | Butler et al. |
| 2022/0081462 A1 | 3/2022 | Chun et al. |

FOREIGN PATENT DOCUMENTS

| | | |
|---|---|---|
| CN | 113185519 | 7/2021 |
| WO | WO1991019721 | 12/1991 |
| WO | WO1999045029 | 9/1999 |
| WO | WO2000056734 | 9/2000 |
| WO | WO2000075157 | 12/2000 |
| WO | WO2001032153 | 5/2001 |
| WO | WO2001060315 | 8/2001 |
| WO | WO2001090121 | 11/2001 |
| WO | WO2002008241 | 1/2002 |
| WO | WO2002018404 | 3/2002 |
| WO | WO2002032920 | 4/2002 |
| WO | WO2002057287 | 7/2002 |
| WO | WO2002057425 | 7/2002 |
| WO | WO2003093272 | 11/2003 |
| WO | WO2003093273 | 11/2003 |
| WO | WO2003100009 | 12/2003 |
| WO | WO2004046331 | 6/2004 |
| WO | WO2004112687 | 12/2004 |
| WO | WO2005009418 | 2/2005 |
| WO | WO2005092877 | 10/2005 |
| WO | WO2005123087 | 12/2005 |
| WO | WO2006031725 | 3/2006 |
| WO | WO2006050161 | 5/2006 |
| WO | WO2006064033 | 6/2006 |
| WO | WO2006065335 | 6/2006 |
| WO | WO2006121820 | 11/2006 |
| WO | WO2006135978 | 12/2006 |
| WO | WO2007027248 | 3/2007 |
| WO | WO2007056170 | 5/2007 |
| WO | WO2007062542 | 6/2007 |
| WO | WO2007064883 | 6/2007 |
| WO | WO2007064931 | 6/2007 |
| WO | WO2007065289 | 6/2007 |
| WO | WO2007065829 | 6/2007 |
| WO | WO2007095269 | 8/2007 |
| WO | WO2007097991 | 8/2007 |
| WO | WO2007113294 | 10/2007 |
| WO | WO2007135134 | 11/2007 |
| WO | WO2008005542 | 1/2008 |
| WO | WO2008055870 | 5/2008 |
| WO | WO2008079206 | 7/2008 |
| WO | WO2008082601 | 7/2008 |
| WO | WO2008085508 | 7/2008 |
| WO | WO2008089105 | 7/2008 |
| WO | WO2008116064 | 9/2008 |
| WO | WO2008121634 | 10/2008 |
| WO | WO2008141079 | 11/2008 |

(56) References Cited

FOREIGN PATENT DOCUMENTS

| | | |
|---|---|---|
| WO | WO2009009951 | 1/2009 |
| WO | WO2009018609 | 2/2009 |
| WO | WO2009131926 | 10/2009 |
| WO | WO2009132123 | 10/2009 |
| WO | WO2009132135 | 10/2009 |
| WO | WO2010002877 | 1/2010 |
| WO | WO2010036407 | 4/2010 |
| WO | WO2010093608 | 8/2010 |
| WO | WO2010099458 | 9/2010 |
| WO | WO2010135569 | 11/2010 |
| WO | WO2011011303 | 1/2011 |
| WO | WO2010111381 | 3/2011 |
| WO | WO2011035231 | 3/2011 |
| WO | WO2011035250 | 3/2011 |
| WO | WO2011080568 | 7/2011 |
| WO | WO2011123645 | 10/2011 |
| WO | WO2011123668 | 10/2011 |
| WO | WO2011123672 | 10/2011 |
| WO | WO2011150288 | 12/2011 |
| WO | WO2012012465 | 1/2012 |
| WO | WO2012012776 | 1/2012 |
| WO | WO2012039787 | 3/2012 |
| WO | WO2012039791 | 3/2012 |
| WO | WO2012051570 | 4/2012 |
| WO | WO2012040127 | 5/2012 |
| WO | WO2012121764 | 9/2012 |
| WO | WO2012142523 | 10/2012 |
| WO | WO2012158643 | 11/2012 |
| WO | WO2013084165 | 6/2013 |
| WO | WO2014033617 | 3/2014 |
| WO | WO2014042433 | 3/2014 |
| WO | WO2014078463 | 5/2014 |
| WO | WO2014078778 | 5/2014 |
| WO | WO2014116755 | 7/2014 |
| WO | WO2014169280 | 10/2014 |
| WO | WO2016107833 | 12/2014 |
| WO | WO2015069939 | 5/2015 |
| WO | WO2015173164 | 11/2015 |
| WO | WO2016012470 | 1/2016 |
| WO | WO2016023877 | 2/2016 |
| WO | WO2016069825 | 5/2016 |
| WO | WO2016069826 | 5/2016 |
| WO | WO2016069827 | 5/2016 |
| WO | WO2016102438 | 6/2016 |
| WO | WO2016107832 | 7/2016 |
| WO | WO2016120186 | 8/2016 |
| WO | WO2016128335 | 8/2016 |
| WO | WO2017184668 | 10/2017 |
| WO | WO2018085307 | 5/2018 |
| WO | WO2018121678 | 7/2018 |
| WO | WO2018145148 | 8/2018 |
| WO | WO2018204198 | 11/2018 |
| WO | WO2019014247 | 1/2019 |
| WO | WO2019053696 | 3/2019 |
| WO | WO2021021717 | 2/2021 |
| WO | WO2021050961 | 3/2021 |
| WO | WO2021147236 | 7/2021 |
| WO | WO2021202907 | 10/2021 |
| WO | WO2021207049 | 10/2021 |
| WO | WO2021213288 | 10/2021 |
| WO | WO2022047065 | 3/2022 |

OTHER PUBLICATIONS

Anonymous, "Gillings research on broad-spectrum antiviral could aid public health response to coronavirus outbreaks", —UNC Gillings School of Global Public Health, Jan. 10, 2020, retrieved on May 13, 2021, retrieved from URL <"https://sph.unc.edu/sph-news/gillings-research-on-broad-spectrum-antiviral-could-aid-public-health-response-to-coronavirus-outbreaks/">, 5 pages.
Arimilli, et al., Synthesis, In Vitro Biological Evaluation and Oral Bioavailability of 9-[2-(phosphonomethoxy)propyl]adenine (PMPA) Prodrugs, Antiviral Chemistry & Chemotherapy, 1997, pp. 557-564, vol. 8, No. 6.
Asbun, et al., Synthesis of 5-substituted Pyrimidines. II, Journal of Organic Chemistry, 1968, pp. 140-142, vol. 31.
Ballini, et al., Enantioselective Synthesis of the Lactone Moiety of the Mevinic Acids using D-Xylose as a Chiral Precursor, Journal of the Chemical Society, Perkin Transactions 1, 1991, pp. 490-491.
Balzarini, et al., Inhibition of Feline (FIPV) and Human (SARS) Coronavirus by Semisynthetic Derivatives of Glycopeptide Antibiotics, Antiviral Research, 2006, pp. 20-33, vol. 72.
Bandini, et al., Indium tribromide: a highly effective catalyst for the addition of trimethylsilyl cyanide to α-hetero-substituted ketone, Tetrahedron Letters, 2001, pp. 3041-3043. vol. 42.
Barker, et al., 2,3,5-Tri-O-benzyl-D-ribosyl and -L-arabinosyl Bromides, Journal of Organic Chemistry, 1961, pp. 4605-4609, vol. 26, No. 11.
Barl, et al., The halogen/magnesium-exchange using iPrMgCl•LiCl and related exchange reagents, Heterocycles, Jan. 2014, pp. 827-844, vol. 88, No. 2.
Beer et al., "Characteristics of Filoviridae: Marburg and Ebola Viruses," Naturwissenschaften, 1999, 86:8-17.
Behzadi et al., "Overview of Current Therapeutics and Novel Candidates Against Influenza Respiratory Syncytial Virus, and Middle East Respiratory Syndrome Coronavirus Infections," Frontiers in Microbiology, Jun. 2019, 10:1327, pp. 1-16000.
Belokon et al., "Optimized catalysts for the asymmetric addition of trimethylsilyl cyanide to aldehydes and ketones," Tetrahedron, 2001, 57: 771-779.
Benksim et al., "A Novel Stereospecific Synthesis of Glycosyl Cyanides from 1,2-O-sulfinyl Derivatives," Organic Letters, 2004, 6(22): 3913-3915.
Benzaria et al., "Synthesis, In Vitro Antiviral Evaluation, and Stability Studies of Bis(S-acyl-2-thioethyl) Ester Derivatives of 9-[2-(phosphonomethoxy)ethyl]adenine (PMEA) as Potential PMEA prodrugs with Improved Oral Bioavailability," J. Med. Chem., 1996, 39(25): 4958-4965.
Bio et al., "Practical Synthesis of a Potent Hepatitis C Virus RNA Replication Inhibitor," J. Org. Chem., 2004, 69(19): 6257-6266.
Bobeck et al., "Advances in Nucleoside Monophosphate Prodrugs as Anti-HCV Agents," Antiviral Therapy, 2010, 15: 935-950.
Bobrowski et al., "Synergistic and Antagonistic Drug Combinations against SARS-CoV-2", Molecular Therapy, Feb. 2021, 29(2):873-885.
Bojack, et al., Design and Synthesis of Inhibitors of Adenosine and AMP Deaminases, Organic Letters, 2001, pp. 839-842, vol. 3, No. 6.
Bowie et al., "RIG-I: tri-ing to discriminate between self and non-self RNA," Trends in Immunology, Apr. 2007, 28(4): 147-150.
Boyer, et al., Pathogenesis, diagnosis and management of hepatitis C, Journal of Hepatology, 2000, pp. 98-112, vol. 32.
Bozza, Zika Outbreak, Brazil 2015, ISARIC, 2015, 28 pages.
Bradley et al., "The Management of Community-Acquired Pneumonia in Infants and Children Older Than 3 Months of Age: Clinical Practice Guidelines by the Pediatric Infectious Diseases Society and the Infectious Diseases Society of America", Pediatric Community Pneumonia Guidelines, Clinical Infectious Diseases, Oct. 2011, 53(7):e25-e76.
Brands et al., "Crystallization-Induced Diastereomer Transformations," Chem. Rev., 2006, 106(7): 2711-2733.
Brittain, Polymorphism in Pharmaceutical Solids, 2nd Edition, 2009, pp. 183-226, Informa Healthcare USA, Inc.
Brotschi et al., "Bipyridyl and biphenyl DNA: A recognition motif based on interstrand aromatic stacking," Chemistry—A European Journal, 2005, 11(6):1911-1923.
Brown et al., "Broad spectmm antiviral remdesivir inhibits human endemic and zoonotic deltacoronavimses with a highly divergent RNA dependent RNA polymerase", Antiviral Research, Jun. 21, 2019, 169:1-31.
Brown, "Progress towards improving antiviral therapy for hepatitis C virus polymerase inhibitors", Part O: Nucleoside analogues, 2009, 18: 709-725.
Bullard-Feibelman et al., "The FDA-approved drug Sofosbuvir inhibits Zika Virus infection," Antiviral Res., Jan. 1, 2018, 137: 134-140.

(56) References Cited

OTHER PUBLICATIONS

Burns, "A Glimmer of Hope for Fatal Feline Disease," JAVMAnews, Dec. 15, 2017, 5 pages.
Butora et al., "Synthesis and HCV inhibitory properties of 9-deaza- and 7,9-dideaza-7-oxa-2'-C-methyladenosine," Bioorganic & Medicinal Chemistry, 2007, 15(15): 5219-5229.
Cabirol et al., Robust and Efficient, yet Uncatalyzed, Synthesis of Triarylsilyl-protected Cyanohydrins from Ketones, 2008, pp. 2446-2449, vol. 73.
Caira, "Crystalline Polymorphism of Organic Compounds," Topics in Current Chemistry, 1998, 198: 163-208.
Cales et al., "Treatment of liver fibrosis: clinical aspects," Gastroentérologie Clinique et Biologique, 2009, 33(10-11): 958-966.
Calisher et al., "Antigenic Relationships between Flaviviruses as Determined by Cross-neutralization Tests with Polyclonal Antisera," Journal of General Virology, 1989, 70: 37-43.
Camps, "Studies on Structurally Simple -αβ-butenolides-II," Tetrahedron, 1982, 38(15): 2395-2402.
Carey et al., "Addition, Condensation and Substitution Reactions of Carbonyl Compounds," Advanced Organic Chemistry: Part B: Reaction and Synthesis, Springer Science & Business Media, 2007, pp. 629-711.
Carroll, "Robust Antiviral Efficacy upon Administration of a Nucleoside Analog to Hepatitis C Virus-Infected Chimpanzees," Antimicrobial Agents and Chemotherapy, 2009, 53(3): 926-934.
Carryer et al., "The effect of cortisone on bronchial asthma and hay fever occurring in subjects sensitive to ragweed pollen", Journal of Allergy, Jul. 1950, 21(4): 282-287.
CAS No. 1476-52-4, "Desethyl Chloroquine", ChemSRc, retrieved on Jul. 29, 2021, retrieved from URL <"https://www.chemsrc.com/en/cas/1476-52-4_1032909.html">, 5 pages.
CAS No. 4298-15-1, "2-[4-[(7-chloroquinolin-4-yl)amino]pentylamino]ethanol", ChemSRc, retrieved on Jul. 29, 2021, retrieved from URL <"https://www.chemsrc.com/en/cas/4298-15-1_589766.html">, 4 pages.
CAS No. 54-05-7, "Chloroquine", ChemSRc, retrieved on Jul. 29, 2021, retrieved from URL <"https://www.chemsrc.com/en/cas/54-05-7_419322.html">, 16 pages.
CAS Registry No. 1809249-37-3, "L-Alanine, N-[(S)-hydroxyphenoxyphosphinyl]-, 2-ethylbutyl ester, 6-ester with 2-C-(4-aminopyrrolo[2,1-f][1,2,4]triazin-7-yl)-2,5-anhydro-D-altrononitrile", American Cemical Society, retrieved on Jul. 27, 2021, retrieved from URL <"https://commonchemistry.cas.org/detail?cas_rn=1809249-37-3">, 3 pages.
Chapman et al., "RSV604, a Novel Inhibitor of Respiratory Syncytial Virus Replication," Antimicrobial Agents and Chemotherapy, 2007, 51(9): 3346-3353.
Cho et al., "Discovery of the First C-Nucleoside HCV Polymerase Inhibitor (GS-6620) with Demonstrated Antiviral Response in HCV Infected Patients," J. Med. Chem., 2014, 57(5): 1812-1825.
Cho et al., "Synthesis and antiviral Activity of a Series of 1'-Substituted 4-aza-7,9-dideazaadenosine C-Nucleosides", Bioorganic & Medicinal Chemistry Letters, 2012, 22(8):2705-2707.
Cihlar et al., "Design and Profiling of GS-9148, a Novel Nucleotide Analog Active against Nucleoside-resistant Variants of Human Immunodeficiency Virus Type 1, and Its Orally Bioavailable Phosphonoamidate Prodrug, GS-9131," Antimicrobial Agents and Chemotherapy, 2008, 52(2): 655-665.
Clark et al., "Design, Synthesis, and Antiviral Activity of 2'-Deoxy-2'-fluoro-2'-C-methylcytidine, a Potent Inhibitor of Hepatitis C Virus Replication," Journal of Medicinal Chemistry, 2005, 48(17): 5504-5508.
Clarke et al., "Discovery ofbeta-D-2'-Deoxy-2'-alpha-Fluoro-4'-alpha-Cyano-5-aza-7,9-Dideaza Adenosine as a Potent Nucleoside Inhibitor of Respiratory Syncytial Virus with Excellent Selectivity Over Mitochondrial RNA and DNA Polymerases," Bioorganic & Medicinal Chemistry Letters, Apr. 29, 2015, 25: 2484-2487.
Colacino et al., "Synthesis and Biological Evaluation of Some 5-Nitro- and 5-Amino Derivatives of 2'-Deoxycytidine, 2',3'-Dideoxyuridine, and 2',3'-Dideoxycytidine," Nucleoside, Nucleotides & Nucleic Acids, 2003, 22(11): 2013-2026.
Cox et al., "Therapeutically administered ribonucleoside analogue MK-4482/EIDD-2801 blocks SARS-CoV-2 transmission in ferrets," Nature Microbiology, 2020, 6(1): 11-18.
Dai et al., "Synthesis of 2'-C-β-Fluoromethyluridine," Organic Letters, 2003, 5(6): 807-810.
Damont et al., "Synthesis of 1'-C-Fluoromethyladenosine," Nucleosides, Nucleotides, and Nucleic Acids, 2007, 26:1431-1434.
De Clercq, "Antiviral Dmgs: Current State of the Art," J. Clin. Virol., 2001, 22(1): 73-89.
De Clercq, "Molecular Targets for Antiviral Agents," The Journal of Pharmacology and Experimental Therapeutics, 2001, 297(1): 1-10.
De Francesco et al., "Approaching a New Era for Hepatitis C Virus Therapy: Inhibitors of the NS3-4A Serine Protease and the NS5B RNA-Dependent RNA Polymerase," Antiviral Research, 2003, 58(1): 1-16.
De Las Heras, "Synthesis of Ribosyl and Arabinosyl Cyanides by Reaction of 1-O-Acyl Sugars with Trimethylsilyl Cyanide," Journal of the Chemical Society, Perkin Transactions 1, 1982, pp. 903-907.
De Lombaert et al., "N-Phosphonomethyl Dipeptides and Their Phosphonate Prodrugs, a New Generation of Neutral Endopeptidase (NEP, EC 3.4.24.11) Inhibitors," J. Med. Chem., 1994, 37(4): 498-511.
Di Bisceglie et al., "The Unmet Challenges of Hepatitis C," Scientific American, Oct. 1999, pp. 80-85.
Dinnon et al., "A mouse-adapted model of SARS-CoV-2 to test COVID-19 countermeasures," Nature, Aug. 2020, 586: 560-566.
Dolzhenko et al., "Pyrazolo[1,5-a][1,3,5]Triazines(5-Aza-9-Deazapurines): Synthesis and Biological Activity," Heterocycles, 2008, 75(7): 1575-1622.
Domingo et al., "The quasispecies (extremely heterogeneous) nature of viral RNA genome populations: biological relevance—a review," Gene, 1985, 40: 1-8.
Dondoni et al., "Thiazole-Based Synthesis of Formyl C-Glycosides," Journal of Organic Chemistry, 1994, 59: 6404-6414.
Dudfield et al., "Synthesis of C- ribosyl imidazo[2,1-f][1,2,4]triazines as inhibitors of adenosine and AMP deaminases," J. Chem. Soc, Perkin Trans I, 1999, pp. 2929-2936.
Dudfield et al., "Synthesis of C-ribosyl 1,2,4-triazolo[3,4-f][1,2,4]triazines as Inhibitors of Adenosine and AMP Deaminasses," J. Chem. Soc., Perkin Trans. 1, 1999, pp. 2937-2942.
Durcan et al., "Hydroxychloroquine Blood Levels in Systemic Lupus Erythematosus: Clarifying Dosing Controversies and Improving Adherence", Journal of Rheumatology, 2015, 42(11):2092-2097.
Dymock et al., "Novel approaches to the treatment of hepatitis C virus infection," Antiviral Chemistry & Chemotherapy, 2000, 11(2): 79-96.
El Safadi et al., "5-Modified-2'-dU and 2'-dC as Mutagenic Anti HIV-1 Proliferation Agents: Synthesis and Activity," Journal of Medicinal Chemistry, 2010, 53(4): 1534-1545.
Farquhar et al., "Biologically Reversible Phosphate-Protective Groups," Journal of Pharmaceutical Sciences, 1983, 72(3): 324-325.
Fauquet et al., "Abbreviations for vertebrate virus species names", Archives of Virology, Dec. 31, 1999, pp. 1865-1880.
Flint et al., "Functional analysis of cell surface-expressed hepatitis C virus E2 glycoprotein," J. Virol., Aug. 1999, 73(8): 6782-6790.
Foster et al., "Deuterium isotope effects in studies of drug metabolism," Trends in Pharmacological Sciences, Jan. 1984, 5:524-527.
Franchetti et al., "Antitumor Activity of C-Methyl-β-D-ribofuranosyladenine Nuceoside Ribonuceotide Reductase Inhibitors," J. Med. Chem. 2005, 48: 4983-4989.
Freeman et al., "3 Prodrug Design for Phosphates and Phosphonates," Progress in Medicinal Chemistry, 1997, 34: 111-147.
Fukumoto et al., "Viral Dynamics of Hepatitis C Early After Orthotopic Liver Transplantation: Evidence for Rapid Turnover of Serum Virions," Hepatology, 1996, 24: 1351-1354.
Garcia et al., "Synthesis of (2,3,4,6-tetra-O-acetyl-alpha-D-glycopyranosyl)thiophene derivatives as new C-nucleoside analogues," J. Carbohydrate Chemistry, 2001, 20(7/8): 681-687.

(56) References Cited

OTHER PUBLICATIONS

Gardelli et al., "Phosphoramidate Prodrugs of 2'-C-Methylcytidine for Therapy of Hepatitis C Virus Infection," Journal of Medicinal Chemistry, 2009, 52(17): 5394-5407.
George et al., "Preparation of silyl-and germylmetallic compounds," Journal of the American Chemical Society, Jan. 1960, 82(2):403-6.
Gleeson et al., "Prediction of the Potency of Inhibitors of Adenosine Deaminase by QM/MM Calculations," Chem. Commun., 2003, pp. 2180-2181.
Gordon et al., "Remdesivir is a direct-acting antiviral that inhibits RNA-dependent RNA polymerase from severe acute respiratory syndrome coronavirus 2 with high potency," J. Biol. Chem., 2020, 295(20):6785-6797.
Gordon et al., "The antiviral compound remdesivir potently inhibits RNA-dependent RNA polymerase from Middle East respiratory syndrome coronavirus," Journal of Biol. Chemistry, 2020, 295(15):4773-4779.
Gordon et al., Control of Hepatitis C: A Medicinal Chemistry Perspective, J. Med. Chem., 2005, pp. 1-20, vol. 48, No. 1.
Greene et al., "Protective Groups in Organic Synthesis," John Wiley & Sons., 1991, pp. 118-142.
Greene et al., "Protective Groups in Organic Synthesis," published by John Wiley & Sons, v Inc., 1991, pp. 1-4, 10-14, 47-53 and 100-103.
Grein et al., "Compassionate Use of Remdesivir for Patients with Severe Covid-19", The New England Journal of Medicine, Apr. 2020, 382(24): 2327-2336.
Gudmundsson et al., "Synthesis of imidazo[1,2-a]pyridine C-Nucleosides with an Unexpected Site of Ribosylation," Journal of Organic Chemistry, 1997, 62: 3453-3459.
Gudmundsson et al., "The Condensation of 2,6-dichloroimidazo[1,2-a]pyridine C-nucleoside with an Unexpected Site of Ribosylation," Tetrahedron Letters, 1996, 7(14): 2365-2368.
Gunic et al., "Cyclic monophosphate prodrugs of base-modified 2'-C-methyl ribonucleosides as potent inhibitors of hepatitis C virus RNA replication," Bioorganic & Medicinal Chemistry Letters, 2007, 17: 2452-2455.
Hamann et al., "Synthesis and antiviral evaluation of 7,9-dideaza-8-thiapurine C-nucleoside derivatives," Collection Symposium Series, 2008, 10: 347-349.
Hamann et al., "Synthesis and antiviral evaluation of thieno[3,4-d]pyrimidine C-nucleoside analogues of 2',3'-dideoxy- and 2',3'-dideoxy-2',3'-didehydro-adenosine and -inosine," Bioorganic & Medicinal Chemistry, 2009, 17: 2321-2326.
Han et al., "Synthesis of 1-Chloroacetyl-1-dehydroxy-2,3,5-tri-O-benzoyl-β-D-ribofuranose. A Potentially Versatile Intermediate for the Synthesis of C-Nucleosides," Synthetic Communications, 1992, 22(19): 2815-2822.
Haraguchi et al., "Stereoselective Synthesis of 1'-C-Branched Uracil Nucleosides From Uridine," Nucleosides & Nucleotides, 1995, 14(3-5): 417-420.
Harcourt et al., "Molecular Characterization of the Polymerase Gene and Genomic Termini of Nipah Virus," Virology, 2001, 287: 192-201.
Harki et al., "Synthesis and Antiviral Activity of 5-Substituted Cytidine Analogues: Identification of Potent Inhibitor of Viral RNA-Dependent RNA Polymerases," Journal of Medicinal Chemistry, 2006, 49(21): 6166-6169.
Hayashi et al., "C-Nucleosides, A Synthesis of 2-Substituted 7-(b-D-Ribofuranosyl)-Pyrrolo[2,1-f]-1,2,4-Triazines. A New Type of "Purine Like" C-Nucleoside," Heterocycles, 1992, 34(3): 569-574.
Hecker et al., "Liver Targeted Prodrugs of 2'-C-Methyladenosine for Therapy of Hepatitis C Virus Infection," J. Med. Chem., 2007, 50(16): 3891-3896.
Hoffmann et al., "When, in the context of drug design, can a fluorine atom successfully substitute a hydroxyl group?," International Journal of Quantum Chemistiy, 2002, 89: 419-427.
Holshue et al., "First Case of 2019 Novel Coronavirus in the United States", The New England Journal of Medicine, Jan. 2020, 9 pages.

Huang et al., "Recent development of therapeutics for chronic HCV infection," Antiviral Research, Sep. 2006, 71(2-3): 351-362.
Itoh et al., "Divergent and Stereocontrolled Approach to the Synthesis of Uracil Nucleosides Branched at the Anomeric Position," J. Org. Chem. 1995, 60: 656-662.
Jasko et al., "5'-Phosphonates of Ribonucleosides and 2'-Deoxyribonucleosides: Synthesis and Antiviral Activity," Nucleosides & Nucleotides, 1993, 12(8): 879-893.
Kabat et al., "Nucleosides, CXLVIII, Synthesis of 6-(β-D-Ribofuranosyl)picolinamide: A Novel C-Nucleoside from D-Ribonolactone", Chemical & Pharmaceutical Bulletin, 1988, pp. 634-640, vol. 36, No. 2.
Kaewkhao et al., "High sensitivity methods to quantify chloroquine and its metabolite in human blood samples using LC-MS/MS", Bioanalysis, Mar. 2019, 11(5):333-347.
Kalil et al., "Baricitinib plus Remdesivir for hospitalized adults with Covid-19," New England Journal of Medicine, Dec. 11, 2020, 13 pages.
Khamnei et al., "Neighboring Group Catalysis in the Design of Nucleotide Prodrugs," J. Med. Chem., 1996, 39(20): 4109-4115.
Kim et al., "Reversal of the Progression of Fatal Coronavirus Infection in Cats by a Broad-Spectrum Coronavirus Protease Inhibitor," PLOS Pathogens, Mar. 30, 2016, 18 pages.
Klumpp et al., "The Novel Nucleoside Analog R1479 (4'-Azidocytidine) is a Potent Inhibitor of NS5B-dependent RNA Synthesis and Hepatitis C virus Replication in Cell Culture," Journal of Biological Chemistiy, 2006, 281(7): 3793-3799.
Knaggs et al., A QSAR Study Investigating the Effect of L-Alanine Ester Variation on the Anti-HIV Activity of Some Phosphoramidate Derivatives of d4T, Bioorganic & Medicinal Chemistry Letters, 2000, 10: 2075-2078.
Knutsen et al., "Synthesis of Imidazo-fused Bridgehead-nitrogen C-Nucleosides : Coupling-Elimination Reactions of 2,5-Anhydro-3,4,6-tri-O-benzoyl-D-allonic Acid," J. Chem. Soc. Perkin Trans I, 1985, pp. 621-630.
Knutsen et al., "Synthesis of Imidazo-fused Bridgehead-nitrogen C-Nucleosides via Dehydrative Coupling Reactions of 2,5-Anhydro-3,4,6-tri-O-benzoyl-D-allonic Acid," J. Chem. Soc. Perkin Trans I, 1984, pp. 229-238.
Kobe et al., "Use of Distance Geometry Approach for the In Vitro Antiviral Activity Evaluation of N-bridgehead C-nucleosides," European J. Med. Chem., 1992, 27(3): 259-266.
Kuzik et al., "Nebulized Hypertonic Saline in the Treatment of Viral Bronchiolitis in Infants", The Journal of Pediatrics, Sep. 2007, 151(3):266-270.e1.
Lefebvre et al., "Mononucleoside Phosphotriester Derivatives with S-Acyl-2-thioethyl Bioreversible Phosphate-Protecting Groups: Intracellular Delivery of 3'-Azido-2',3'-dideoxythymidine 5'-Monophosphate," Journal of Medicinal Chemistry, 1995, 38(20): 3941-3950.
Lefebvre et al., "Synthesis, Decomposition Pathways and 'In Vitro' Evaluation of Bioreversible Phosphotriesters of Azt, Nucleosides," Nucleotides & Nucleic Acids, 1995, 14(3-5): 763-766.
Leyssen et al., "Molecular strategies to inhibit the replication of RNA Viruses," Antiviral Research, 2008, 78:9-25.
Lindell et al., "Synthesis and Biochemical Testing of 3-(Carboxyphenylethyl)imidazo[2,1-f][1,2,4]triazines as Inhibitors of AMP Deaminase," ACS Medicinal Chemistry Letters, 2010, 1(6): 286-289.
Lo et al., "GS-5734 and its parent nucleoside analog inhibit Filo-, Pneumo-, and Paramyxoviruses," Scientific Reports, 2017, 7(43395):1-7.
Lovelette, "1,2,4-Triazines. Synthesis of selected members of the s-triazolo[3,4-f][1,2,4]triazine and tetrazolo[1,5-f][1,2,4]triazine ring systems," Journal of Heterocyclic Chemistry, 1979, 16: 555-560.
Lu, Chengping, Veterinary Microbiology 5th edition, Jan. 31, 2013, p. 431, China Agriculure Press (No English Translation available).
Martell et al., "Hepatitis C Virus (HCV) Circulates as a Population of Different but Closely Related Genomes: Quasispecies Nature of HCV Genome Distribution," Journal of Virology, 1992, 6695: 3225-3229.
Martin et al., "Hint2, A Mitochondrial Apoptotic Sensitizer Down-Regulated in Hepatocellular Carcinoma," Gastroenterology, Jun. 2006, 130(7):2179-21880.

(56) References Cited

OTHER PUBLICATIONS

Mason et al., "Polyadenylation-dependent screening assay for respiratory syncytial virus RNA transcriptase activity and identification of an inhibitor," Nucleic Acids Research, 2004, 32(16): 4758-4767.

Matulic-Adamic et al., "Synthesis of 3-(β-D-Ribofuranosyl)-2-Fluoropyridine and 3-(β-D-Ribofuranosyl)-Pyridin-2-one," Tetrahedron Letters, 1997, 38(2): 203-206.

Matulic-Adamic et al., "Synthesis of 5-(β-D-Ribofuranosyl)-Pyridin-2-one: a 'Deletion-Modified' Analogue of Uridine," Tetrahedron Letters, 1997, 38(10): 1669-1672.

McGuigan et al. "Application of Phosphoramidate ProTide Technology Significantly Improves Antiviral Potency of Carbocyclic Adenosine Derivatives," J. Med. Chem., 2006, 49: 7215-7226.

McGuigan et al., "Aryl Phosphoramidate Derivatives of d4T Have Improved Anti-HIV Efficacy in Tissue Culture and May Act by the Generation of a Novel Intracellular Metabolite," J. Med. Chem., 1996, 39: 1748-1753.

McGuigan et al., "Design, synthesis and biological evaluation of phosphorodiamidate prodrugs of antiviral and anticancer nucleosides," European Journal of Medical Chemistry, 2013, 70:326-340.

McGuigan et al., "Intracellular Delivery of Bioactive AZT Nucleotides by Aryl Phosphate Derivatives of AZT," J. Med. Chem., 1993, 36(8): 1048-1052.

Mehellou et al., ""Aryloxy Phosphoramidate Triesters: a Technology for Delivering Monophosphorylated Nucleosides and Sugars into Cells,"" ChemMedChem, 2009, 4:1779-1791.

Meppen et al., "Cyclic phosphoramidates as prodmgs of 2'-C-methylcytidine," European Journal of Medicinal Chemistry, 2009, 49(9): 3765-3770.

Meppen et al., "Medi-404—A Prodrug Approach for the Treatment of HCV Infection," Abstracts of papers, 236th ACS National Meeting, Philadelphia, PA, United States, Aug. 17-21, 2008, 1 page.

Metobo et al., "Practical synthesis of 1'—substituted Tubercidin C-nucleoside analogs," Tetrahedron Letters, Feb. 2012, 53(5):484-486.

Migliaccio et al., "Characterization of Resistance to Non-obligate Chain-terminating Ribonucleoside Analogs That Inhibit Hepatitis C Virus Replication in vitro," The Journal of Biological Chemistry, 2003, 278(49): 49164-49170.

Mitchell et al., "Bioreversible Protection for the Phospho Group: Bioactivation of the Di(4-acyloxybenzyl) and Mono(4-acyloxybenzyl) Phosphoesters of Methylphosphonate and Phosphonoacetate," J. Chem. Soc., Perkin Trans. 1, 1992, pp. 2345-2353.

Mitchell et al., "Synthesis of C-Nucleoside Isosteres of 9-(2-Hydroxyethoxymethyl)guanine (Acyclovir)," J. Het. Chem., 1984, 21(3): 697-699.

Moennig et al., "The Pestiviruses", Advances in Virus Research, 1992, 41: 53-98.

Moradpour et al., "Replication of hepatitis C virus," Nature Reviews Microbiology, 2007, 5(6): 453-463.

Morris, "Mechanisms of action and therapeutic role of corticosteroids in asthma", J. Allergy Clin. Immunol., Jan. 1985, 75(1 Pt): 1-13.

Moscow et al., "Reduced Folate Carrier Gene (RFC1) Expression and Anti-Folate Resistance in Transfected and Non-Selected Cell Lines," International Journal of Cancer, 1997, 72: 184-190.

Mossel et al., "Exogenous ACE2 expression allows refractory cell lines to support severe acute respiratory syndrome coronavirus replication," Journal of Virology, Mar. 15, 2005, 79(6):3846-50.

Munster et al., "Hydroxychloroquine concentration-response relationships in patients with rheumatoid arthritis", Arthritis Rheumatology, Jun. 2002, 46(6):1460-1469.

Murakami et al., "Mechanism of Activation of Beta-D-2'-Fluoro-2'-C-Methylcytidine and Inhibition of Hepatitis C Virus NS5B RNA Polymerase", Antimicrob Agents Chemother., Feb. 2007, 51(2):503-509.

Murakami et al., "Mechanism of Activation of PSI-7851 and Its Diastereoisomer PSI-7977", The Journal of Biological Chemistry, 2010, 285(45):34337-34347.

Murphy et al., "The Nucleoside Analog GS-441524 Strongly Inhibits Feline Infectious Peritonisitis (F1P) Virus in Tissue Culture and Experimental Cat Infection Studies", Veterinary Microbiology, 2018, 219:226-233.

Neumann et al., "Hepatitis C Viral Dynamics in Vivo and the Antiviral Efficacy of Interferon-α Therapy", Science, 1998, 282:103-107.

Nishimura et al., "Synthesis of pyrrolo[2,1-f][1,2,4]triazine C-nucleosides. Isosteres of sangivamycin, tubercidin, and toyocamycin," Carbohydrate Research, 2001, 331: 77-82.

Ogura et al., "Reaction of Ethynyl Compounds with Lactones," Journal of Organic Chemistry, 1972, 37(1): 72-75.

Olsen et al., "A 7-Deaza-Adenosine Analog Is a Potent and Selective Inhibitor of Hepatitis C Virus Replication with Excellent Pharmacokinetic Properties," Antimicrobial agents and Chemotherapy, 2004, 3944-3953.

Otter et al., "Conformational Properties of Purine-Like C-Nucleosides," Nucleosides & Nucleotides, 1996, 15(1-3): 793-807.

Pankiewicz et al., "C-Nucleoside Analogues of Nicotinamide Mononucleotide (NMN)," Nucleosides and Nucleotides, 1988, 7(5 &6): 589-593.

Pankiewicz et al., "Efficient Synthesis of 5-(β-D-Ribofuranosyl)nicotinamide and its α-Isomer," Journal of Organic Chemistry, 1988, 53: 3473-3479.

Patani et al., "Bioisosterism: a rational approach in drug design," Chem. Rev., 1996, 96:3147-3176.

Patil et al., "4-Aza-7,9-Dideazaadenosine, a New Cytotoxic Synthetic C-Nucleoside Analogue of Adenosine," Tetrahedron Letters, 1994, 35(30): 5339-5342.

Patil et al., "C-Glycosylation of Substituted Heterocycles under Friedel-Crafts Conditions (II): Robosylation of Multi-Functionalized Thiophenes and Furans for the Synthesis of Purine-Like C-Nucleosides," Nucleosides & Nucleotides, 1990, 9(7): 937-956.

Patil et al., "Synthesis of Pyrrolo[2,1-f][1,2,4]triazine Congeners of Nucleic Acid Purines via the N-Amination of 2-Substituted Pyrroles," J. Het. Chem., 1994, 31: 781-786.

Patil et al., "Synthesis of some new thieno[3,4-d]pyrimidines and their C-nucleosides," Journal of Heterocyclic Chemistry, 1993, 30(2): 509-515.

Pelet et al., "High throughput screening assay for negative single stranded RNA virus polymerase inhibitors," J. Virol. Methods, Sep. 2005, 128(1-2): 29-36.

Perrone et al., "Application of the Phosphoramidate ProTide Approach to 4'-Azidouridine Confers Sub-micromolar Potency versus Hepatitis C Virus on an Inactive Nucleoside", Journal of Medicinal Chemistry, 2007, 50(8):1840-1849.

Perrone et al., "First Example of Phosphoramidate Approach Applied to a 4'-Substituted Purine Nucleoside (4'-Azidoadenosine): Conversion of an Inactive Nucleoside to a Submicromolar Compound versus Hepatitis C Virus," Journal of Medicinal Chemistry, Oct. 2007, 50(22): 5463-5470.

Peterson et al., "Prodrug approaches to improving the oral absorption of antiviral nucleotide analogues," Expert Opinion, Drug Deliv., 2009, 6(4): 405-420.

Piccirilli et al., "A Direct Route to 3-(D-Ribofuranosyl)pyridine Nucleosides," Helvetica Chimica Acta, 1991, 74: 397-406.

Pierra et al., "Synthesis and Pharmacokinetics of Valopicitabine (NM283), and Efficient Prodrug of the Potent Anti-HCV Agent 2'-C-Methylcytidine," Journal of Medicinal Chemistry, 2006, 49(22): 6614-6620.

Poduch et al., "Design of Inhibitors of Orotidine Monophosphate Decarboxylase Using Bioisosteric Replacement and Determination of Inhibition Kinetics," Journal of Medicinal Chemistry, 2006, 49(16): 4937-4945.

Porter et al., "Zika virus, drug discovery, and student projects," ScienceBlogs, Mar. 9, 2016, 7 pages.

Pruijssers et al., "Remdesivir Inhibits SARS-CoV-2 in Human Lung Cells and Chimeric SARS-CoV Expressing the SARS-CoV-2 RNA Polymerase in Mice," Cell Reports, 2020, 32(107940):1-16.

Puech et al., "Intracellular Delivery of Nucleoside Monophosphates through a Reductase-mediated Activation Process," Antiviral Research, 1993, 22(4): 155-174.

(56) References Cited

OTHER PUBLICATIONS

Ramasamy et al., "Synthesis and Antitumor Activity of Certain 3-B-D-Ribofuranosyl-1,2,4-triazolo[3,4-f]-1,2,4-triazines Related to Formycin Prepared via Ring Closure of a 1,2,4-Triazine Precursor," J. Med. Chem., 1986, 29(11): 2231-2235.
Rao et al., "C-Glycosylation of Substituted Heterocycles under Friedel-Crafts Conditions (I): A Two-Step Synthesis of the Thieno[3,4-d]Pyrimidine C-Nucleoside Analog of Inosine," Tetrahedron Letters, 1988, 29(29): 3537-3540.
Reddy et al., "Stereoselective Synthesis of Nucleoside Monophosphate HepDirect™ Prodrugs," Tet. Lett., 2005, 46: 4321-4324.
Ross et al., "Synthesis of Diastereomerically Pure Nucleotide and Phosphoramidates," J. Org. Chem., 2011, 76: 8311-8319.
Sacramento et al., "The clinically approved antiviral drug Sofosbuvir inhibits Zika Virus replication," Nature, Jan. 18, 2017, 7: 40920, 12 pages.
Schnirring, "China releases genetic data on new coronavirus, now deadly," CIDRAP News, Jan. 2020, retrieved on Mar. 15, 2022, retrieved from URL <https://www.cidrap.umn.edu/news-perspective/2020/01/china-releases-genetic-data-new-coronavirus-now-deadly>, pages.
Schul et al., "A Dengue Fever Viremia Model in Mice Shows Reduction in Viral Replication and Suppression of the Inflammatory Response after Treatment with Antiviral Drugs," Journal of Infectious Diseases, 2007, 195: 665-674.
Schultz, "Prodrugs of Biologically Active Phosphate Esters," Bioorganic & Medicinal Chemistry, 2003, 11: 885-898.
Scott et al., "Interferon-a-2b Plus Ribavirin: A Review of its Use in the Management of Chronic Hepatitis C," Drugs, 2002, 62(3): 507-556.
Sheahan et al., "Broad-spectrum antiviral GS-5734 inhibits both epidemic and zoonotic coronaviruses", Science Translational Medicine, Jun. 2017, 9(396):eaa13653, 11 pages.
Sheahan et al., "Comparative therapeutic efficacy of remdesivir and combination lopinavir, ritonavir, and interferon beta against MERCoV," Nature Communications, 2020, 11(222):1-14.
Sheahan, "Preparing for future pandemics, today with broad-spectrum antivirals", Nature Portfolio Microbiology Community, Jan. 10, 2020, retrieved on May 13, 2021, retrieved from URL <"https://naturemicrobiologycommunity.nature.com/posts/58125-preparing-for-future-pandemics-today-with-broad-spectrum-antivirals", 13 pages.
Shekunov et al., "Crystallization processes in pharmaceutical technology and drug delivery design," Journal of Crystal Growth, 2000, 211: 122-136.
Shi et al., "Synthesis and anti-viral activity of a series of d- and l-2'-deoxy-2'-fluororibonucleosides in the subgenomic HCV replicon system," Bioorganic & Medicinal Chemistry, Mar. 2005, 13(5):1641-1652.
Siegel et al., ""Discovery and Synthesis of a Phosphoramidate Prodrug of a Pyrrolo[2,1-f][triazin-4-amino] Adenine C-Nucleoside (GS-5734) for the Treatment of Ebola and Emerging Viruses,"" J. Med. Chem., 2017, 60, 5, 1648-1661 Supplementary Material.
Siegel et al., "Discovery and Synthesis of a Phosphoramidate Prodrug of a Pyrrolo[2,1-f][triazin-4-amino] Adenine C-Nucleoside(GS-5734) for the Treatment of Ebola and Emerging Viruses", Journal of Medicinal Chemistry, 2017, 60(5): 1648-1661.
Silverman et al., "The Organic Chemistry of Drug Design and Drug Action," Elsevier Science, 1992, pp. 19-23.
Silverman, "The Organic Chemistry of Drug Design and Drug Action," Elsevier Science, 2nd Ed., 2004, pp. 29-34.
Sofia et al., "Discovery of a β-d-2'-Deoxy-2'-α-fluoro-2'-β-C-methyluridine Nucleotide Prodrug (PSI-7977) for the Treatment of Hepatitis C Virus," Journal of Medicinal Chemistry, Sep. 2010, 53(19):7202-7218.
Srivastav et al., "Antiviral Activity of Various 1-(2'-Deoxy-β-D-lyxofuranosyl), 1-(2'-Fluoro-β-D-xylofuranosyl), 1-(3'-Fluor-β-D-arabinofuranosyl), and 2'-Fluoro-2',3'-didehydro-2',3'-dideoxyribose Pyrimidine Nucleoside Analogues against Duck Hepatitis B Virus (DHBV) and Human Hepatitis B Virus (HBV) Replication," Journal of Medicinal Chemistiy, 2010, 53(19): 7156-7166.
Stein et al., "Phosphorylation of Nucleoside Analog Antiretrovirals: A Review for Clinicians, " Pharmacotherapy, Jan. 2001, 21(1):11-34.
Streetman, "Drug Interaction Concerns for COVID-19 Treatments", Wolters Kluwer, Apr. 15, 2020, retrieved on Sep. 7, 2021, retrieved from URL <"https://www.wolterskluwer.com/en/expert-insights/drug-interaction-concerns-for-covid-19-treatments">, 10 pages.
Sun, "Remdesivir for Treatment of COVID-19: Combination of Pulmonary and IV Administration May Offer Additional Benefit", The AAPS Journal, 2020, 22(77):1-6.
Tapia et al., "Combination of a Mutagenic Agent with a Reverse Transcriptase Inhibitor Results n Systematic Inhibition of HIV-1 Infection," Virology, 2005, 338: 1-8.
Totura et al., "Broad-spectrum coronavirus antiviral drug discovery", Expert Opinion on Drug Discovery, Mar. 2019, 17 pages.
Towner et al., "Newly Discovered Ebola Virus Associated with Hemorrhagic Fever Outbreak in Uganda," PLoS Pathogens, 2008, 4(11): e1000212, 6 pages.
Tschesnokov et al., "Template-dependent inhibition of coronavirus RNA-dependent RNA polymerase by remdesivir reveals a second mechanism of action," J. Biol. Chem., 2020, 295(47):16156-16165.
Uchiyama et al., "O-selective Phosphorylation of Nucleosides without N-protection," J. Org. Chem., Jan. 1, 1993, 58(2): 373-379.
Vaghefi et al., "Synthesis and Antiviral Activity of Certain Nucleoside 5'-Phosphonoformate Derivatives," Journal of Medicinal Chemistry, 1986, 29(8): 1389-1393.
Venkatachalam et al., "Effect of change in nucleoside structure on the activation and antiviral activity of phosphoramidate derivatives," Bioorganic & Medicinal Chemistry, 2005, 13: 5408-5423.
Walker et al., "Plasma chloroquine and desethylchloroquine concentrations in children during and after chloroquine treatment for malaria.", British Journal Clinical Pharmacology, Dec. 1983, 16(6):701-705.
Wang et al., "ANNOVAR: functional annotation of genetic variants from high-throughput sequencing data," Nucleic Acids Research, 2010, 38(16): e164, 7 pages.
Wang et al., "Remdesivir and chloroquine effectively inhibit the recently emerged novel coronavirus (2019-nCoV) in vitro", Cell Research, 2020, 30:269-271.
Warren et al., "Protection against filovirus diseases by a novel broad-spectrum nucleoside analogue BCX4430", Nature, Apr. 2014, 508(7496):402-405.
Warren et al., "Therapeutic efficacy of the small molecules GS-5734 against EBOLA virus in rhesus monkeys", Nature, Mar. 17, 2016, 531(7594): 381-385.
Wolfel et al., "Virological assessment of hospitalized patients with COVID-2019," Nature, Apr. 2020, 581: 465-470.
Wu et al., "Synthetic Methodologies for C-Nucleosides," Synthesis, 2004, 10: 1533-1553.
Xie et al., "A nanoluciferase SARS-CoV-2 for rapid neutralization testing and screening of anti-infective drugs for COVID-19," Nature Communications, Oct. 15, 2020, 11(1):1-11.
Xie et al., "Weinreb Amide Approach to the Practical Synthesis of a Key Remdesivir Intermediate," The Journal of Organic Chemistiy, 2021, 86:5065-5072.
Yamanaka et al., "Metabolic Studies on BMS-200475, a New Antiviral Compound Active against Hepatitis B Virus," Antimicrobial Agents and Chemotherapy, 1999, p. 43(1): 190.
Yang et al., "Lewis acid catalyzed direct cyanation of indoles and pyrroles with N-cyano-N-phenyl-p-toluenesulfonamide (NCTS)," Organic Letters, 2011, 13(20): 5608-5611.
Yates et al., "The evolution of antiviral nucleoside analogues: A review for chemists and non-chemists. PartII: Complex modifications to the nucleoside scaffold", Antiviral Research, Dec. 8, 2018, 162:5-21.
Yoon et al., "High-throughput screening-based identification of paramyxovims inhibitors," J. Biomol. Screen., Aug. 2008, 13(7): 591-608.
Yoshimura et al., "Synthesis and Biological Evaluation of 1'-C-Cyano-Pyrimidine Nucleosides," Nucleosides & Nucleotides, 1996, 15(1-3): 305-324.

(56) References Cited

OTHER PUBLICATIONS

Zhang et al., "A Practical Synthesis of (2R)-3,5-di-O-benzoyl-2-fluoro-2-C-methyl-D-ribono-y-lactone", Tetrahedron: Asymmetry, 2009, 20:305-312.
Zhu et al., "A novel coronavirus from patients with pneumonia in China, 2019," New England Journal of Medicine, Jan. 24, 2020, 14 pages.
ARIPO Patent Office, Form 21 and Substantive Examination Report (in English) for AP Application No. AP/P/2010/005439, dated Mar. 18, 2014.
ARIPO Patent Office, Form 21 for AP Patent Application No. AP/P/2011/005818, Sep. 19, 2013.
ARIPO Patent Office, Search and Exam Report for AP Application No. AP/P/2012/006189, dated Jun. 26, 2014.
ARIPO Patent Office, Search Report for AP Patent Application No. AP/P/2011/005818, dated Sep. 19, 2013.
Australia Patent Office, First Examination Report for AU Patent Application No. 2009240630, dated Jun. 14, 2012.
Australia Patent Office, Patent Examination Report No. 1 for AU Application No. 2011306066, dated Nov. 21, 2013.
Australia Patent Office, Patent Examination Report No. 1 for AU Patent Application No. 2010213873, dated Jun. 4, 2014.
Chile Patent Office, First Office Action for CL Patent Application No. 1906-2011.
Chile Patent Office, Opposition for CL Patent Application No. 727-2013, Oct. 15, 2013.
Chile Patent Office, Second Office Action for CL Patent Application No. 1906-2011, dated Oct. 16, 2013.
Chinese Patent Office, First Examination Report for CN Patent Application No. 200980120218.8, dated Nov. 13, 2012.
Chinese Patent Office, First Office Action for CN Patent Application No. 201080011690.0, dated Jun. 8, 2013.
Chinese Patent Office, Notification of Reexamination for CN Patent Application No. 200980120218.8, dated Sep. 1, 2014.
Chinese Patent Office, Notification of the Second Office Action & Search Report for CN Patent Application No. 201080011690.0, dated Jan. 8, 2014.
Chinese Patent Office, Notification of the Third Office Action for CN Patent Application No. 201080011690.0, dated Jul. 29, 2014.
Chinese Patent Office, Rejection Decision for CN Patent Application No. 200980120218.8, dated Feb. 7, 2014.
Chinese Patent Office, Second Examination Report for CN Patent Application No. 200980120218.8, dated Jun. 21, 2013.
Columbia Patent Office, First Examination Report (in English) for CO Patent Application No. 10-131479, dated Oct. 23, 2012.
Columbia Patent Office, Office Action for CO Patent Application No. 11-109.501, dated Nov. 27, 2012.
Columbia Patent Office, Office Action for CO Patent Application No. 13-235103-1, dated Aug. 27, 2014.
Columbia Patent Office, Resolution No. 56673 for CO Patent Application No. 10-131479, dated Sep. 27, 2013.
Columbia Patent Office, Second Examination Report (in English) for CO Patent Application No. 10-131479, dated Jun. 20, 2013.
Columbian Patent Office, Office Action No. 425 for CO Patent Application No. 12 050 579, dated Jan. 21, 2014.
Ecuador Patent Office, Opposition for EC Patent Application No. SP-2012-11817, May 27, 2013.
El Salvador Patent Office, Official Action for SV National Phase Entry of International Application No. PCT/US2010/049471, dated Nov. 6, 2013.
Eurasian Patent Office, First Examination Report for EA Patent Application No. 201071128, dated Apr. 25, 2012.
Eurasian Patent Office, First Office Action for EA Patent Application No. 201190110/28, dated Apr. 26, 2012.
Eurasian Patent Office, First Office Action for EA Patent Application No. 201390141/28, with English translation.
Eurasian Patent Office, Office Action for EA Patent Application No. 201390152, dated Apr. 14, 2014.
Eurasian Patent Office, Official Action for EA Patent Application No. 201390133, dated Mar. 27, 2014.
Eurasian Patent Office, Second Examination Report for EA Patent Application No. 201071128, dated Oct. 24, 2012.
Eurasian Patent Office, Second Office Action for EA Patent Application No. 201190110/28, dated Jan. 28, 2013.
Eurasian Patent Office, Third Examination Report for EA Patent Application No. 201071128, dated Apr. 29, 2013.
Eurasian Patent Office, Third Office Actionfor EA Application No. 201190110/28, dated Oct. 18, 2013.
European Patent Office, Communication pursuant to Article 94(3) EPC for EP Patent Application No. 10763083.2, dated May 2, 2014.
European Patent Office, Communication pursuant to Article 94(3) EPC for EP Patent Application No. 11715792.5, dated Feb. 14, 2014.
European Patent Office, Communication under 161/162 for EP Patent Application No. 10704068.5, dated Sep. 6, 2011.
European Patent Office, Communication under 161/162 for EP Patent Application No. 10763083.2, dated May 11, 2012.
European Patent Office, Communication under 161/162 for EP Patent Application No. 11715792.5, dated Apr. 26, 2013.
European Patent Office, First Office Action for EP Patent Application No. 10704068.5, dated Jun. 18, 2012.
Indonesia Patent Office, First Examination Report for ID Patent Application No. W00 2010 03957, dated Apr. 25, 2013.
Indonesia Patent Office, Substantive Examination Report Stage 1 for ID Application No. W-00201103126, dated Jun. 10, 2014.
Israel Patent Office, First Examination Report for IL Patent Application No. 208701, dated Jan. 13, 2013.
Israel Patent Office, First Office Action for IL Patent Application No. 214396, dated Jul. 8, 2013.
Israel Patent Office, Notification of Defects for IL Patent Application No. 214396, dated Nov. 11, 2013.
Israel Patent Office, Notification of Defects for IL Patent Application No. 218599, dated Aug. 25, 2014.
Israel Patent Office, Notification of Defects for IL Patent Application No. 208701, dated Aug. 25, 2014.
Israel Patent Office, Notification Prior to Examination for IL Patent Application No. 218599, dated Nov. 13, 2012.
Japanese Patent Office, First Examination Report for JP Patent Application No. 2011-506429, dated Aug. 22, 2013.
Japanese Patent Office, Notice of Reasons for Rejection for Japanese Patent Appln. No. JP 2017-520934, dated Mar. 30, 2018.
Japanese Patent Office, Notification of Reasons for Rejection for JP Application No. 2011-549324, dated Jul. 28, 2014.
Japanese Patent Office, Notification of Reasons for Rejection for JP Application No. 2011-549324, dated Mar. 26, 2014.
Japanese Patent Office, Notification of Reasons for Rejection for JP Patent Application No. 2012-529958, dated Aug. 5, 2014.
Mexico Patent Office, English translation of Office Action for MX Application No. MX/a/2013/003179, dated Feb. 25, 2014.
Mexico Patent Office, First Examination Report (in English) for MX Patent Application No. MX/a/2010/011661, dated Oct. 26, 2011.
Mexico Patent Office, Office Action for MX Application No. MX/a/2011/008409, dated Mar. 25, 2014.
New Zealand Patent Office, First Examination Report for NZ Patent Application No. 588670, dated Apr. 8, 2011.
New Zealand Patent Office, First Examination Report for NZ Patent Application No. 608070, dated Nov. 7, 2013.
New Zealand Patent Office, Further Examination Report for NZ Application No. 594370, dated Oct. 8, 2013.
PCT International Preliminary Report on Patentability and Written Opinion for PCT International Application No. PCT/US2009/041432, dated Oct. 26, 2010, 7 pages.
PCT International Preliminary Report on Patentability and Written Opinion for PCT International Application No. PCT/US2010/049471, dated Mar. 27, 2012, 7 pages.
PCT International Preliminary Report on Patentability and Written Opinion for PCT International Application No. PCT/US2011/038253, dated Dec. 4, 2012, 6 pages.
PCT International Preliminary Report on Patentability for PCT International Application No. PCT/US2010/023586, dated Aug. 16, 2011, 6 pages.

(56) References Cited

OTHER PUBLICATIONS

PCT International Preliminary Report on Patentability for PCT International Application No. PCT/US2011/028897, dated Mar. 26, 2013, 7 pages.
PCT International Preliminary Report on Patentability for PCT International Application No. PCT/US2011/029441, dated Mar. 26, 2013, 7 pages.
PCT International Search Report and Written Opinion for PCT International Application No. PCT/US2009/041432, dated Aug. 11, 2009, 11 pages.
PCT International Search Report and Written Opinion for PCT International Application No. PCT/US2011/028897, dated Aug. 1, 2011, 6 pages.
PCT International Search Report and Written Opinion for PCT International Application No. PCT/US2011/029441, dated Aug. 1, 2011, 5 pages.
PCT International Search Report and Written Opinion for PCT International Application No. PCT/US2011/038253, dated Jul. 29, 2011, 4 pages.
PCT International Search Report and Written Opinion for PCT International Application No. PCT/US2017/028251, dated Oct. 16, 2017, 22 pages.
PCT International Search Report and Written Opinion for PCT International Application No. PCT/US2017/028251, dated Sep. 13, 2017, 22 pages.
PCT International Search Report and Written Opinion for PCT International Application No. PCT/US2010/023586, dated Aug. 4, 2010, 4 pages.
PCT International Search Report and Written Opinion for PCT International Application No. PCT/US2010/049471, dated Nov. 18, 2010, 11 pages.
PCT International Search Report and Written Opinion in International Application No. PCT/US2021/034764, dated Aug. 23, 2021, 16 pages.
Peru Patent Office, Office Action in PE Application No. 1464, dated Sep. 12, 2013.
Resolution No. 48031 for CO Patent Application No. 10-121.513, (8 pages) (English translation).
Ukraine Patent Office, First Examination Report for UA Patent Application No. 2010 13030, dated Mar. 2, 2013.
Ukraine Patent Office, First Office Action for UA Application No. a 2011 10568.
Ukraine Patent Office, Second Office Action for UA Patent Application No. 2011 10568, dated Aug. 11, 2014.
Vietnam Patent Office, First Examination Report for VN Patent Application No. 1-2010-02939, dated Apr. 19, 2012.
Vietnam Patent Office, Second Examination Report for VN Patent Application No. 1-2010-02939, dated Jul. 26, 2012.
Adlington et al., "Synthesis of novel C-nucleosides with potential applications in combination and parallel synthesis," Tetrahedron Letters, 2000, 41:575-578.
Khan et al., "Coronaviruses disease 2019 (COVID-19): Causative agent, mental health concerns, and potential management options," Journal of Infection and Public Health, Dec. 2010, 13(12):1840-1844.
Kulli, "K Banhatti Polynomials of Remdesivir, Chloroquine, Hydroxychloroquine: Research Advances for the Prevention and Treatment of COVID-19," SSRG International Journal of Applied Chemistry, May-Aug. 2020, 7(2):48-55.
Kushner et al., "Pharmacological uses and perspectives of heavy water and deuterated compounds," Canadian Journal of Physiology and Pharmacology, Feb. 1999, 77(2):79-88.
Liu et al., "Hydroxychloroquine, a less toxic derivative of chloroquine, is effective in inhibiting SARS-CoV-2 infection in vitro," Cell Discovery, Mar. 18, 2020, 6:16, 4 pages.
Owusu et al., "A Comparison Analysis on Remdesivir, Favipiravir, Hydroxychloroquine, Chloroquine and Azithromycin in the Treatment of Corona Virus Disease 2019 (COVID-19)—A Review," World Journal of Pharmacy and Pharmaceutical Sciences, May 2020, 9(5):121-133.
Pizzorno et al., "In vitro evaluation of antiviral activity of single and combined repurposable drugs against SARS-CoV-2," Antiviral Research, Sep. 2020, 181:104878.
Sahakijpijarn et al., "Development of Remdesivir as a Dry Powder for Inhalation by Thin Film Freezing," Pharmaceutics, Oct. 2020, 12(11):1002, 27 pages.
Stella et al., "Cyclodextrins," Toxicologic Pathology, 2008, 36(1):30-42.
Szente et al., "Sulfobutylether-beta-cyclodextrin-enabled antiviral remdesivir: Characterization of electrospun- and lyophilized formulations," Carbohydrate Polymers, 2021, 264:118011, 8 pages.
Fda.gov [online]. "Remdesivir by Gilead Sciences: FDA Warns of Newly Discovered Potential Drug Interaction That May Reduce Effectiveness of Treatment." Jun. 15, 2020, retrieved on Sep. 2, 2022, retrieved from URL <https://www.fda.gov/safety/medical-product-safety-information/remdesivir-gilead-sciences-fda-warns-newly-discovered-potential-drug-interaction-may-reduce, 2 pages.
Rebeaud et al., "SARS-CoV-2 and the Use of Chloroquine as an Antiviral Treatment," Frontiers in Medicine, Apr. 24, 2020, 7:184, 6 pages.
Taiwanese Office Action in TW Appln. No. 110119391. dated Aug. 22, 2022, 17 pages (with English translation).
Wang et al., "Remdesivir in adults with severe COVID-19: a randomised, double-blind, placebo-controlled, multicentre trial," Lancet, Apr. 29, 2020, 395:1569-1578.

REMDESIVIR TREATMENT METHODS

CROSS-REFERENCES TO RELATED APPLICATIONS

This application is a continuation of U.S. Ser. No. 17/333,389, filed May 28, 2021, which claims priority to the U.S. Provisional Patent Application No. 63/032,321, filed May 29, 2020, which is incorporated herein in its entirety for all purposes.

BACKGROUND

Preventing or treating some Arenaviridae, Coronaviridae, Filoviridae, Flaviviridae, Orthomyxovirus, Pneumoviridae, and Paramyxoviridae viral infections present challenges due to a lack of vaccine or post-exposure treatment modality for preventing or managing infections caused by viruses from these families. In some cases, patients only receive supportive therapy such as electrolyte and fluid balancing, oxygen, blood pressure maintenance, or treatment for secondary infections.

The compound (S)-2-ethylbutyl 2-(((S)-(2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy) phosphoryl)amino)propanoate, referred to herein as the compound of Formula Ia, is known to exhibit antiviral properties against several viral families, including Arenaviridae, Coronaviridae, Filoviridae, Paramyxoviridae, and Flaviviridae viruses (see e.g. Warren, T. et al., *Nature* (2016) 531:381-385; Lo M K, et al. *Sci. Reports* 2017; 7:43395; Sheahan T P, et al. *Sci. Transl. Med.* 2017; 9:eaal3653; Agostini M L, et al. *MBio* 2018; 9 (2):e00221-18; *Cell Research* (2020) 30:269-271, and WO 2017/184668). There is a need to develop methods of treating viral infections comprising the compound of Formula Ia, or a pharmaceutically acceptable salt thereof.

Methods of treating a viral infection comprising the compound of Formula Ia, or a pharmaceutically acceptable salt thereof, in a human in need thereof should avoid other agents that decrease, retard, or attenuate the antiviral activity of the compound.

BRIEF SUMMARY

In some embodiments, the present disclosure provides a method of treating a viral infection in a human in need thereof, the method comprising administering to the human a therapeutically effective amount of a compound of Formula I, Formula Ia, or Formula Ib, or a pharmaceutically acceptable salt thereof:

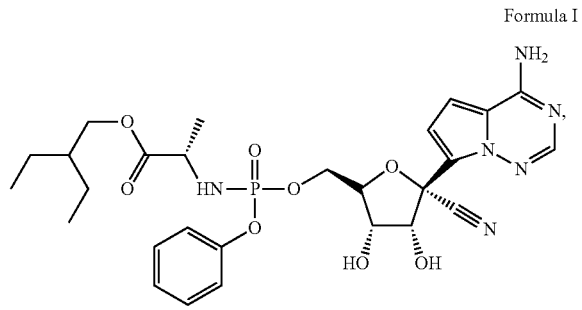

Formula I

Formula Ia

Formula Ib wherein the human is not being treated with chloroquine, or an analog or salt thereof, thereby treating the viral infection.

In some embodiments, the present disclosure provides a method of optimizing a plasma or blood concentration of a compound of Formula II, or a pharmaceutically acceptable salt thereof, in a human in need thereof:

Formula II the method comprising administering to the human an antiviral compound, wherein the human has not been administered chloroquine, or an analog or salt thereof, the antiviral compound is converted to the compound of Formula II upon administration to the human, and the plasma or blood concentration of the compound of Formula II is optimized in the absence of chloroquine, or an analog or salt thereof.

In some embodiments, the present disclosure provides a method of optimizing a plasma or blood concentration of a compound of Formula II, or a pharmaceutically acceptable salt thereof, in a human in need thereof, the method comprising: (a) administering to the human a compound of Formula I, Formula Ia, or Formula Ib, or a pharmaceutically acceptable salt thereof, (b) measuring the plasma or blood concentration of the compound of Formula II in the human; and (c) adjusting any remaining doses of the compound of Formula I, Formula Ia, or Formula Ib, to optimize the plasma or blood concentration of the compound of Formula II in the human.

In some embodiments, the present disclosure provides a method of determining a delivery dose of a compound of Formula I, Formula Ia, or Formula Ib, or a pharmaceutically acceptable salt thereof, for treating a viral infection in a human in need thereof, the method comprising: (a) providing an original dose of the compound of Formula I, Formula Ia, or Formula Ib, or a pharmaceutically acceptable salt thereof, (b) determining whether the human has been administered chloroquine, or an analog or salt thereof; and (c1) if the human has been administered chloroquine, or an analog or salt thereof, increasing the original dose of the compound of Formula I, Formula Ia, or Formula Ib, or a pharmaceutically acceptable salt thereof, to determine the delivery dose, or (c2) if the human has not been administered chloroquine, or an analog or salt thereof, selecting the original dose of the compound of Formula I, Formula Ia, or Formula Ib, or a pharmaceutically acceptable salt thereof, as the delivery dose.

In some embodiments, the present disclosure provides a method of forming a compound of Formula II in a human in need thereof, comprising administering to the human a therapeutically effective amount of a compound of Formula Ia, and instructing the human not to take chloroquine, or an analog or salt thereof, wherein the compound of Formula Ia is metabolized to the compound of Formula II in the absence of chloroquine, or an analog or salt thereof, wherein the compound of Formula II has the structure:

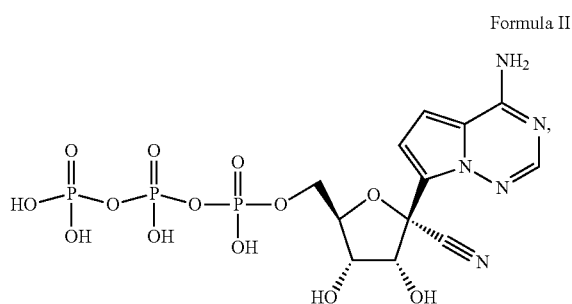 [SMILES: N#C[C@@]1(c2ccc3c(N)ncnn23)O[C@H](COP(=O)(O)OP(=O)(O)OP(=O)(O)O)[C@@H](O)[C@H]1O]

Formula II and
wherein the compound of Formula Ia has the structure:

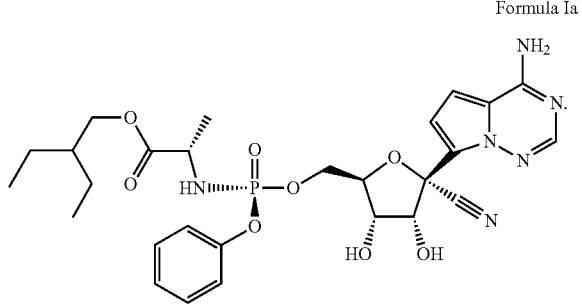 [SMILES: CCC(CC)COC(=O)[C@H](C)N[P@](=O)(OC[C@H]1O[C@@](C#N)(c2ccc3c(N)ncnn23)[C@H](O)[C@@H]1O)Oc1ccccc1]

Formula Ia

In some embodiments, the present disclosure provides is a method of reducing the risk of decreased efficacy of the compound of Formula Ia, or a pharmaceutically acceptable salt thereof, in a human suffering from a viral infection, the method comprising:
(a) determining if the human has taken chloroquine, or an analog or salt thereof, prior to administration of the compound of Formula Ia, or a pharmaceutically acceptable salt thereof, (b) instructing the human not to take chloroquine, or an analog or salt thereof, while being treated with the compound of Formula Ia, or a pharmaceutically acceptable salt thereof, and (c) administering the compound of Formula Ia, or a pharmaceutically acceptable salt thereof, to the human, thereby reducing the risk of decreased efficacy of the compound of Formula Ia, or a pharmaceutically acceptable salt thereof.

In some embodiments, the present disclosure provides a method of preventing a contraindication in a human suffering from a viral infection, the method comprising: (a) determining if the human has taken chloroquine, or an analog or salt thereof, prior to administration of the compound of Formula Ia, or a pharmaceutically acceptable salt thereof, (b) instructing the human not to take chloroquine, or an analog or salt thereof, while being treated with the compound of Formula Ia, or a pharmaceutically acceptable salt thereof, and (c) administering the compound of Formula Ia, or a pharmaceutically acceptable salt thereof, to the human, thereby preventing a contraindication in the human.

In some embodiments, the present disclosure provides a method of maintaining efficacy of a compound of Formula Ia, or a pharmaceutically acceptable salt thereof, in a human suffering from a viral infection, the method comprising: (a) determining if the human has taken chloroquine, or an analog or salt thereof, prior to administration of the compound of Formula Ia, or a pharmaceutically acceptable salt thereof, (b) instructing the human not to take chloroquine, or an analog or salt thereof, while being treated with the compound of Formula Ia, or a pharmaceutically acceptable salt thereof, and (c) administering the compound of Formula Ia, or a pharmaceutically acceptable salt thereof, to the human, thereby maintaining efficacy of the compound of Formula Ia, or a pharmaceutically acceptable salt thereof.

In some embodiments, the present disclosure provides a method of reducing the risk of a reduced plasma concentration of a compound of Formula II, in a human suffering from a viral infection, the method comprising: (a) determining if the human has taken chloroquine, or an analog or salt thereof, prior to administration of the compound of Formula Ia, or a pharmaceutically acceptable salt thereof, (b) instructing the human not to take chloroquine, or an analog or salt thereof, while being treated with the compound of Formula Ia, or a pharmaceutically acceptable salt thereof, and (c) administering the compound of Formula Ia, or a pharmaceutically acceptable salt thereof, to the human, thereby reducing the risk of a reduced plasma concentration of the compound of Formula II.

DETAILED DESCRIPTION

I. General

Figure 1:
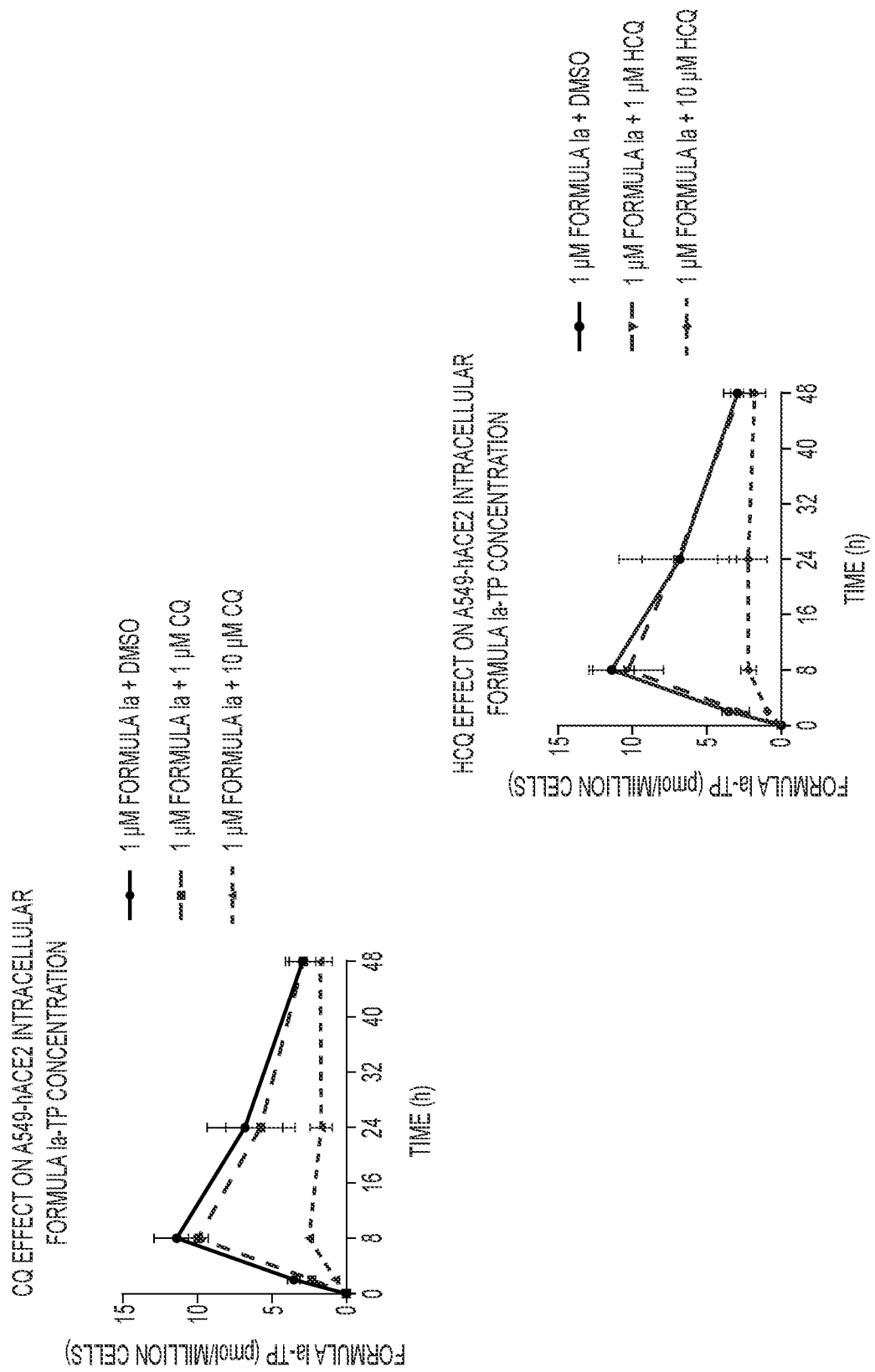
FIG. 1. Shows the effect of chloroquine (CQ) or hydroxychloroquine (HCQ) on the Formula Ia triphosphate (TP) formation in A549-hACE2 cells.

The present disclosure provides a method of treating a viral infection in a subject, comprising administering to the subject a compound of Formula I, Formula Ia, or Formula Ib, or a pharmaceutically acceptable salt thereof, wherein the subject is not being treated with chloroquine, or an analog or salt thereof.

II. Definitions

A "compound of the disclosure" refers to a compound that is administered to a subject in a method as described herein, and includes compounds of Formula I, Formula Ia, Formula Ib, or a pharmaceutically acceptable salt thereof.

"Pharmaceutically acceptable" or "physiologically acceptable" refer to compounds, salts, compositions, dosage forms and other materials which are useful in preparing a pharmaceutical composition that is suitable for veterinary or human pharmaceutical use.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutical composition" refers to a formulation of a compound of the disclosure and a medium generally accepted in the art for the delivery of the biologically active compound to mammals, for example, humans. Such a medium includes all pharmaceutically acceptable excipients therefor.

"Effective amount" or "therapeutically effective amount" refers to an amount of a compound of the disclosure, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound of the disclosure which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the disclosure, and the age, body weight, general health, sex and diet of the patient. Such a therapeutically effective amount can be determined routinely by one of ordinary skill in the art having regard to their own knowledge, the state of the art, and this disclosure.

"Treatment" or "treating" or "treat" refers to an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compositions may, in some embodiments, be administered to a subject (including a human) who is at risk or has a family history of the disease or condition.

"Subject" or "patient" refer to an animal, such as a mammal, including a human, that has been or will be the object of treatment, observation or experiment. The methods described herein may be useful in human therapy and/or veterinary applications. In some embodiments, the subject or the patient is a mammal. In some embodiments, the subject or the patient is human; a domestic animal like a dog or a cat; a farm animal such as a cow, horse, sheep, goat or pig; or a laboratory animal such as a mouse, rat, hamster, guinea pig, pig, rabbit, dog, or monkey. In some embodiments, the subject or the patient is a human.

"Human in need thereof" refers to a human who may have or is suspected to have diseases or conditions that would benefit from certain treatment; for example, being treated with the compounds disclosed herein according to the present application to treat a viral infection.

III. Methods of Use

The present disclosure also provides a method of treating or preventing a viral infection in a human in need thereof, comprising administering a compound described herein.

In some embodiments, the present disclosure provides a method of treating a viral infection in a human in need thereof, the method comprising administering to the human a therapeutically effective amount of a compound of Formula I, Formula Ia, or Formula Ib, or a pharmaceutically acceptable salt thereof:

Formula I

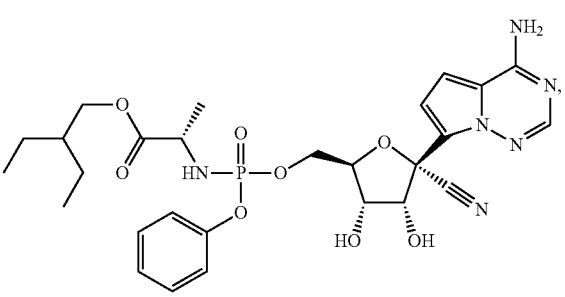

Formula Ia

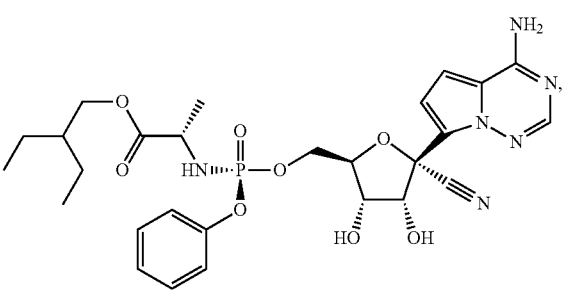

Formula Ib

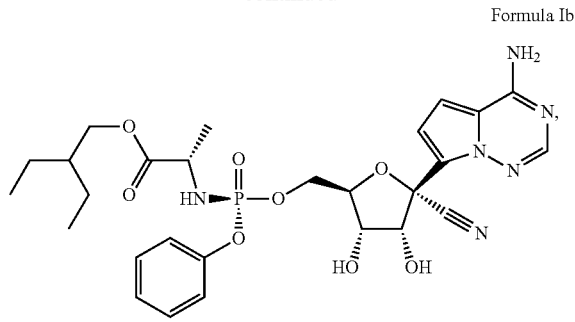

wherein the human is not being treated with chloroquine, or an analog or salt thereof, thereby treating the viral infection.

In some embodiments, the present disclosure provides a method of confirming the administration of the compound of Formula I, Formula Ia, or Formula Ib to a human, comprising identifying a compound of Formula II, or a salt thereof, in a biological sample obtained from the human. In some embodiments, the human is not being treated with chloroquine, or an analog or salt thereof. In some embodiments, the human has not been previously treated with chloroquine, or an analog or salt thereof, before the administering of the compound of Formula I, Formula Ia, or Formula Ib, or a pharmaceutically acceptable salt thereof. In some embodiments, the biological sample is derived from plasma or blood.

In some embodiments, the present disclosure provides a method of measuring the rate of metabolism of the compound of Formula I, Formula Ia, or Formula Ib in a human, comprising measuring the amount of a compound of Formula II, or a salt thereof, in the human at one or more time points after administration of compound of Formula I, Formula Ia, or Formula Ib, or a pharmaceutically acceptable salt thereof. In some embodiments, the human has not been previously treated with chloroquine, or an analog or salt thereof, before the administering of the compound of Formula I, Formula Ia, or Formula Ib, or a pharmaceutically acceptable salt thereof. In some embodiments, the amount of the compound of Formula II, or a salt thereof, is measured from a biological sample obtained from the human. In some embodiments, the amount of the compound of Formula II, or a salt thereof, is measured from a blood sample. In some embodiments, the amount of the compound of Formula II, or a salt thereof, is measured from a plasma sample.

In some embodiments, the present disclosure provides a method of determining the prophylactic or therapeutic response of a human in the treatment of a viral infection comprising measuring the amount of a compound of Formula II, or a salt thereof, in the human at one or more time points after administration of a compound of Formula I, Formula Ia, or Formula Ib, or a pharmaceutically acceptable salt thereof. In some embodiments, the human has not been previously treated with chloroquine, or an analog or salt thereof, before the administering of the compound of Formula I, Formula Ia, or Formula Ib, or a pharmaceutically acceptable salt thereof. In some embodiments, the amount of the compound of Formula II, or a salt thereof, is measured from a biological sample obtained from the human. In some embodiments, the amount of the compound of Formula II, or a salt thereof, is measured from a blood sample. In some embodiments, the amount of the compound of Formula II, or a salt thereof, is measured from a plasma sample.

A. Chloroquine Administration

The present methods provide treatment of a human that does not have an appreciable systemic concentration of chloroquine, or an analog or salt thereof. In some embodiments, the human in need thereof has not been previously treated with chloroquine, or an analog or salt thereof, before the administering of the compound of Formula I, Formula Ia, or Formula Ib, or a pharmaceutically acceptable salt thereof.

In some embodiments, the human has been previously treated with chloroquine, or an analog or salt thereof. In some embodiments, the human in need thereof has not been treated with chloroquine, or an analog or salt thereof, for a period of time before the administering of the compound of Formula I, Formula Ia, or Formula Ib, or a pharmaceutically acceptable salt thereof. In some embodiments, the period of time between the treatment with chloroquine, or an analog or salt thereof, and the administration of the compound of the disclosure allows for a decrease in the systemic concentration of the chloroquine, or an analog or salt thereof, such that the antiviral activity of the compound of the disclosure is not decreased. For example, the period of time between the treatment with chloroquine, or an analog or salt thereof, and the administration of the compound of the disclosure can allow for a decrease in the plasma concentration of the chloroquine, or an analog or salt thereof, as a result of clearance or metabolism.

In some embodiments, the period of time between the treatment with chloroquine, or an analog or salt thereof, and the administration of the compound of the disclosure is at least 1 day, 2 days, 3 days, 4 days, 5 days, 6 days, 7 days, 8 days, 9 days, 10 days, 14 days, 21 days, 28 days, 30 days, 45 days, 60 days, 75 days, 90 days, 120 days, 150 days, 180 days, 210 days, 240 days, 270 days, 300 days, 330 days, or 365 days. In some embodiments, the period of time between the treatment with chloroquine, or an analog or salt thereof, and the administration of the compound of the disclosure is at least 14 days. In some embodiments, the period of time between the treatment with chloroquine, or an analog or salt thereof, and the administration of the compound of the disclosure is at least 28 days. In some embodiments, the period of time between the treatment with chloroquine, or an analog or salt thereof, and the administration of the compound of the disclosure is at least 40 days. In some embodiments, the period of time between the treatment with chloroquine or analog thereof and the administration of the compound of the disclosure is at least 50 days. In some embodiments, the period of time between the treatment with chloroquine, or an analog or salt thereof, and the administration of the compound of the disclosure is at least 60 days. In some embodiments, the period of time between the treatment with chloroquine, or an analog or salt thereof, and the administration of the compound of the disclosure is at least 90 days. In some embodiments, the period of time between the treatment with chloroquine, or an analog or salt thereof, and the administration of the compound of the disclosure is at least 120 days. In some embodiments, the period of time between the treatment with chloroquine, or an analog or salt thereof, and the administration of the compound of the disclosure is at least 180 days. In some embodiments, the period of time between the treatment with chloroquine, or an analog or salt thereof, and the administration of the compound of the disclosure is at least 365 days.

In some embodiments, the period of time between the treatment with chloroquine, or an analog or salt thereof, and the administration of the compound of the disclosure is at least 30 mins, at least 1 hour, at least 2 hours, at least 3 hours, at least 4 hours, at least 6 hours, at least 8 hours, at least 10 hours, at least 12 hours, at least 14 hours, at least 16 hours, at least 20 hours, or at least 24 hours.

In some embodiments, the human has been administered chloroquine, or an analog or salt thereof, in from about 1 days to about 365 days prior to receiving a first dose of the compound of Formula I, Formula Ia, or Formula Ib, or a pharmaceutically acceptable salt thereof, or from about 1 day to about 14 days, from about 1 day to about 21 days, from about 1 day to about 30 days, from about 1 day to about 45 days, from about 10 days to about 45 days, from about 14 days to about 45 days, from about 21 days to about 45 days, from about 28 days to about 45 days, from about 30 days to about 45 days, 10 days to about 60 days, from about 14 days to about 60 days, from about 21 days to about 60 days, from about 28 days to about 60 days, from about 30 days to about 60 days, from about 40 days to about 60 days, from about 10 days to about 90 days, from about 14 days to about 90 days, from about 21 days to about 90 days, from about 28 days to about 90 days, from about 30 days to about 90 days, from about 40 days to about 90 days, from about 10 days to about 365 days, from about 14 days to about 365 days, from about 21 days to about 365 days, from about 28 days to about 365 days, from about 30 days to about 365 days, or from about 60 days to about 365 days, prior to receiving a first dose of the compound of Formula I, Formula Ia, or Formula Ib, or a pharmaceutically acceptable salt thereof. In some embodiments, the human has been administered chloroquine, or an analog or salt thereof, in from about 30 days to about 60 days prior to receiving a first dose of the compound of Formula I, Formula Ia, or Formula Ib, or a pharmaceutically acceptable salt thereof. In some embodiments, the human has been administered chloroquine, or an analog or salt thereof, in from about 21 days to about 45 days prior to receiving a first dose of the compound of Formula I, Formula Ia, or Formula Ib, or a pharmaceutically acceptable salt thereof.

In some embodiments, the human has not been administered chloroquine, or an analog or salt thereof, within 30 minutes, 1 hour, 2 hours, 3 hours, 4 hours, 5 hours, 6 hours, 8 hours, 10 hours, 12 hours, 16 hours, or 20 hours of receiving a first dose of the compound of Formula I, Formula Ia, or Formula Ib, or a pharmaceutically acceptable salt thereof. In some embodiments, the human has not been administered chloroquine, or an analog or salt thereof, within 1 day, 2 days, 3 days, 4 days, 5 days, 6 days, 7 days, 8 days, 9 days, 10 days, 14 days, 21 days, 28 days, 30 days, 45 days, 60 days, 75 days, 90 days, 120 days, 150 days, 180 days, 210 days, 240 days, 270 days, 300 days, 330 days, or 365 days of receiving a first dose of the compound of Formula I, Formula Ia, or Formula Ib, or a pharmaceutically acceptable salt thereof.

In some embodiments, the human has not been administered chloroquine, or an analog or salt thereof, within 1 day of receiving a first dose of the compound of Formula I, Formula Ia, or Formula Ib, or a pharmaceutically acceptable salt thereof. In some embodiments, the human has not been administered chloroquine, or an analog or salt thereof, within 2 days of receiving a first dose of the compound of Formula I, Formula Ia, or Formula Ib, or a pharmaceutically acceptable salt thereof. In some embodiments, the human has not been administered chloroquine, or an analog or salt thereof, within 5 days of receiving a first dose of the compound of Formula I, Formula Ia, or Formula Ib, or a pharmaceutically acceptable salt thereof. In some embodiments, the human has not been administered chloroquine, or an analog or salt thereof, within 7 days of receiving a first dose of the compound of Formula I, Formula Ia, or Formula Ib, or a pharmaceutically acceptable salt thereof. In some embodiments, the human has not been administered chloroquine, or an analog or salt thereof, within 10 days of receiving the first dose of the compound of Formula I, Formula Ia, or Formula Ib, or a pharmaceutically acceptable salt thereof. In some embodiments, the human has not been administered chloroquine, or an analog or salt thereof, within 90 days of receiving the first dose of the compound of Formula I, Formula Ia, or Formula Ib, or a pharmaceutically acceptable salt thereof. In some embodiments, the human has not been administered chloroquine, or an analog or salt thereof, within 365 days of receiving the first dose of the compound of Formula I, Formula Ia, or Formula Ib, or a pharmaceutically acceptable salt thereof.

In some embodiments, the method further comprises instructing the human not to take chloroquine, or an analog or salt thereof, during the treatment of the viral infection.

In some embodiments, the method further comprises instructing the human to wait from about 1 day to about 365 days after taking chloroquine, or an analog or salt thereof, before administering the compound of Formula I, Formula Ia or Formula Ib, or pharmaceutically acceptable salt thereof, or from about 1 day to about 4 days, from about 1 day to about 7 days, from about 1 day to about 10 days, from about 1 day to about 14 days, from about 10 days to about 45 days, from about 14 days to about 45 days, from about 21 days to about 45 days, from about 28 days to about 45 days, from about 30 days to about 45 days, 10 days to about 60 days, from about 14 days to about 60 days, from about 21 days to about 60 days, from about 28 days to about 60 days, from about 30 days to about 60 days, from about 40 days to about 60 days, from about 10 days to about 90 days, from about 14 days to about 90 days, from about 21 days to about 90 days, from about 28 days to about 90 days, from about 30 days to about 90 days, from about 40 days to about 90 days, from about 10 days to about 365 days, from about 14 days to about 365 days, from about 21 days to about 365 days, from about 28 days to about 365 days, from about 30 days to about 365 days, or from about 60 days to about 365 days, after taking chloroquine, or an analog or salt thereof, before administering the compound of Formula I, Formula Ia or Formula Ib, or pharmaceutically acceptable salt thereof.

In some embodiments, the method further comprises instructing the human to wait after taking chloroquine, or an analog or salt thereof, before administering the compound of Formula I, Formula Ia or Formula Ib, or pharmaceutically acceptable salt thereof. In some embodiments, the method further comprises instructing the human to wait at least 1 day, 2 days, 3 days, 4 days, 5 days, 6 days, 7 days, 8 days, 9 days, 10 days, 14 days, 21 days, 28 days, 30 days, 45 days, 60 days, 75 days, 90 days, 120 days, 150 days, 180 days, 210 days, 240 days, 270 days, 300 days, 330 days, or 365 days after taking chloroquine, or an analog or salt thereof, before administering the compound of Formula I, Formula Ia or Formula Ib, or pharmaceutically acceptable salt thereof.

In some embodiments, the method further comprises instructing the human to wait from about 30 mins to about one day after taking chloroquine, or an analog or salt thereof, before administering the compound of Formula I, Formula Ia or Formula Ib, or pharmaceutically acceptable salt thereof. For example to wait for at least 30 mins, at least 1 hour, at least 2 hours, at least 3 hours, at least 4 hours, at least 6 hours, at least 8 hours, at least 10 hours, at least 12 hours, at least 14 hours, at least 16 hours, at least 20 hours, or at least 24 hours before administering the compound of Formula I, Formula Ia or Formula Ib, or pharmaceutically acceptable salt thereof.

In some embodiments, the method further comprises instructing the human to wait after taking chloroquine, or an analog or salt thereof, before administering the compound of Formula Ia, or pharmaceutically acceptable salt thereof. In some embodiments, the method further comprises instructing the human to wait at least 1 day, 2 days, 3 days, 4 days, 5 days, 6 days, 7 days, 8 days, 9 days, 10 days, 14 days, 21 days, 28 days, 30 days, 45 days, 60 days, 75 days, 90 days, 120 days, 150 days, 180 days, 210 days, 240 days, 270 days, 300 days, 330 days, or 365 days after taking chloroquine, or an analog or salt thereof, before administering the compound of Formula Ia, or pharmaceutically acceptable salt thereof.

In some embodiments, the method further comprises instructing the human to wait from about 30 mins to about one day after taking chloroquine, or an analog or salt thereof, before administering the compound of Formula Ia, or pharmaceutically acceptable salt thereof. For example to wait for at least 30 mins, at least 1 hour, at least 2 hours, at least 3 hours, at least 4 hours, at least 6 hours, at least 8 hours, at least 10 hours, at least 12 hours, at least 14 hours, at least 16 hours, at least 20 hours, or at least 24 hours before administering the compound of Formula Ia, or pharmaceutically acceptable salt thereof.

In some embodiments, the human is not administered chloroquine, or an analog or salt thereof, during the treatment of the viral infection. In some embodiments, the method further comprises instructing the human to not administer chloroquine, or an analog or salt thereof, during the treatment of the viral infection.

In some embodiments, the method comprises administering to the human a therapeutically effective amount of a compound of Formula I, Formula Ia, or Formula Ib, or a pharmaceutically acceptable salt thereof, provided the human has not been administered chloroquine, or an analog or salt thereof, prior to the start of treatment, thereby treating the viral infection. In some embodiments, the human has not been administered chloroquine, or an analog or salt thereof, for at least 1 day, 2 days, 3 days, 4 days, 5 days, 6 days, 7 days, 8 days, 9 days, 10 days, 14 days, 21 days, 28 days, 30 days, 45 days, 60 days, 90 days, 120 days, 150 days, 180 days, 210 days, 240 days, 270 days, 300 days, 330 days, or 365 days prior to the start of treatment. In some embodiments, the human has not been administered chloroquine, or an analog or salt thereof, for at least 1 day prior to the start of treatment. In some embodiments, the human has not been administered chloroquine, or an analog or salt thereof, for at least 10 days prior to the start of treatment. In some embodiments, the human has not been administered chloroquine, or an analog or salt thereof, for at least 30 mins, at least 1 hour, at least 2 hours, at least 3 hours, at least 4 hours, at least 6 hours, at least 8 hours, at least 10 hours, at least 12 hours, at least 14 hours, at least 16 hours, at least 20 hours, or at least 24 hours prior to the start of treatment.

Various techniques can be used to determine whether or not a human in need thereof has previously taken chloroquine, or an analog or salt thereof. Non-limiting techniques include self-reporting, interviewing the human, reviewing the human's medical records, or measuring the level of chloroquine, or a metabolite, analog or salt thereof, in the plasma or blood in the human.

The human in need of treatment for a viral infection may also be evaluated for plasma or blood concentration of the chloroquine, or an analog or salt thereof, prior to administration of the compound of the disclosure, such as a compound of Formula I, Formula Ia, or Formula Ib, or a pharmaceutically acceptable salt thereof. In some embodiments, a human in need of treatment for a viral infection has a plasma or blood concentration measured prior to administration of the compound of the disclosure.

Concentrations of chloroquine, or an analog or salt thereof, in human plasma or blood can be measured by any method known in the art. See, for example, Walker, O. et al. *British Journal Clinical Pharmacology* (1983), vol. 16, pages 701-705; Kaewkhao, K. et al. *Bioanalysis* (2019), vol. 11 (5), pages 333-347; Durcan, L. et al. *Journal of Rheumatology* (2015), vol. 42 (11), pages 2092-2097; Munster, T. et al. *Arthritis Rheumatology* (2002), vol. 46 (6), pages 1460-1469.

In some embodiments, the human has a plasma or blood concentration of the chloroquine, or an analog or salt thereof, of from about 0.1 ng/mL to about 5000 ng/mL at the time a first dose of the compound of Formula I, Formula Ia, or Formula Ib, or a pharmaceutically acceptable salt thereof, is administered to the human, or from about 0.1 ng/mL to about 4000 ng/mL, from about 0.1 ng/mL to about 3000 ng/mL, from about 0.1 ng/mL to about 2000 ng/mL, from about 0.1 ng/mL to about 1000 ng/mL, from about 0.1 ng/mL to about 500 ng/mL, from about 0.1 ng/mL to about 400 ng/mL, from about 0.1 ng/mL to about 300 ng/mL, from about 0.1 ng/mL to about 200 ng/mL, from about 0.1 ng/mL to about 100 ng/mL, from about 0.1 ng/mL to about 80 ng/mL, from about 0.1 ng/mL to about 60 ng/mL, from about 0.1 ng/mL to about 50 ng/mL, from about 0.1 ng/mL to about 40 ng/mL, from about 0.1 ng/mL to about 30 ng/mL, from about 0.1 ng/mL to about 20 ng/mL, or from about 0.1 ng/mL to about 10 ng/mL, from about 5 ng/mL to about 4000 ng/mL, from about 5 ng/mL to about 3000 ng/mL, from about 5 ng/mL to about 2000 ng/mL, from about 5 ng/mL to about 1000 ng/mL, from about 5 ng/mL to about 500 ng/mL, from about 5 ng/mL to about 400 ng/mL, from about 5 ng/mL to about 300 ng/mL, from about 5 ng/mL to about 200 ng/mL, from about 5 ng/mL to about 100 ng/mL, from about 5 ng/mL to about 80 ng/mL, from about 5 ng/mL to about 60 ng/mL, from about 5 ng/mL to about 50 ng/mL, from about 5 ng/mL to about 40 ng/mL, from about 5 ng/mL to about 30 ng/mL, from about 5 ng/mL to about 20 ng/mL, or from about 5 ng/mL to about 10 ng/mL, at the time a first dose of the compound of Formula I, Formula Ia, or Formula Ib, or a pharmaceutically acceptable salt thereof, is administered to the human. In some embodiments, the human has a plasma or blood concentration of the chloroquine, or an analog or salt thereof, of from about 0.1 ng/mL to about 50 ng/mL, at the time a first dose of the compound of the disclosure is administered to the human.

In some embodiments, the human has a plasma or blood concentration of the chloroquine, or an analog or salt thereof, of less than 5000 ng/mL at the time a first dose of the compound of Formula I, Formula Ia, or Formula Ib, or a pharmaceutically acceptable salt thereof, is administered to the human, or less than 4000 ng/mL, 3000 ng/mL, 2000 ng/mL, 1000 ng/mL, 500 ng/mL, 400 ng/mL, 300 ng/mL, 200 ng/mL, 100 ng/mL, 80 ng/mL, 60 ng/mL, 50 ng/mL, 45 ng/mL, 40 ng/mL, 35 ng/mL, 30 ng/mL, 25 ng/mL, 20 ng/mL, 15 ng/mL, 10 ng/mL, or 5 ng/mL at the time a first dose of the compound of the disclosure is administered to the human.

In some embodiments, the human has a plasma or blood concentration of the chloroquine, or an analog or salt thereof, of less than 50 ng/mL at the time a first dose of the compound of Formula I, Formula Ia, or Formula Ib, or a pharmaceutically acceptable salt thereof, is administered to the human.

"Chloroquine, or an analog or salt thereof" refers to chloroquine (also known as CQ, N'-(7-chloroquinolin-4-yl)-N,N-diethyl-pentane-1,4-diamine and CAS Number 54-05-7), hydroxychloroquine (also known as HCQ, 2-[{4-[(7-chloroquinolin-4-yl)amino]pentyl}(ethyl)amino]ethanol and CAS Number 118-42-3), and metabolites thereof in the plasma after administration to a human. Members include chloroquine, desethylchloroquine (also known as DCQ, 4-N-(7-chloroquinolin-4-yl)-1-N-ethylpentane-1,4-diamine and CAS Number 1476-52-4), hydroxychloroquine, desethylhydroxychloroquine (also known as DHCQ, cletoquine, 2-[4-[(7-chloroquinolin-4-yl)amino]pentylamino]ethanol, and CAS Number 4298-15-1), and bidesethylhydroxychloroquine (also known as BDCQ), or a pharmaceutically acceptable salt thereof. Illustrative examples include chloroquine, or a pharmaceutically acceptable salt thereof. An example is chloroquine phosphate, commercially available as Aralen®. Chloroquine has the chemical structure:

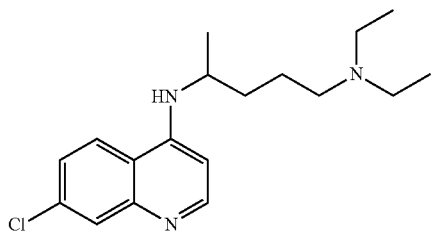

An alternative example includes hydroxychloroquine, or a pharmaceutically acceptable salt thereof. An example is hydroxychloroquine sulfate, commercially available as Plaquenil®. Hydroxychloroquine has the chemical structure:

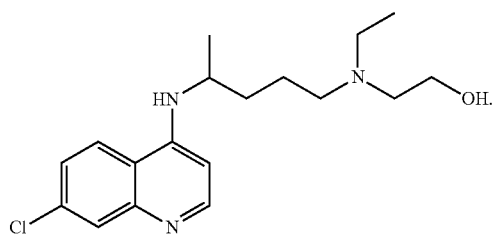 [SMILES: CCN(CCO)CCCC(C)Nc1ccnc2cc(Cl)ccc12]

In some embodiments, the chloroquine, or an analog or salt thereof, is chloroquine, desethylchloroquine, hydroxychloroquine, desethylhydroxychloroquine, or bidesethylhydroxychloroquine, or a pharmaceutically acceptable salt thereof. In some embodiments, the chloroquine, or an analog or salt thereof, is chloroquine, hydroxychloroquine, or a pharmaceutically acceptable salt thereof. In some embodiments, the chloroquine, or an analog or salt thereof, is chloroquine, or a pharmaceutically acceptable salt thereof. For example, the chloroquine, or an analog or salt thereof, can be chloroquine phosphate. In some embodiments, the chloroquine, or an analog or salt thereof, is hydroxychloroquine, or a pharmaceutically acceptable salt thereof. For example, the chloroquine, or an analog or salt thereof, can be hydroxychloroquine sulfate.

B. Compounds

The present disclosure includes use of antiviral compounds that when administered to a human in need thereof produce the compound of Formula II, or a pharmaceutically acceptable salt thereof.

The present disclosure also includes use of compounds of Formula I, Formula Ia and Formula Ib, or a pharmaceutically acceptable salt thereof.

The compound of Formula I was described in WO2012/012776. The IUPAC name for the compound of Formula I is 2-ethylbutyl (((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)-L-alaninate. The compound of Formula I, or a pharmaceutically acceptable salt thereof, has the structure:

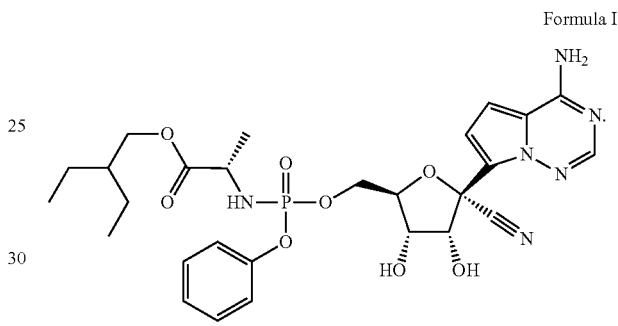

Formula I

The compound of Formula Ia was described in WO2016/069826. The IUPAC name for the compound of Formula Ia is (S)-2-ethylbutyl 2-(((S)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate, and the CAS Registry Number is 1809249-37-3. The compound of Formula Ia is also referred to as remdesivir and GS-5734. The compound of Formula Ia, or a pharmaceutically acceptable salt thereof, has the structure:

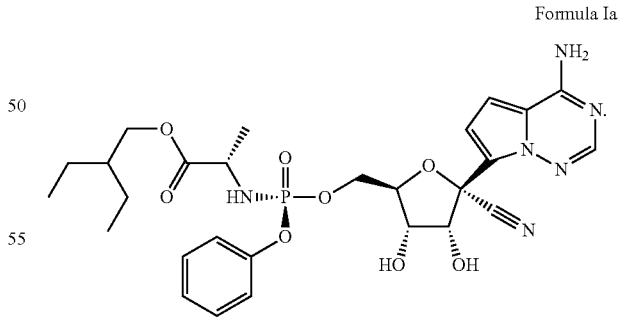

Formula Ia

The compound of Formula Ib was described in WO2016/069826. The IUPAC name for the compound of Formula Ib is (S)-2-ethylbutyl 2-(((R)-(((2R,3S,4R,5R)-5-(4-aminopyrrolo[2,1-f][1,2,4]triazin-7-yl)-5-cyano-3,4-dihydroxytetrahydrofuran-2-yl)methoxy)(phenoxy)phosphoryl)amino)propanoate. The compound of Formula Ib, or a pharmaceutically acceptable salt thereof, has the structure:

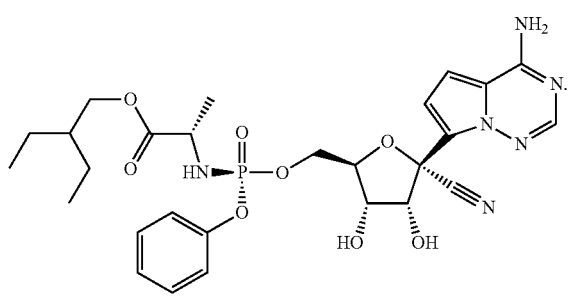

Formula Ib

In some embodiments, administering a compound of Formula I, Formula Ia, or Formula Ib, or a pharmaceutically acceptable salt thereof, to a human in need thereof produces a compound of Formula II or a pharmaceutically acceptable salt thereof:

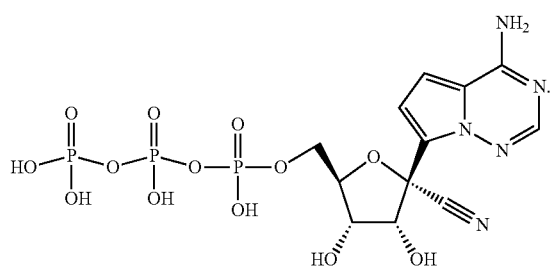

Formula II

The compound of Formula I, Formula Ia, or Formula Ib can be used in any suitable form. For example, the compound of Formula I, Formula Ia, or Formula Ib can be amorphous or crystalline. In some embodiments, the compound of Formula I, Formula Ia, or Formula Ib is amorphous. In some embodiments, the compound of Formula I, Formula Ia, or Formula Ib is crystalline.

Crystalline forms of the compound of Formula Ia useful in the methods and compositions of the present disclosure are described in U.S. Patent Application Publication No. 2018/0346504. For example, the compound of Formula Ia can be crystalline Form I, Form II, Form III, or Form IV as described in U.S. Patent Application Publication No. 20180346504, or a combination thereof. In some embodiments, the compound of Formula Ia is crystalline.

The compounds of Formula I, Formula Ia and Formula Ib, or a pharmaceutically acceptable salt thereof, can be combined with one or more pharmaceutically acceptable excipients. In some embodiments, the pharmaceutically acceptable excipient comprises an aqueous vehicle. In some embodiments, the pharmaceutical compositions provided herein comprise the compound of Formula I, or a pharmaceutically acceptable salt thereof, and an aqueous vehicle. In some embodiments, the pharmaceutical compositions provided herein comprise the compound of Formula Ia, or a pharmaceutically acceptable salt thereof, and an aqueous vehicle. In some embodiments, the pharmaceutical compositions provided herein comprise the compound of Formula Ib, or a pharmaceutically acceptable salt thereof, and an aqueous vehicle. The aqueous vehicle comprises water and optionally one or more components selected from a co-solvent, a surfactant, a suspending agent, a tonicity agent, a buffer, a cyclodextrin, and an anti-microbial agent or preservative. Exemplary formulations may be found in U.S. Patent Application Publication No. 2019/0083525.

In some embodiments, the method of treating the viral infection in the human in need thereof comprises administering to the human the compound of Formula I, or a pharmaceutically acceptable salt thereof:

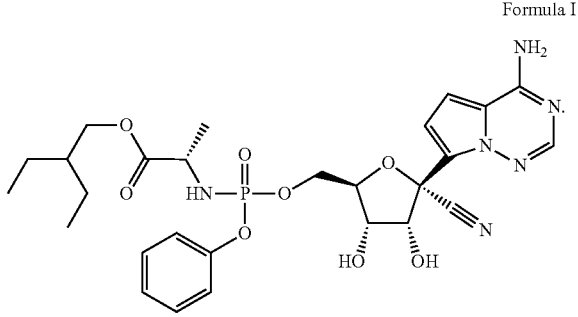 [SMILES: CCC(CC)COC(=O)[C@H](C)NP(=O)(OC[C@H]1O[C@@](C#N)(c2ccc3c(N)ncnn23)[C@H](O)[C@@H]1O)Oc1ccccc1]

Formula I

In some embodiments, the method comprises administering the compound of Formula I.

In some embodiments, the method of treating the viral infection in the human in need thereof, comprises administering to the human a compound of Formula Ia, or a pharmaceutically acceptable salt thereof:

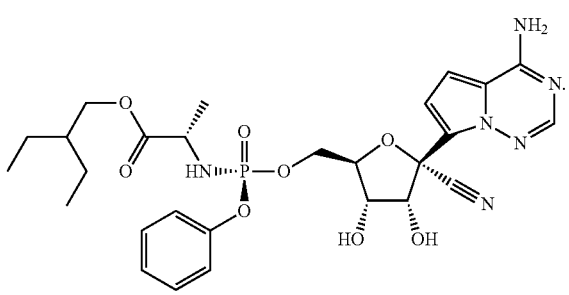

Formula Ia

In some embodiments, the method comprises administering the compound of Formula Ia.

In some embodiments, the method of treating the viral infection in the human in need thereof comprises administering to the human a compound of Formula Ib, or a pharmaceutically acceptable salt thereof:

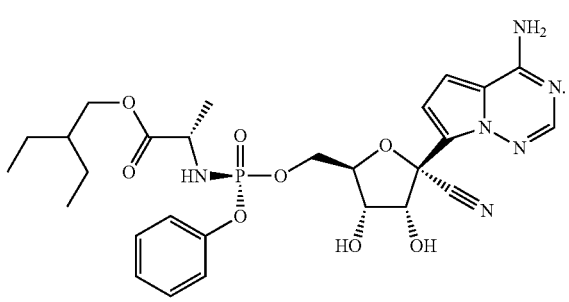

Formula Ib

In some embodiments, the method comprises administering the compound of Formula Ib.

The compound of the disclosure can be administered by any route appropriate to the condition to be treated. Suitable routes include oral, rectal, nasal (including inhalation), pulmonary, topical (including buccal and sublingual), vaginal and parenteral (including subcutaneous, intramuscular, intravenous, intradermal, intrathecal and epidural), implants, and the like. It will be appreciated that the preferred route may vary, for example, with the condition of the human.

In some embodiments, the compound of Formula I, Formula Ia, or Formula Ib, or a pharmaceutically acceptable salt thereof, is administered by inhalation or intravenously. In some embodiments, the compound of Formula I, Formula Ia, or Formula Ib, or a pharmaceutically acceptable salt thereof, is administered intravenously. In some embodiments, the compound of Formula I, Formula Ia, or Formula Ib, or a pharmaceutically acceptable salt thereof, is administered by inhalation.

In some embodiments, the compound of Formula I, Formula Ia, or Formula Ib, or a pharmaceutically acceptable salt thereof, is administered once daily or twice daily. In some embodiments, the compound of Formula I, Formula Ia, or Formula Ib, or a pharmaceutically acceptable salt thereof, is administered once daily.

In some embodiments, the human weighs at least 40 kg, and the compound of Formula I, Formula Ia, or Formula Ib, or a pharmaceutically acceptable salt thereof, is administered in the first dose of 150-250 mg on day 1, and administered in a second dose of 50-150 mg on each of the following 4 days. In some embodiments, the second dose of 50-150 mg is administered for an additional 1 to 5 days. In some embodiments, the human weighs at least 40 kg, and the compound of Formula I, Formula Ia, or Formula Ib, or a pharmaceutically acceptable salt thereof, is administered in the first dose of 150-250 mg on day 1, and administered in a second dose of 50-150 mg on each of the following 4, 5, 6, 7, 8, or 9 days. In some embodiments, the human weighs at least 40 kg, and the compound of Formula I, Formula Ia, or Formula Ib, or a pharmaceutically acceptable salt thereof, is administered in the first dose of 150-250 mg on day 1, and administered in a second dose of 50-150 mg on each of the following 9 days. In some embodiments, the compound of Formula I, Formula Ia, or Formula Ib, or a pharmaceutically acceptable salt thereof, is administered once daily. In some embodiments, the compound of Formula I, Formula Ia, or Formula Ib, or a pharmaceutically acceptable salt thereof, is administered over from about 30 to about 120 minutes.

In some embodiments, the human weighs at least 40 kg, and the compound of Formula I, Formula Ia, or Formula Ib, or a pharmaceutically acceptable salt thereof, is administered intravenously in the first dose of 200 mg on day 1, and administered intravenously in a second dose of 100 mg on each of the following 4 days. In some embodiments, the second dose of 100 mg is administered for an additional 1 to 5 days. In some embodiments, the human weighs at least 40 kg, and the compound of Formula I, Formula Ia, or Formula Ib, or a pharmaceutically acceptable salt thereof, is administered intravenously in the first dose of 200 mg on day 1, and administered intravenously in a second dose of 100 mg on each of the following 4, 5, 6, 7, 8, or 9 days. In some embodiments, the human weighs at least 40 kg, and the compound of Formula I, Formula Ia, or Formula Ib, or a pharmaceutically acceptable salt thereof, is administered intravenously in the first dose of 200 mg on day 1, and administered intravenously in a second dose of 100 mg on each of the following 9 days. In some embodiments, the compound of Formula I, Formula Ia, or Formula Ib, or a pharmaceutically acceptable salt thereof, is administered intravenously once daily. In some embodiments, the compound of Formula I, Formula Ia, or Formula Ib, or a pharmaceutically acceptable salt thereof, is administered intravenously over from about 30 to about 120 minutes.

In some embodiments, the human weighs at least 40 kg, and the compound of Formula Ia, or a pharmaceutically acceptable salt thereof, is administered in the first dose of 150-250 mg on day 1, and administered in a second dose of 50-150 mg on each of the following 4 days. In some embodiments, the second dose of 50-150 mg is administered for an additional 1 to 5 days. In some embodiments, the human weighs at least 40 kg, and the compound of Formula Ia, or a pharmaceutically acceptable salt thereof, is administered in the first dose of 150-250 mg on day 1, and administered in a second dose of 50-150 mg on each of the following 4, 5, 6, 7, 8, or 9 days. In some embodiments, the human weighs at least 40 kg, and the compound of Formula Ia, or a pharmaceutically acceptable salt thereof, is administered in the first dose of 150-250 mg on day 1, and administered in a second dose of 50-150 mg on each of the following 9 days. In some embodiments, the compound of Formula Ia, or a pharmaceutically acceptable salt thereof, is administered once daily. In some embodiments, the compound of Formula Ia, or a pharmaceutically acceptable salt thereof, is administered over from about 30 to about 120 minutes.

In some embodiments, the human weighs at least 40 kg, and the compound of Formula Ia, or a pharmaceutically acceptable salt thereof, is administered intravenously in the first dose of 200 mg on day 1, and administered intravenously in a second dose of 100 mg on each of the following 4 days. In some embodiments, the second dose of 100 mg is administered for an additional 1 to 5 days. In some embodiments, the human weighs at least 40 kg, and the compound of Formula Ia, or a pharmaceutically acceptable salt thereof, is administered intravenously in the first dose of 200 mg on day 1, and administered intravenously in a second dose of 100 mg on each of the following 4, 5, 6, 7, 8, or 9 days. In some embodiments, the human weighs at least 40 kg, and the compound of Formula Ia, or a pharmaceutically acceptable salt thereof, is administered intravenously in the first dose of 200 mg on day 1, and administered intravenously in a second dose of 100 mg on each of the following 9 days. In some embodiments, the compound of Formula Ia, or a pharmaceutically acceptable salt thereof, is administered intravenously once daily. In some embodiments, the compound of Formula Ia, or a pharmaceutically acceptable salt thereof, is administered intravenously over from about 30 to about 120 minutes.

In some embodiments, the human weighs from 3.5 kg to less than 40 kg, and the compound of Formula I, Formula Ia, or Formula Ib, or a pharmaceutically acceptable salt thereof, is administered in the first dose of 2.5-10 mg/kg on day 1, and administered in a second dose of 1-5 mg/kg on each of the following 4 days. In some embodiments, the second dose of 1-5 mg/kg is administered for an additional 1 to 5 days. In some embodiments the human weighs from 3.5 kg to less than 40 kg, and the compound of Formula I, Formula Ia, or Formula Ib, or a pharmaceutically acceptable salt thereof, is administered in the first dose of 2.5-10 mg/kg on day 1, and administered in a second dose of 1-5 mg/kg on each of the following 4, 5, 6, 7, 8, or 9 days. In some embodiments the human weighs from 3.5 kg to less than 40 kg, and the compound of Formula I, Formula Ia, or Formula Ib, or a pharmaceutically acceptable salt thereof, is administered in the first dose of 2.5-10 mg/kg on day 1, and administered in a second dose of 1-5 mg/kg on each of the following 9 days.

In some embodiments, the compound of Formula I, Formula Ia, or Formula Ib, or a pharmaceutically acceptable salt thereof, is administered once daily. In some embodiments, the compound of Formula I, Formula Ia, or Formula Ib, or a pharmaceutically acceptable salt thereof, is administered over from about 30 to about 120 minutes.

In some embodiments, the human weighs from 3.5 kg to less than 40 kg, and the compound of Formula I, Formula Ia, or Formula Ib, or a pharmaceutically acceptable salt thereof, is administered intravenously in the first dose of 5 mg/kg on day 1, and administered intravenously in a second dose of 2.5 mg/kg on each of the following 4 days. In some embodiments, the second dose of 2.5 mg/kg is administered for an additional 1 to 5 days. In some embodiments the human weighs from 3.5 kg to less than 40 kg, and the compound of Formula I, Formula Ia, or Formula Ib, or a pharmaceutically acceptable salt thereof, is administered intravenously in the first dose of 5 mg/kg on day 1, and administered intravenously in a second dose of 2.5 mg/kg on each of the following 4, 5, 6, 7, 8, or 9 days. In some embodiments the human weighs from 3.5 kg to less than 40 kg, and the compound of Formula I, Formula Ia, or Formula Ib, or a pharmaceutically acceptable salt thereof, is administered intravenously in the first dose of 5 mg/kg on day 1, and administered intravenously in a second dose of 2.5 mg/kg on each of the following 9 days. In some embodiments, the compound of Formula I, Formula Ia, or Formula Ib, or a pharmaceutically acceptable salt thereof, is administered intravenously once daily. In some embodiments, the compound of Formula I, Formula Ia, or Formula Ib, or a pharmaceutically acceptable salt thereof, is administered intravenously over from about 30 to about 120 minutes.

In some embodiments, the human weighs from 3.5 kg to less than 40 kg, and the compound of Formula Ia, or a pharmaceutically acceptable salt thereof, is administered in the first dose of 2.5-10 mg/kg on day 1, and administered in a second dose of 1-5 mg/kg on each of the following 4 days. In some embodiments, the second dose of 1-5 mg/kg is administered for an additional 1 to 5 days. In some embodiments the human weighs from 3.5 kg to less than 40 kg, and the compound of Formula Ia, or a pharmaceutically acceptable salt thereof, is administered in the first dose of 2.5-10 mg/kg on day 1, and administered in a second dose of 1-5 mg/kg on each of the following 4, 5, 6, 7, 8, or 9 days. In some embodiments the human weighs from 3.5 kg to less than 40 kg, and the compound of Formula Ia, or a pharmaceutically acceptable salt thereof, is administered in the first dose of 2.5-10 mg/kg on day 1, and administered in a second dose of 1-5 mg/kg on each of the following 9 days. In some embodiments, the compound of Formula Ia, or a pharmaceutically acceptable salt thereof, is administered once daily. In some embodiments, the compound of Formula Ia, or a pharmaceutically acceptable salt thereof, is administered over from about 30 to about 120 minutes.

In some embodiments, the human weighs from 3.5 kg to less than 40 kg, and the compound of Formula Ia, or a pharmaceutically acceptable salt thereof, is administered intravenously in the first dose of 5 mg/kg on day 1, and administered intravenously in a second dose of 2.5 mg/kg on each of the following 4 days. In some embodiments, the second dose of 2.5 mg/kg is administered for an additional 1 to 5 days. In some embodiments, the human weighs from 3.5 kg to less than 40 kg, and the compound of Formula Ia, or a pharmaceutically acceptable salt thereof, is administered intravenously in the first dose of 5 mg/kg on day 1, and administered intravenously in a second dose of 2.5 mg/kg on each of the following 4, 5, 6, 7, 8, or 9 days. In some embodiments, the human weighs from 3.5 kg to less than 40 kg, and the compound of Formula Ia, or a pharmaceutically acceptable salt thereof, is administered intravenously in the first dose of 5 mg/kg on day 1, and administered intravenously in a second dose of 2.5 mg/kg on each of the following 9 days. In some embodiments, the compound of Formula Ia, or a pharmaceutically acceptable salt thereof, is administered intravenously once daily. In some embodiments, the compound of Formula Ia, or a pharmaceutically acceptable salt thereof, is administered intravenously over from about 30 to about 120 minutes.

C. Viral Infections

Any suitable viral infection can be treated by the method of the present disclosure. In some embodiments, the viral infection is caused by a virus selected from the group consisting of Arenaviridae, Coronaviridae, Filoviridae, Flaviviridae, Pneumoviridae, and Paramyxoviridae.

In some embodiments, the viral infection is caused by an Arenaviridae virus. In some embodiments, the method of treating an Arenaviridae virus infection comprises administering a compound of the disclosure, such as a compound of Formula I, Formula Ia, or Formula Ib, or pharmaceutically acceptable salt thereof. In some embodiments, the method comprises treating an Arenaviridae virus infection selected from the group consisting of Allpahuayo virus (ALLV), Amapari virus (AMAV), Bear Canyon virus (BCNV), Catarina virus, Chapare virus, Cupixi virus (CPXV), Dandenong virus, Flexal virus (FLEV), Guanarito virus (GTOV), Ippy virus (IPPYV), Junin virus (JUNV), Kodoko virus, Lassa virus (LASV), Latino virus (LATV), Lymphocytic choriomeningitis virus (LCMV), Lujo virus, Machupo virus (MACV), Mobala virus (MOBV), Morogoro virus, Mopeia virus (MOPV), Oliveros virus (OLVV), Parana virus (PARV), Pichinde virus (PICV), Pinhal virus, Pirital virus (PIRV), Sabia virus (SABV), Skinner Tank virus, Tacaribe virus (TCRV), Tamiami virus (TAMV), and Whitewater Arroyo virus (WWAV) by administering a compound of the disclosure provided herein. In some embodiments, the Arenaviridae virus is Lassa or Junin. In some embodiments, the method comprises treating a Lassa virus infection by administering a compound of the disclosure provided herein. In some embodiments, the method comprises treating a Junin virus infection by administering a compound of the disclosure provided herein.

In some embodiments, the viral infection is caused by a Coronaviridae virus. In some embodiments, the method of treating a Coronaviridae virus infection comprises administering a compound of the disclosure, such as a compound of Formula I, Formula Ia, or Formula Ib, or pharmaceutically acceptable salt thereof. In some embodiments, the Coronaviridae virus infection is selected from the group consisting of a Severe Acute Respiratory Syndrome (SARS) infection, SARS-CoV-2 (also known as 2019-nCov and COVID-19) infection, Middle Eastern Respiratory Syndrome (MERS) infection, other human coronavirus (229E, NL63, 0C43, HKU1, or WW1) infections, or a zoonotic coronavirus (PEDV or HKU CoV isolates such as HKU3, HKU5, or HKU9) infection. In some embodiments, the Coronaviridae virus is SARS, SARS-CoV-2, or MERS. In some embodiments, the Coronaviridae virus is SARS. In some embodiments, the Coronaviridae virus is SARS-CoV-2. In some embodiments, the Coronaviridae virus is MERS. In some embodiments, the viral infection is caused by a virus having at least 70% sequence homology a viral polymerase selected from SARS-CoV polymerase, SARS-CoV-2 polymerase, and MERS polymerase. In some embodiments, the viral infection is caused by a virus having at least 80% sequence homology a viral polymerase selected from SARS-CoV polymerase, SARS-CoV-2 polymerase, and MERS polymerase. In some embodiments, the viral infection is caused by a virus having at least 90% sequence homology a viral polymerase selected from SARS-CoV polymerase, SARS-CoV-2 polymerase, and MERS polymerase. In some embodiments, the viral infection is caused by a virus having at least 95% sequence homology a viral polymerase selected from SARS-CoV polymerase, SARS-CoV-2 polymerase, and MERS polymerase. In some embodiments, the viral infection is caused by a virus having at least 97% sequence homology a viral polymerase selected from SARS-CoV polymerase, SARS-CoV-2 polymerase, and MERS polymerase. In some embodiments, the viral infection is caused by a virus having at least 99% sequence homology a viral polymerase selected from SARS-CoV polymerase, SARS-CoV-2 polymerase, and MERS polymerase.

In some embodiments, the viral infection is caused by a Filoviridae virus. In some embodiments, the method of treating a Filoviridae virus infection comprises administering a compound of the disclosure, such as a compound of Formula I, Formula Ia, or Formula Ib, or pharmaceutically acceptable salt thereof. In some embodiments, the Filoviridae virus is Ebola or Marburg. In some embodiments, the Filoviridae virus is an Ebola virus. In some embodiments, the Ebola virus is selected from the group consisting of: Zaire (i.e. Ebola virus, EBOV), Sudan, Tai Forest, Bundibugyo, and Reston. In some embodiments, the Filoviridae virus is a Marburg virus.

In some embodiments, the viral infection is caused by a Flaviviridae virus. In some embodiments, the method of treating a Flaviviridae virus infection comprises administering a compound of the disclosure, such as a compound of Formula I, Formula Ia, or Formula Ib, or pharmaceutically acceptable salt thereof. In some embodiments, the Flaviviridae virus is selected from the group consisting of: dengue, yellow fever, West Nile, and Zika. In some embodiments, the method of treating a dengue virus infection comprises administering a compound of the disclosure provided herein. In some embodiments, the Flaviviridae virus is yellow fever. In some embodiments, the method of treating a yellow fever virus infection comprises administering a compound of the disclosure provided herein. In some embodiments, the method of treating a West Nile virus infection comprises administering a compound of the disclosure provided herein. In some embodiments, the method of treating a Zika virus infection comprises administering a compound of the disclosure provided herein. In some embodiments, the method of treating a hepatitis C virus infection comprises administering a compound of the disclosure provided herein.

In some embodiments, the viral infection is caused by a Pneumoviridae virus. In some embodiments, the method of treating a Pneumoviridae virus infection comprises administering a compound of the disclosure, such as a compound of Formula I, Formula Ia, or Formula Ib, or pharmaceutically acceptable salt thereof. In some embodiments, the Pneumoviridae virus is respiratory syncytial virus or human metapneumovirus. In some embodiments, the Pneumoviridae virus is respiratory syncytial virus. In some embodiments, the Pneumoviridae virus is human metapneumovirus.

In some embodiments, the viral infection is caused by a Paramyxoviridae virus. In some embodiments, the method of treating a Paramyxoviridae virus infection comprises administering a compound of the disclosure, such as a compound of Formula I, Formula Ia, or Formula Ib, or pharmaceutically acceptable salt thereof. Paramyxoviridae viruses include, but are not limited to Nipah virus, Hendra virus, measles, mumps, and parainfluenza virus. In some embodiments, the Paramyxoviridae virus is Nipah or parainfluenza virus. In some embodiments, the Paramyxoviridae virus is Nipah. In some embodiments, the Paramyxoviridae virus is parainfluenza.

In some embodiments, the present disclosure provides a compound of the disclosure provided herein, or pharmaceutically acceptable salt thereof, for use in methods of treating an Arenaviridae virus infection. In some embodiments, the present disclosure provides a compound of the disclosure provided herein, or pharmaceutically acceptable salt thereof, for use in methods of treating an Arenaviridae virus infection selected from the group of Allpahuayo virus (ALLV), Amapari virus (AMAV), Bear Canyon virus (BCNV), Catarina virus, Chapare virus, Cupixi virus (CPXV), Dandenong virus, Flexal virus (FLEV), Guanarito virus (GTOV), Ippy virus (IPPYV), Junin virus (JUNV), Kodoko virus, Lassa virus (LASV), Latino virus (LATV), Lymphocytic choriomeningitis virus (LCMV), Lujo virus, Machupo virus (MACV), Mobala virus (MOBV), Morogoro virus, Mopeia virus (MOPV), Oliveros virus (OLVV), Parana virus (PARV), Pichinde virus (PICV), Pinhal virus, Pirital virus (PIRV), Sabia virus (SABV), Skinner Tank virus, Tacaribe virus (TCRV), Tamiami virus (TAMV), and Whitewater Arroyo virus (WWAV) by administering a compound of the disclosure provided herein. In some embodiments, the Arenaviridae virus is Lassa or Junin. In some embodiments, the present disclosure provides a compound of the disclosure provided herein, or pharmaceutically acceptable salt thereof, for use in methods of treating a Lassa virus infection. In some embodiments, the present disclosure provides a compound of the disclosure provided herein, or pharmaceutically acceptable salt thereof, for use in methods of treating a Junin virus infection.

In some embodiments, the present disclosure provides a compound of the disclosure provided herein for use in methods of treating a Coronaviridae virus infection. In some embodiments, the Coronaviridae virus infection is selected from the group consisting of a Severe Acute Respiratory Syndrome (SARS) infection, SARS-CoV-2 (also known as 2019-nCov and COVID-19) infection, Middle Eastern Respiratory Syndrome (MERS) infection, other human coronavirus (229E, NL63, OC43, HKU1, or WW1) infections, or a zoonotic coronavirus (PEDV or HKU CoV isolates such as HKU3, HKU5, or HKU9) infection. In some embodiments, the Coronaviridae virus is SARS, SARS-CoV-2, or MERS. In some embodiments, the Coronaviridae virus is SARS. In some embodiments, the present disclosure provides a compound of the disclosure provided herein for use in methods of treating a Severe Acute Respiratory Syndrome (SARS) infection. In some embodiments, the Coronaviridae virus is SARS-CoV-2. In some embodiments, the present disclosure provides a compound of the disclosure provided herein for use in methods of treating a SARS-nCoV-2 infection. In some embodiments, the Coronaviridae virus is MERS. In some embodiments, the present disclosure provides a compound of the disclosure provided herein for use in methods of treating a Middle East Respiratory Syndrome (MERS) infection.

In some embodiments, the present disclosure provides a compound of the disclosure provided herein, or pharmaceutically acceptable salt thereof, for use in methods of treating a Filoviridae virus infection. In some embodiments, the Filoviridae virus is Ebola or Marburg. In some embodiments, the Filoviridae virus is an Ebola virus. In some embodiments, the present disclosure provides a compound of the disclosure provided herein, or pharmaceutically acceptable salt thereof, for use in methods of treating an Ebola virus infection. In some embodiments, the present disclosure provides a compound of the disclosure provided herein, or pharmaceutically acceptable salt thereof, for use in methods of treating an Ebola virus infection selected from the group consisting of: Zaire (i.e. Ebola virus, EBOV), Sudan, Tai Forest, Bundibugyo, and Reston. In some embodiments, the Filoviridae virus is a Marburg virus. In some embodiments, the present disclosure provides a compound of the disclosure provided herein, or pharmaceutically acceptable salt thereof, for use in methods of treating a Marburg virus infection.

In some embodiments, the present disclosure provides a compound of the disclosure provided herein, or pharmaceutically acceptable salt thereof, for use in methods of treating a Flaviviridae virus infection. In some embodiments, the Flaviviridae virus is selected from the group consisting of: dengue, yellow fever, West Nile, and Zika. In some embodiments, the Flaviviridae virus is dengue virus. In some embodiments, the Flaviviridae virus is yellow fever. In some embodiments, the Flaviviridae virus is West Nile virus. In some embodiments, the Flaviviridae virus is Zika virus. In some embodiments, the Flaviviridae virus is hepatitis C virus.

In some embodiments, the present disclosure provides a compound of the disclosure provided herein, or pharmaceutically acceptable salt thereof, for use in a method of treating a Pneumoviridae virus infection. In some embodiments, the Pneumoviridae virus is respiratory syncytial virus or human metapneumovirus. In some embodiments, the Pneumoviridae virus is a respiratory syncytial virus. In some embodiments, the Pneumoviridae virus is human metapneumovirus.

In some embodiments, the present disclosure provides a compound of the disclosure provided herein, or pharmaceutically acceptable salt thereof, for use in a method of treating a Paramyxoviridae virus infection. Paramyxoviridae viruses include, but are not limited to Nipah virus, Hendra virus, measles, mumps, and parainfluenza virus. In some embodiments, the Paramyxoviridae virus is Nipah or parainfluenza virus. In some embodiments, the Paramyxoviridae virus is Nipah. In some embodiments, the Paramyxoviridae virus is parainfluenza.

In some embodiments, the present disclosure provides the use of a compound of the disclosure provided herein, or pharmaceutically acceptable salt thereof, in the manufacture of a medicament for treating an Arenaviridae virus infection. In some embodiments, the present disclosure provides the use of a compound of the disclosure provided herein, or pharmaceutically acceptable salt thereof, in the manufacture of a medicament for treating an Arenaviridae virus infection selected from the group of: Allpahuayo virus (ALLV), Amapari virus (AMAV), Bear Canyon virus (BCNV), Catarina virus, Chapare virus, Cupixi virus (CPXV), Dandenong virus, Flexal virus (FLEV), Guanarito virus (GTOV), Ippy virus (IPPYV), Junin virus (JUNV), Kodoko virus, Lassa virus (LASV), Latino virus (LATV), Lymphocytic choriomeningitis virus (LCMV), Lujo virus, Machupo virus (MACV), Mobala virus (MOBV), Morogoro virus, Mopeia virus (MOPV), Oliveros virus (OLVV), Parana virus (PARV), Pichinde virus (PICV), Pinhal virus, Pirital virus (PIRV), Sabia virus (SABV), Skinner Tank virus, Tacaribe virus (TCRV), Tamiami virus (TAMV), and Whitewater Arroyo virus (WWAV). In some embodiments, the Arenaviridae virus is Lassa or Junin. In some embodiments, the present disclosure provides the use of a compound of the disclosure provided herein, or pharmaceutically acceptable salt thereof, in the manufacture of a medicament for treating a Lassa virus infection. In some embodiments, the present disclosure provides the use of a compound of the disclosure provided herein, or pharmaceutically acceptable salt thereof, in the manufacture of a medicament for treating a Junin virus infection.

In some embodiments, the present disclosure provides the use of a compound of the disclosure provided herein, or pharmaceutically acceptable salt thereof, in the manufacture of a medicament for treating a Coronaviridae virus infection. In some embodiments, the Coronaviridae virus infection is selected from the group consisting of a Severe Acute Respiratory Syndrome (SARS) infection, SARS-CoV-2 (also known as 2019-nCov and COVID-19) infection, Middle Eastern Respiratory Syndrome (MERS) infection, other human coronavirus (229E, NL63, 0C43, HKU1, or WW1) infections, or a zoonotic coronavirus (PEDV or HKU CoV isolates such as HKU3, HKU5, or HKU9) infection. In some embodiments, the Coronaviridae virus is SARS, SARS-CoV-2, or MERS. In some embodiments, the Coronaviridae virus is SARS. In some embodiments, the present disclosure provides the use of a compound of the disclosure provided herein, or pharmaceutically acceptable salt thereof, in the manufacture of a medicament for treating a SARS infection. In some embodiments, the Coronaviridae virus is SARS-CoV-2. In some embodiments, the present disclosure provides the use of a compound of the disclosure provided herein, or pharmaceutically acceptable salt thereof, in the manufacture of a medicament for treating a SARS-nCoV-2 infection. In some embodiments, the Coronaviridae virus is MERS. In some embodiments, the present disclosure provides the use of a compound of the disclosure provided herein, or pharmaceutically acceptable salt thereof, in the manufacture of a medicament for treating a MERS infection.

In some embodiments, the present disclosure provides the use of a compound of the disclosure provided herein, or pharmaceutically acceptable salt thereof, in the manufacture of a medicament for treating a Filoviridae virus infection. In some embodiments, the Filoviridae virus is Ebola or Marburg. In some embodiments, the Filoviridae virus is an Ebola virus. In some embodiments, the present disclosure provides the use of a compound of the disclosure provided herein, or pharmaceutically acceptable salt thereof, in the manufacture of a medicament for treating an Ebola virus infection. In some embodiments, the present disclosure provides the use of a compound of the disclosure provided herein, or pharmaceutically acceptable salt thereof, in the manufacture of a medicament for treating an Ebola virus infection selected from the group consisting of: Zaire (i.e. Ebola virus, EBOV), Sudan, Taï Forest, Bundibugyo, and Reston. In some embodiments, the present disclosure provides the use of a compound of the disclosure provided herein, or pharmaceutically acceptable salt thereof, in the manufacture of a medicament for treating a Marburg virus infection.

In some embodiments, the present disclosure provides the use of a compound of the disclosure provided herein, or pharmaceutically acceptable salt thereof, in the manufacture of a medicament for treating a Flaviviridae virus infection. In some embodiments, the Flaviviridae virus is selected from the group consisting of: dengue, yellow fever, West Nile, and Zika. In some embodiments, the Flaviviridae virus is dengue virus. In some embodiments, the Flaviviridae virus is yellow fever. In some embodiments, the Flaviviridae virus is West Nile virus. In some embodiments, the Flaviviridae virus is Zika virus. In some embodiments, the Flaviviridae virus is hepatitis C virus.

In some embodiments, the present disclosure provides a compound of the disclosure provided herein, or pharmaceutically acceptable salt thereof, for use in a manufacture of a medicament for treating a Pneumoviridae virus infection. In some embodiments, the Pneumoviridae virus is respiratory syncytial virus or human metapneumovirus. In some embodiments, the Pneumoviridae virus is a respiratory syncytial virus. In some embodiments, the Pneumoviridae virus is human metapneumovirus.

In some embodiments, the present disclosure provides a compound of the disclosure provided herein, or pharmaceutically acceptable salt thereof, for use in a manufacture of a medicament for treating a Paramyxoviridae virus infection. Paramyxoviridae viruses include, but are not limited to Nipah virus, Hendra virus, measles, mumps, and parainfluenza virus. In some embodiments, the Paramyxoviridae virus is Nipah or parainfluenza virus. In some embodiments, the Paramyxoviridae virus is Nipah. In some embodiments, the Paramyxoviridae virus is parainfluenza.

D. Additional Uses

In some embodiments, the present disclosure provides a method of optimizing a plasma or blood concentration of a compound of Formula II, or a pharmaceutically acceptable salt thereof, in a human in need thereof:

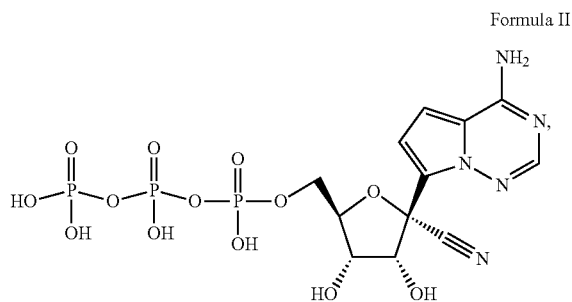 [SMILES: N#C[C@@]1(c2ccc3c(N)ncnn23)O[C@H](COP(=O)(O)OP(=O)(O)OP(=O)(O)O)[C@@H](O)[C@H]1O]

Formula II the method comprising administering to the human an antiviral compound, wherein the human has not been administered chloroquine, or an analog or salt thereof, the antiviral compound is converted to the compound of Formula II upon administration to the human, and the plasma or blood concentration of the compound of Formula II is optimized in the absence of chloroquine, or an analog or salt thereof. In some embodiments, the human has not been administered chloroquine, or an analog or salt thereof, within 1 day of administering to the human an antiviral compound. In some embodiments, the human has not been administered chloroquine, or an analog or salt thereof, within 10 days of administering to the human an antiviral compound.

In some embodiments, the human has not been administered chloroquine, or an analog or salt thereof, within 30 mins, 1 hour, 2 hours, 3 hours, 4 hours, 6 hours, 8 hours, 10 hours, 12 hours, 14 hours, 16 hours, 20 hours, or 24 hours of administering to the human an antiviral compound. In some embodiments, the human has not been administered chloroquine, or an analog or salt thereof, within 1 day, 2 days, 3 days, 4 days, 5 days, 6 days, 7 days, 8 days, 9 days, 10 days, 14 days, 21 days, 28 days, 30 days, 45 days, 60 days, 75 days, 90 days, 120 days, 150 days, 180 days, 210 days, 240 days, 270 days, 300 days, 330 days, or 365 days, of administering to the human an antiviral compound. In some embodiments, the human has a plasma or blood concentration of the chloroquine, or an analog or salt thereof, of less than 50 ng/mL, such as less than 45 ng/mL, 40 ng/mL, 35 ng/mL, 30 ng/mL, 25 ng/mL, 20 ng/mL, 15 ng/mL, 10 ng/mL, or 5 ng/mL, at the time a first dose of the antiviral compound is administered to the human. In some embodiments, the human has a plasma or blood concentration of the chloroquine, or an analog or salt thereof, of less than 50 ng/mL, at the time a first dose of the antiviral compound is administered to the human.

In some embodiments, the antiviral compound is a compound of Formula I, Formula Ia, or Formula Ib, or a pharmaceutically acceptable salt thereof. In some embodiments, the plasma or blood concentration of the compound of Formula II in the human is higher than a second concentration of a compound of Formula II in a reference human treated with chloroquine, or an analog or salt thereof, and the antiviral compound. In some embodiments, the plasma or blood concentration of the compound of Formula II in the human is from about 1.1 times to about 10 times higher, such as from about 1.2 times to about 5 times, from about 1.3 times to about 5 times, from about 1.2 times to about 4 times, from about 1.3 times to about 4 times, from about 1.2 times to about 3 times, from about 1.3 times to about 3 times, from about 1.2 times to about 2 times, or from about 1.3 times to about 2 times, higher than a second concentration of the compound in a reference human treated with chloroquine, or an analog or salt thereof, and the antiviral compound. In some embodiments, the plasma or blood concentration of the compound of Formula II in the human is at least 1.1 times higher, such as at least 1.2 times, 1.3 times, 1.4 times, 1.5 times, 1.6 times, 1.7 times, 1.8 times, 1.9 times, 2 times, 2.1 times, 2.2 times, 2.3 times, 2.4 times, 2.5 times, 2.6 times, 2.7 times, 2.8 times, 2.9 times, 3 times, 3.2 times, 3.5 times, 3.6 times, 3.8 times, 4 times, 4.2 times, 4.4 times, 4.6 times, 4.8 times, 5 times, 6 times, 7 times, 8 times, 9 times, or 10 times higher than a second concentration of the compound in a reference human treated with chloroquine, or an analog or salt thereof, and the antiviral compound.

In some embodiments, the present disclosure provides a method of optimizing a plasma or blood concentration of a compound of Formula II, or a pharmaceutically acceptable salt thereof, in a human in need thereof, comprises: (a) administering to the human a compound of Formula I, Formula Ia, or Formula Ib, or a pharmaceutically acceptable salt thereof (b) measuring the plasma or blood concentration of the compound of Formula II in the human; and (c) adjusting any remaining doses of the compound of Formula I, Formula Ia, or Formula Ib, to optimize the plasma or blood concentration of the compound of Formula II in the human. In some embodiments, the method comprises administering to the human a daily dose. In some embodiments, the method comprises administering to the human 10 daily doses.

In some embodiments, the plasma or blood concentration of the compound of Formula II in the human is from about 1.1 times to about 10 times higher, such as from about 1.2 times to about 5 times, from about 1.3 times to about 5 times, from about 1.2 times to about 4 times, from about 1.3 times to about 4 times, from about 1.2 times to about 3 times, from about 1.3 times to about 3 times, from about 1.2 times to about 2 times, or from about 1.3 times to about 2 times, higher than a second concentration of the compound in a reference human treated with chloroquine, or an analog or salt thereof, and a compound of Formula I, Formula Ia, or Formula Ib, or a pharmaceutically acceptable salt thereof. In some embodiments, the plasma or blood concentration of the compound of Formula II in the human is at least 1.1 times higher, such as at least 1.2 times, 1.3 times, 1.4 times, 1.5 times, 1.6 times, 1.7 times, 1.8 times, 1.9 times, 2 times, 2.1 times, 2.2 times, 2.3 times, 2.4 times, 2.5 times, 2.6 times, 2.7 times, 2.8 times, 2.9 times, 3 times, 3.2 times, 3.5 times, 3.6 times, 3.8 times, 4 times, 4.2 times, 4.4 times, 4.6 times, 4.8 times, 5 times, 6 times, 7 times, 8 times, 9 times, or 10 times higher than a second concentration of the compound in a reference human treated with chloroquine, or an analog or salt thereof, and a compound of Formula I, Formula Ia, or Formula Ib, or a pharmaceutically acceptable salt thereof.

In some embodiments, the present disclosure provides a method of determining a delivery dose of a compound of Formula I, Formula Ia, or Formula Ib, or a pharmaceutically acceptable salt thereof, for treating a viral infection in a human in need thereof, the method comprising: (a) providing an original dose of the compound of Formula I, Formula Ia, or Formula Ib, or a pharmaceutically acceptable salt thereof (b) determining whether the human has been administered chloroquine, or an analog or salt thereof; and (c1) if the human has been administered chloroquine, or an analog or salt thereof, increasing the original dose of the compound of Formula I, Formula Ia, or Formula Ib, or a pharmaceutically acceptable salt thereof, to determine the delivery dose, or (c2) if the human has not been administered chloroquine, or an analog or salt thereof, selecting the original dose of the compound of Formula I, Formula Ia, or Formula Ib, or a pharmaceutically acceptable salt thereof, as the delivery dose.

In some embodiments, the method of determining a delivery dose comprises determining whether the human has been administered chloroquine, or an analog thereof, within 1 day prior to the treatment of the viral infection. In some embodiments, the method comprises determining whether the human has been administered chloroquine, or an analog thereof, within 10 days prior to the treatment of the viral infection. In some embodiments, determining whether the human has been administered chloroquine, or an analog thereof, comprises self-reporting, interviewing the human, reviewing the human's medical records, or measuring the level of chloroquine, or an analog or salt thereof, in the plasma or blood in the human. In some embodiments, the human has not been administered chloroquine, or an analog or salt thereof, within 1 day, 2 days, 3 days, 4 days, 5 days, 6 days, 7 days, 8 days, 9 days, 10 days, 14 days, 21 days, 28 days, 30 days, 45 days, 60 days, 75 days, 90 days, 120 days, 150 days, 180 days, 210 days, 240 days, 270 days, 300 days, 330 days, or 365 days, of administering to the human an antiviral compound.

In some embodiments, the human has not been administered chloroquine, or an analog or salt thereof, within 30 minutes, 1 hour, 2 hours, 3 hours, 4 hours, 5 hours, 6 hours, 8 hours, 10 hours, 12 hours, 16 hours, or 20 hours of receiving a first dose of the compound of Formula I, Formula Ia, or Formula Ib, or a pharmaceutically acceptable salt thereof.

In some embodiments, when the human has been administered chloroquine, or an analog or salt thereof, prior to treating the viral infection, the method comprises increasing the original dose of the compound of Formula I, Formula Ia, or Formula Ib, or pharmaceutically acceptable salt thereof, by from about 1.1 times to about 10 times higher, to determine the delivery dose, or from about 1.2 times to about 5 times, from about 1.3 times to about 5 times, from about 1.2 times to about 4 times, from about 1.3 times to about 4 times, from about 1.2 times to about 3 times, from about 1.3 times to about 3 times, from about 1.2 times to about 2 times, or from about 1.3 times to about 2 times, higher to determine the delivery dose. In some embodiments, when the human has been administered chloroquine, or an analog or salt thereof, prior to treating the viral infection, the method comprises increasing the original dose of the compound of Formula I, Formula Ia, or Formula Ib, or pharmaceutically acceptable salt thereof, by at least 1.1 times higher to determine the delivery dose, or at least 1.2 times, 1.3 times, 1.4 times, 1.5 times, 1.6 times, 1.7 times, 1.8 times, 1.9 times, 2 times, 2.1 times, 2.2 times, 2.3 times, 2.4 times, 2.5 times, 2.6 times, 2.7 times, 2.8 times, 2.9 times, 3 times, 3.2 times, 3.5 times, 3.6 times, 3.8 times, 4 times, 4.2 times, 4.4 times, 4.6 times, 4.8 times, 5 times, 6 times, 7 times, 8 times, 9 times, or 10 times higher, to determine the delivery dose. In some embodiments, the human has not been administered chloroquine, or an analog or salt thereof, within 30 minutes, 1 hour, 2 hours, 3 hours, 4 hours, 5 hours, 6 hours, 8 hours, 10 hours, 12 hours, 16 hours, or 20 hours of receiving a first dose of the compound of Formula I, Formula Ia, or Formula Ib, or a pharmaceutically acceptable salt thereof. In some embodiments, the human has not been administered chloroquine, or an analog or salt thereof, within 1 day, 2 days, 3 days, 4 days, 5 days, 6 days, 7 days, 8 days, 9 days, 10 days, 14 days, 21 days, 28 days, 30 days, 45 days, 60 days, 75 days, 90 days, 120 days, 150 days, 180 days, 210 days, 240 days, 270 days, 300 days, 330 days, or 365 days, of administering to the human an antiviral compound.

In some embodiments, the present disclosure provides a method of forming a compound of Formula II in a human in need thereof, comprising administering to the human a therapeutically effective amount of a compound of Formula Ia, and instructing the human not to take chloroquine, or an analog or salt thereof, wherein the compound of Formula Ia is metabolized to the compound of Formula II in the absence of chloroquine, or an analog or salt thereof. In some embodiments, the human has not been administered chloroquine, or an analog or salt thereof, within 30 minutes, 1 hour, 2 hours, 3 hours, 4 hours, 5 hours, 6 hours, 8 hours, 10 hours, 12 hours, 16 hours, or 20 hours of receiving a first dose of the compound of Formula Ia. In some embodiments, the human has not been administered chloroquine, or an analog or salt thereof, within 1 day, 2 days, 3 days, 4 days, 5 days, 6 days, 7 days, 8 days, 9 days, 10 days, 14 days, 21 days, 28 days, 30 days, 45 days, 60 days, 75 days, 90 days, 120 days, 150 days, 180 days, 210 days, 240 days, 270 days, 300 days, 330 days, or 365 days, of administering the compound of Formula Ia. In some embodiments, after instructing the human not to take chloroquine, or an analog or salt thereof, the human waits at least 1 day before administering the compound of Formula Ia.

In some embodiments, the present disclosure provides a method of reducing the risk of decreased efficacy of the compound of Formula Ia, or a pharmaceutically acceptable salt thereof, in a human suffering from a viral infection, comprises: (a) determining if the human has taken chloroquine, or an analog or salt thereof, prior to administration of the compound of Formula Ia, or a pharmaceutically acceptable salt thereof, (b) instructing the human not to take chloroquine, or an analog or salt thereof, while being treated with the compound of Formula Ia, or a pharmaceutically acceptable salt thereof, and (c) administering the compound of Formula Ia, or a pharmaceutically acceptable salt thereof, to the human, thereby reducing the risk of decreased efficacy of the compound of Formula Ia, or a pharmaceutically acceptable salt thereof. In some embodiments, the human has not been administered chloroquine, or an analog or salt thereof, within 30 minutes, 1 hour, 2 hours, 3 hours, 4 hours, 5 hours, 6 hours, 8 hours, 10 hours, 12 hours, 16 hours, or 20 hours of receiving a first dose of the compound of Formula I, Formula Ia, or Formula Ib, or a pharmaceutically acceptable salt thereof. In some embodiments, the human has not been administered chloroquine, or an analog or salt thereof, within 1 day, 2 days, 3 days, 4 days, 5 days, 6 days, 7 days, 8 days, 9 days, 10 days, 14 days, 21 days, 28 days, 30 days, 45 days, 60 days, 75 days, 90 days, 120 days, 150 days, 180 days, 210 days, 240 days, 270 days, 300 days, 330 days, or 365 days, of administering the compound of Formula Ia, or a pharmaceutically acceptable salt thereof. In some embodiments, if the human is determined to have taken chloroquine, or an analog or salt thereof, prior to administration of the compound of Formula Ia, or a pharmaceutically acceptable salt thereof, the human waits at least 1 day before administering the compound of Formula Ia, or pharmaceutically acceptable salt thereof.

For the methods of the present disclosure requiring instructing the human not to take chloroquine, or an analog or salt thereof, while being treated with the compound of Formula Ia, or a pharmaceutically acceptable salt thereof, any number of actions alone or in combination can be taken in the event that the human is administered chloroquine, or an analog or salt thereof, after receiving the instructions and after receiving the compound of Formula Ia, or a pharmaceutically acceptable salt thereof. In some embodiments, the human stops taking chloroquine, or an analog or salt thereof. In some embodiments, the human waits after the last dose of chloroquine, or an analog or salt thereof, for at least 30 minutes, 1 hour, 2 hours, 3 hours, 4 hours, 5 hours, 6 hours, 8 hours, 10 hours, 12 hours, 16 hours, or 20 hours before receiving a first dose of the compound of Formula I, Formula Ia, or Formula Ib, or a pharmaceutically acceptable salt thereof. In some embodiments, the human waits after the last dose of chloroquine, or an analog or salt thereof, for at least 1 day, 2 days, 3 days, 4 days, 5 days, 6 days, 7 days, 8 days, 9 days, 10 days, 14 days, 21 days, 28 days, 30 days, 45 days, 60 days, 75 days, 90 days, 120 days, 150 days, 180 days, 210 days, 240 days, 270 days, 300 days, 330 days, or 365 days before receiving a first dose of the compound of Formula I, Formula Ia, or Formula Ib, or a pharmaceutically acceptable salt thereof. In some embodiments, after instructing the human not to take chloroquine, or an analog or salt thereof, the human waits at least 1 day before administering the compound of Formula Ia, or pharmaceutically acceptable salt thereof. In some embodiments, the human takes an additional 1 dose, 2 doses, 3 doses, 4 doses, 5 doses, 6 doses, 7 doses, 8 doses, 9 doses, or 10 doses of the compound of Formula I, Formula Ia, or Formula Ib, or a pharmaceutically acceptable salt thereof, as compared to a reference human who has not been administered chloroquine, or an analog or salt thereof. In some embodiments, the human takes a higher dose of the compound of Formula I, Formula Ia, or Formula Ib, or a pharmaceutically acceptable salt thereof, as compared to a reference human who has not been administered chloroquine, or an analog or salt thereof, or at least 1.1 times, 1.2 times, 1.3 times, 1.4 times, 1.5 times, 1.6 times, 1.7 times, 1.8 times, 1.9 times, 2 times, 2.1 times, 2.2 times, 2.3 times, 2.4 times, 2.5 times, 2.6 times, 2.7 times, 2.8 times, 2.9 times, 3 times, 3.2 times, 3.5 times, 3.6 times, 3.8 times, 4 times, 4.2 times, 4.4 times, 4.6 times, 4.8 times, 5 times, 6 times, 7 times, 8 times, 9 times, or 10 times higher dose of the compound of Formula I, Formula Ia, or Formula Ib, or a pharmaceutically acceptable salt thereof, as compared to a reference human who has not been administered chloroquine, or an analog or salt thereof.

In some embodiments, the present disclosure provides a method of preventing a contraindication in a human suffering from a viral infection, the method comprising: (a) determining if the human has taken chloroquine, or an analog or salt thereof, prior to administration of the compound of Formula Ia, or a pharmaceutically acceptable salt thereof, (b) instructing the human not to take chloroquine, or an analog or salt thereof, while being treated with the compound of Formula Ia, or a pharmaceutically acceptable salt thereof, and (c) administering the compound of Formula Ia, or a pharmaceutically acceptable salt thereof, to the human, thereby preventing a contraindication in the human. In some embodiments, if the human is determined to have taken chloroquine, or an analog or salt thereof, prior to administration of the compound of Formula Ia, or a pharmaceutically acceptable salt thereof, the human waits at least 1 day before administering the compound of Formula Ia, or pharmaceutically acceptable salt thereof.

In some embodiments, preventing a contraindication in the human is in comparison to a second human who has taken chloroquine, or an analog or salt thereof, prior to the administration of the compound of Formula Ia, or pharmaceutically acceptable salt thereof, or who has not been instructed not to take chloroquine, or an analog or salt thereof. In some embodiments, the second human who has taken chloroquine, or an analog or salt thereof, prior to the administration of the compound of Formula Ia, or pharmaceutically acceptable salt thereof, is more likely than the human to have a contraindication after administration of the compound of Formula Ia or pharmaceutically acceptable salt thereof. In some embodiments, the second human who has not been instructed not to take chloroquine, or an analog or salt thereof, prior to the administration of the compound of Formula Ia, or pharmaceutically acceptable salt thereof, is more likely than the human to have a contraindication after administration of the compound of Formula Ia or pharmaceutically acceptable salt thereof. In some embodiments, the second human is at least 1.1 times, such as 1.2 times, 1.3 times, 1.4 times, 1.5 times, 1.6 times, 1.7 times, 1.8 times, 1.9 times, 2 times, 2.1 times, 2.2 times, 2.3 times, 2.4 times, 2.5 times, 2.6 times, 2.7 times, 2.8 times, 2.9 times, 3 times, 3.2 times, 3.5 times, 3.6 times, 3.8 times, 4 times, 4.2 times, 4.4 times, 4.6 times, 4.8 times, 5 times, 6 times, 7 times, 8 times, 9 times, or 10 times more likely than the human to have a contraindication after administration of the compound of Formula Ia or pharmaceutically acceptable salt thereof.

In some embodiments, the present disclosure provides a method of maintaining efficacy of a compound of Formula Ia, or a pharmaceutically acceptable salt thereof, in a human suffering from a viral infection, the method comprising: (a) determining if the human has taken chloroquine, or an analog or salt thereof, prior to administration of the compound of Formula Ia, or a pharmaceutically acceptable salt thereof, (b) instructing the human not to take chloroquine, or an analog or salt thereof, while being treated with the compound of Formula Ia, or a pharmaceutically acceptable salt thereof, and (c) administering the compound of Formula Ia, or a pharmaceutically acceptable salt thereof, to the human, thereby maintaining efficacy of the compound of Formula Ia, or a pharmaceutically acceptable salt thereof. In some embodiments, maintaining efficacy comprises maintaining a sufficient plasma or blood concentration of the compound of Formula II in the human after administration as compared to a second human that has not taken chloroquine, or an analog or salt thereof, prior to administration of the compound of Formula Ia, or a pharmaceutically acceptable salt thereof. In some embodiments, the plasma or blood concentration of the compound of Formula II in the human after administration is from about 50% to about 100% of a second plasma or blood concentration of the compound of Formula II in a second human that has not taken chloroquine, or an analog or salt thereof, prior to administration of the compound of Formula Ia, or a pharmaceutically acceptable salt thereof, or from about 60% to about 100%, from about 70% to about 100%, from about 80% to about 100%, or from about 90% to about 100%, of a second plasma or blood concentration of the compound of Formula II in a second human that has not taken chloroquine, or an analog or salt thereof, prior to administration of the compound of Formula Ia, or a pharmaceutically acceptable salt thereof. In some embodiments, if the human is determined to have taken chloroquine, or an analog or salt thereof, prior to administration of the compound of Formula Ia, or a pharmaceutically acceptable salt thereof, the human waits at least 1 day before administering the compound of Formula Ia, or pharmaceutically acceptable salt thereof.

In some embodiments, the present disclosure provides a method of reducing the risk of a reduced plasma concentration of a compound of Formula II, in a human suffering from a viral infection, the method comprising: (a) determining if the human has taken chloroquine, or an analog or salt thereof, prior to administration of the compound of Formula Ia, or a pharmaceutically acceptable salt thereof, (b) instructing the human not to take chloroquine, or an analog or salt thereof, while being treated with the compound of Formula Ia, or a pharmaceutically acceptable salt thereof, and (c) administering the compound of Formula Ia, or a pharmaceutically acceptable salt thereof, to the human, thereby reducing the risk of a reduced plasma concentration of the compound of Formula II. In some embodiments, if the human is determined to have taken chloroquine, or an analog or salt thereof, prior to administration of the compound of Formula Ia, or a pharmaceutically acceptable salt thereof, the human waits at least 1 day before administering the compound of Formula Ia, or pharmaceutically acceptable salt thereof.

In some embodiments, reducing the risk of a reduced plasma concentration of a compound of Formula II comprises maintaining a sufficient concentration of the compound of Formula II in the plasma of the human after administration of the compound of Formula Ia, or a pharmaceutically acceptable salt thereof, as compared to a second human that has not taken chloroquine, or an analog or salt thereof, prior to administration of the compound of Formula Ia, or a pharmaceutically acceptable salt thereof. In some embodiments, the plasma concentration of the compound of Formula II in the human after administration is from about 50% to about 100% of a second concentration of the compound of Formula II in a second human that has not taken chloroquine, or an analog or salt thereof, prior to administration of the compound of Formula Ia, or a pharmaceutically acceptable salt thereof, or from about 60% to about 100%, from about 70% to about 100%, from about 80% to about 100%, or from about 90% to about 100%, of a second concentration of the compound of Formula II in a second human that has not taken chloroquine, or an analog or salt thereof, prior to administration of the compound of Formula Ia, or a pharmaceutically acceptable salt thereof.

For the methods of the present disclosure requiring determining if the human has taken chloroquine, or an analog or salt thereof, prior to administration of the compound of Formula Ia, or a pharmaceutically acceptable salt thereof, the determining can be performed by any suitable means. For example, non-limiting techniques include self-reporting, interviewing the human, reviewing the human's medical records, or measuring the level of chloroquine, or an analog or salt thereof, in the plasma or blood in the human. In some embodiments, the determining includes measuring the level of chloroquine, or a metabolite, analog or salt thereof, in the plasma or blood in the human.

IV. Kits

In some embodiments, the present disclosure provides the use of a kit comprising a compound or composition disclosed herein. In some embodiments, the kit further comprises a label and/or instructions for using the compound or pharmaceutical composition in the method of the present disclosure. For instance, in some embodiments, the kit comprises instructing the human not to take chloroquine, or an analog or salt thereof, during the treatment of the viral infection.

In some embodiments, the kit comprises instructing the human to wait after taking chloroquine, or an analog or salt thereof, at least 30 minutes, 1 hour, 2 hours, 3 hours, 4 hours, 5 hours, 6 hours, 8 hours, 10 hours, 12 hours, 16 hours, or 20 hours before administering the compound of Formula I, Formula Ia or Formula Ib, or pharmaceutically acceptable salt thereof. In some embodiments, the kit comprises instructing the human to wait after taking chloroquine, or an analog or salt thereof, such as at least 1 day, 2 days, 3 days, 4 days, 5 days, 6 days, 7 days, 8 days, 9 days, 10 days, 14 days, 21 days, 28 days, 30 days, 45 days, 60 days, 75 days, 90 days, 120 days, 150 days, 180 days, 210 days, 240 days, 270 days, 300 days, 330 days, or 365 days after taking chloroquine, or an analog or salt thereof, before administering the compound of Formula I, Formula Ia or Formula Ib, or pharmaceutically acceptable salt thereof. In some embodiments, the kit comprises instructing the human to wait at least 1 day after taking chloroquine, or an analog or salt thereof, before administering the compound of Formula I, Formula Ia or Formula Ib, or pharmaceutically acceptable salt thereof. In some embodiments, the kit comprises instructing the human to wait at least 10 days after taking chloroquine, or an analog or salt thereof, before administering the compound of Formula I, Formula Ia or Formula Ib, or pharmaceutically acceptable salt thereof. In some embodiments, the kit comprises instructing the human to wait at least 14 days after taking chloroquine, or an analog or salt thereof, before administering the compound of Formula I, Formula Ia or Formula Ib, or pharmaceutically acceptable salt thereof. In some embodiments, the kit comprises instructing the human to wait at least 21 days after taking chloroquine, or an analog or salt thereof, before administering the compound of Formula I, Formula Ia or Formula Ib, or pharmaceutically acceptable salt thereof.

In some embodiments, the kit comprises instructing the human to wait after taking chloroquine, or an analog or salt thereof, at least 30 minutes, 1 hour, 2 hours, 3 hours, 4 hours, 5 hours, 6 hours, 8 hours, 10 hours, 12 hours, 16 hours, or 20 hours before administering the compound of Formula Ia, or pharmaceutically acceptable salt thereof. In some embodiments, the kit comprises instructing the human to wait after taking chloroquine, or an analog or salt thereof, such as at least 1 day, 2 days, 3 days, 4 days, 5 days, 6 days, 7 days, 8 days, 9 days, 10 days, 14 days, 21 days, 28 days, 30 days, 45 days, 60 days, 75 days, 90 days, 120 days, 150 days, 180 days, 210 days, 240 days, 270 days, 300 days, 330 days, or 365 days after taking chloroquine, or an analog or salt thereof, before administering the compound of Formula Ia, or pharmaceutically acceptable salt thereof. In some embodiments, the kit comprises instructing the human to wait at least 10 days after taking chloroquine, or an analog or salt thereof, before administering the compound of Formula Ia, or pharmaceutically acceptable salt thereof. In some embodiments, the kit comprises instructing the human to wait at least 14 days after taking chloroquine, or an analog or salt thereof, before administering the compound of Formula Ia, or pharmaceutically acceptable salt thereof. In some embodiments, the kit comprises instructing the human to wait at least 21 days after taking chloroquine, or an analog or salt thereof, before administering the compound of Formula Ia, or pharmaceutically acceptable salt thereof.

In some embodiments, the kit further comprises a nebulizer. Any suitable nebulizer may be used. In some embodiments, the nebulizer is a glass nebulizer. In some embodiments, the nebulizer is a hand bulb nebulizer. In some embodiments, the nebulizer is a jet nebulizer or a vibrating mesh nebulizer. In some embodiments, the nebulizer is a jet nebulizer (e.g. VixOne™, AeroEclipse®, Pari LC® Plus). In some examples the nebulizer is a vibrating mesh nebulizer (e.g. eFlow® rapid). In some embodiments, the nebulizer is a ultrasonic nebulizer. In some embodiments, the nebulizer is an adaptive aerosol delivery nebulizer. In some embodiments, the nebulizer is a metered dose inhaler (e.g. a metered dose liquid inhaler).

V. Examples

Figure 2:
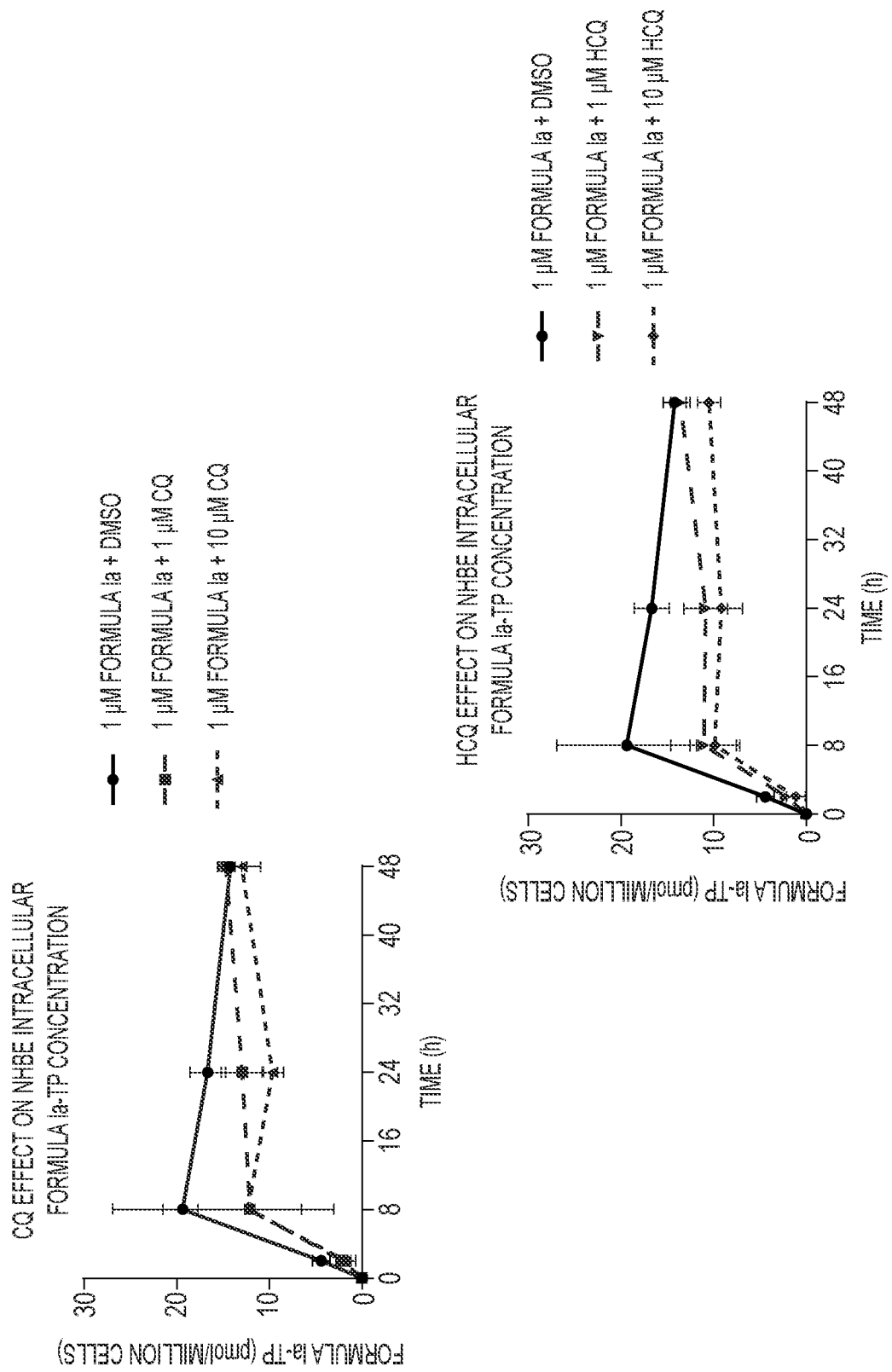
FIG. 2. Shows the effect of CQ or HCQ on the Formula Ia triphosphate (TP) formation in NHBE cultures.
Figure 3:
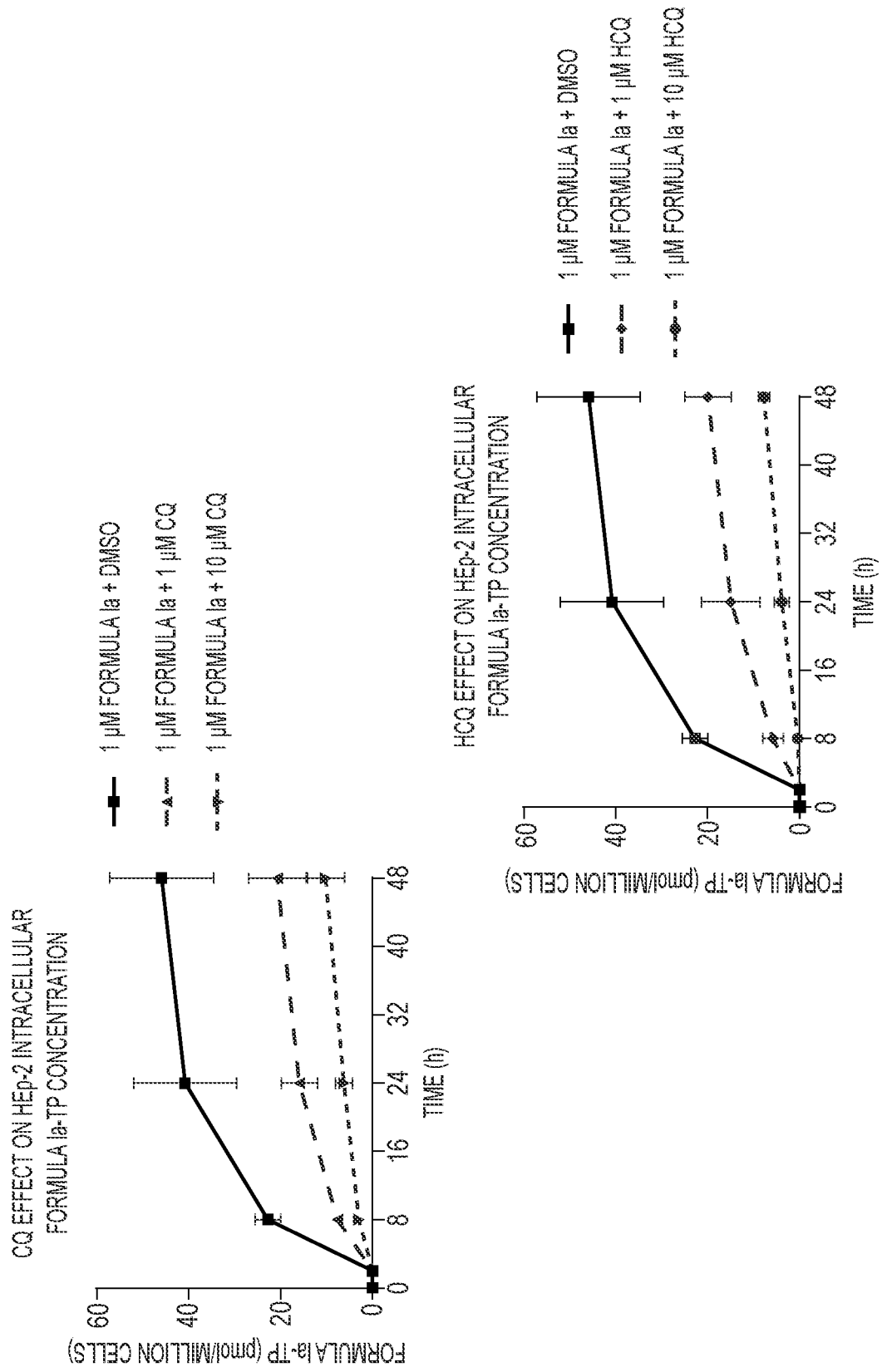
FIG. 3. Shows the effect of CQ or HCQ on the Formula Ia triphosphate (TP) formation in HEp-2 cells.

Example 1. Chloroquine Effect on Compound of Formula Ia in Cells

Antiviral potency of the compound of Formula Ia against respiratory syncytial virus (RSV) was determined in HEp2 cells in the following manner. HEp2 cells (3×103/well) were suspended in DMEM medium+GlutaMAX (supplemented with 10% FBS and 1% Penicillin/Streptomycin) and seeded into 96 well plates. After a 4-hour incubation at 37° C.+5% $CO_2$, three-fold serial dilutions of the compound (final RDV concentration of 9.28 nM to 2000 nM) were added to each well using an HP D300e digital dispenser. To determine the effect of chloroquine (CQ) on Formula Ia antiviral activity, the Formula Ia dilution series was additionally spiked with DMSO or 4× increasing concentrations of CQ (final concentrations: 10 nM, 40 nM, 160 nM, 640 nM, and 2560 nM). The cells were then infected with RSV A2 virus diluted in DMEM medium+GlutaMAX at an MOI=4 and incubated for 4 days at 37° C. and 5% $CO_2$. The final volume in each well was 200 μL. Uninfected and untreated wells were included as controls for 100% cell viability. Following the incubation, 100 μL of culture supernatant was removed from each well and replaced with 100 μL of CellTiter-Glo reagent (Promega). The plates were then rocked for 2 minutes followed by a 10-minute incubation at 25° C. Cell viability was then assessed by measuring luminescence signal using and Envision plate reader. Values were normalized to the uninfected and infected DMSO controls (as 100% and 0% infection, respectively) and data was fit using non-linear regression analysis with the XLfit software. $EC_{50}$ values were determined as the point the non-linear regression curve of 50% infection. The compiled data was generated using three biological replicates each containing technical duplicates for each CQ concentration.

The effect of the combination of the compound of Formula Ia and concentrations of chloroquine (CQ) on RSV replication in HEp2 cells were measured. Results show that CQ antagonizes the anti-RSV activity of the compound of Formula lain a dose-dependent manner as demonstrated by higher Formula Ia $EC_{50}$ values with increasing concentrations of CQ (Table 1).

TABLE 1

Effect of Chloroquine on Anti-RSV Activity of Formula Ia in HEp2 Cells

| Chloroquine (nM) | Formula Ia RSV $EC_{50}$ (nM) | Formula Ia RSV $EC_{50}$ fold change | P value |
|---|---|---|---|
| 0 | 49.5 ± 13.1 | 1 | — |
| 10 | 58.4 ± 12.8 | 1.19 ± 0.10 | 0.075 |
| 40 | 72.1 ± 24.8 | 1.45 ± 0.19 | 0.052 |
| 160 | 99.6 ± 30.3 | 2.02 ± 0.17 | 0.0088 |
| 640 | 138.3 ± 33.8 | 2.86 ± 0.50 | 0.023 |
| 2560 | 209.0 ± 18.2 | 4.43 ± 1.13 | 0.034 |

Example 2: Metabolism Data

A549-hACE2 and NHBE cells were seeded in 6-well plates at $4\times10^5$ and $2.5\times10^5$ cells/well, respectively. HEp-2 cells were seeded in 12-well plates at $2.5\times10^5$ cells/well. Twenty-four hours later, cell culture medium was replaced with medium containing 1 μM Formula Ia alone, or in combination with 1 or 10 μM of either CQ or HCQ, and incubated at 37° C. At 2, 8, 24 and 48 h post drug addition, cells were washed 3 times with ice-cold tris-buffered saline, scraped into 0.5 mL ice-cold 70% methanol and stored at −80° C. Extracts were centrifuged at 15,000 g for 15 minutes and supernatants were transferred to clean tubes for evaporation in a miVac Duo concentrator (Genevac). Dried samples were reconstituted in mobile phase A containing 3 mM ammonium formate (pH 5) with 10 mM dimethylhexylamine (DMHA) in water for analysis by LC-MS/MS, using a multi-stage linear gradient from 10% to 50% acetonitrile in mobile phase A at a flow rate of 360 μL/min. Analytes were separated using a 50×2 mm, 2.5 μm Luna C18(2) HST column (Phenomenex) connected to an LC-20ADXR (Shimadzu) ternary pump system and an HTS PAL autosampler (LEAP Technologies). Detection was performed on a Qtrap (6500+ AB Sciex) mass spectrometer operating in positive ion and multiple reaction monitoring modes. Analytes were quantified using a 7-point standard curve ranging from 0.624 to 160 pmol per million cells prepared in extracts from untreated cells. For normalization by cell number, multiple untreated culture wells were counted at each timepoint.

The metabolism of the compound of Formula Ia to the active triphosphate species (Formula Ia-TP) species was evaluated in A549-hACE2, NHBE, and HEp-2 cell cultures following incubation with the compound of Formula Ia alone and when combined with CQ or HCQ. The concentrations of CQ and HCQ used in these in vitro assays correspond to systemic and lung exposures that result from doses recommended under the former EUA guidance for COVID-19. The average systemic exposures range from 610-760 nM for CQ and approximately 1.7 μM for HCQ, which can achieve lung concentrations in excess of 20 μM for either drug {Salman 2017, Zhao 2014}. In A549-hACE2 cells, co-incubation of the compound of Formula Ia and 1 μM CQ or HCQ did not significantly reduce Formula Ia-TP levels compared to the Formula Ia-TP in the absence of CQ or HCQ; however, incubation at 10 μM of either CQ or HCQ did significantly lower the production of Formula Ia-TP (Table 2; FIG. 1). While Formula Ia-TP levels trended lower in NHBE cultures treated with either concentration of CQ or 1 μM HCQ, these differences were not statistically significant. Conversely, treatment of NHBE cultures with 10 μM HCQ significantly reduced Formula Ia-TP levels (Table 3; FIG. 2). In HEp-2 cervical carcinoma cells, treatment with CQ or HCQ at either 1 or 10 μM showed a dose-dependent reduction in formation of intracellular Formula Ia-TP (Table 4; FIG. 3). Significant CQ or HCQ antagonism of Formula Ia-TP formation in Hep-2 cells was observed at 8 h post treatment and persisted for 48 h. The observed reductions in Formula Ia-TP in the presence of CQ or HCQ indicates a potential antagonistic effect on the compound of Formula Ia metabolism to its active triphosphate.

TABLE 2

Effect of CQ or HCQ on RDV-TP Formation in A549-hACE2 Cells

| | Mean RDV-TP (pmol/million cells)[a] | | | | |
|---|---|---|---|---|---|
| Treatment time (h) | 1 μM Formula Ia | 1 μM Formula Ia + 1 μM CQ | 1 μM Formula Ia + 10 μM CQ | 1 μM Formula Ia + 1 μM HCQ | 1 μM Formula Ia + 10 μM HCQ |
| 2 | 3.6 ± 0.2 | 2.4 ± 0.1 | 0.7 ± 0.1 | 2.8 ± 0.3 | 1.0 ± 0.1 |
| 8 | 11.4 ± 0.8 | 10.0 ± 0.3 | 2.5 ± 0.1 | 10.3 ± 1.2 | 2.2 ± 0.3 |
| 24 | 6.8 ± 1.3 | 5.8 ± 1.2 | 1.7 ± 0.4 | 7.0 ± 2.0 | 2.2 ± 0.6 |
| 48 | 3.0 ± 0.5 | 2.9 ± 0.6 | 1.8 ± 0.4 | 2.8 ± 0.3 | 1.8 ± 0.4 |
| Average Formula Ia-TP concentration (pmol/million cells)[b] | 6.5 ± 0.8 | 5.6 ± 0.8 | 1.8 ± 0.3 | 6.2 ± 1.3 | 2.0 ± 0.4 |
| P value[c] | NA | 0.8497 | 0.0030 | 0.9960 | 0.0041 |

[a]Values are mean ± SEM of duplicate samples collected at each timepoint from two separate experiments.
[b]Average Formula Ia-TP concentration was determined using GraphPad Prism 8.1.2 from the total area under the curve from Formula Ia -TP concentrations detected by LC-MS at 0, 2, 8, 24, and 48 h; and divided by the total time of the assay (48 h).
[c]P value is determined using one-way ANOVA with Dunnett's multiple comparison analysis of Formula Ia + DMSO compared to various concentrations of CQ or HCQ using GraphPad Prism 8.1.2.

TABLE 3

Effect of CQ or HCQ on RDV-TP Formation in NHBE Cultures

| | Mean RDV-TP (pmol/million cells)[a] | | | | |
|---|---|---|---|---|---|
| Treatment time (h) | 1 μM Formula Ia | 1 μM Formula Ia + 1 μM CQ | 1 μM Formula Ia + 10 μM CQ | 1 μM Formula Ia + 1 μM HCQ | 1 μM Formula Ia + 10 μM HCQ |
| 2 | 4.4 ± 0.5 | 2.2 ± 0.2 | 1.8 ± 0.5 | 2.2 ± 0.2 | 1.1 ± 0.5 |
| 8 | 19.4 ± 3.8 | 12.1 ± 2.8 | 12.3 ± 4.6 | 11.1 ± 1.8 | 9.9 ± 1.4 |
| 24 | 16.7 ± 1.0 | 12.9 ± 1.2 | 9.7 ± 0.6 | 10.8 ± 1.2 | 9.2 ± 1.2 |
| 48 | 14.2 ± 0.6 | 14.7 ± 0.5 | 13.0 ± 1.0 | 13.6 ± 0.5 | 10.5 ± 0.6 |
| Average Formula Ia-TP concentration (pmol/million cells)[b] | 15.3 ± 1.5 | 12.0 ± 1.2 | 10.2 ± 1.8 | 10.6 ± 1.0 | 8.8 ± 0.9 |
| P value[c] | NA | 0.2724 | 0.0507 | 0.0753 | 0.0112 |

[a]Values are mean ± SEM of duplicate samples collected at each timepoint from two separate experiments.
[b]Average Formula Ia -concentration was determined using GraphPad Prism 8.1.2 from the total area under the curve from Formula Ia -TP concentrations detected by LC-MS at 0, 2, 8, 24, and 48 h; and divided by the total time of the assay (48 h).
[c]P value is determined using one-way ANOVA with Dunnett's multiple comparison analysis of Formula Ia + DMSO compared to various concentrations of CQ or HCQ using GraphPad Prism 8.1.2.

TABLE 4

Effect of CQ or HCQ on RDV-TP Formation in HEp-2 cells

| | Mean RDV-TP (pmol/million cells)[a] | | | | |
|---|---|---|---|---|---|
| Treatment time (h) | 1 μM Formula Ia | 1 μM Formula Ia + 1 μM CQ | 1 μM Formula Ia + 10 μMCQ | 1 μM Formula Ia + 1 μM HCQ | 1 μM Formula Ia + 10 μM HCQ |
| 2 | BLQ | BLQ | BLQ | BLQ | BLQ |
| 8 | 22.8 ± 1.4 | 7.7 ± 0.3 | 3.0 ± 0.5 | 5.8 ± 1.2 | 0.4 ± 0.3 |
| 24 | 40.8 ± 5.6 | 15.9 ± 2.0 | 6.2 ± 1.0 | 15.0 ± 3.2 | 3.9 ± 0.8 |
| 48 | 45.9 ± 5.6 | 20.7 ± 3.2 | 10.2 ± 2.0 | 20.0 ± 2.5 | 7.8 ± 0.6 |
| Average | 33.7 ± 4.4 | 13.6 ± 2.0 | 5.8 ± 1.2 | 12.6 ± 2.3 | 3.7 ± 0.6 |

TABLE 4-continued

Effect of CQ or HCQ on RDV-TP Formation in HEp-2 cells

| | Mean RDV-TP (pmol/million cells)[a] | | | | |
|---|---|---|---|---|---|
| Treatment time (h) | 1 µM Formula Ia | 1 µM Formula Ia + 1 µM CQ | 1 µM Formula Ia + 10 µMCQ | 1 µM Formula Ia + 1 µM HCQ | 1 µM Formula Ia + 10 µM HCQ |
| Formula Ia-TP concentration (pmol/million cells)[b] P value[c] | NA | 0.0002 | <0.0001 | <0.0001 | <0.0001 |

[a] Values are mean ± SEM of duplicate samples collected at each timepoint from two separate experiments.
[b] Average Formula Ia -TP concentration was determined using GraphPad Prism 8.1.2 from the total area under the curve from Formula Ia -TP concentrations detected by LC-MS at 0, 2, 8, 24, and 48 h; and divided by the total time of the assay (48 h).
[c] P value is determined using one-way ANOVA with Dunnett's multiple comparison analysis of Formula Ia + DMSO compared to various concentrations of CQ or HCQ using GraphPad Prism 8.1.2.

Example 3. SARS-CoV-2 Antiviral Data

Figure 4A:
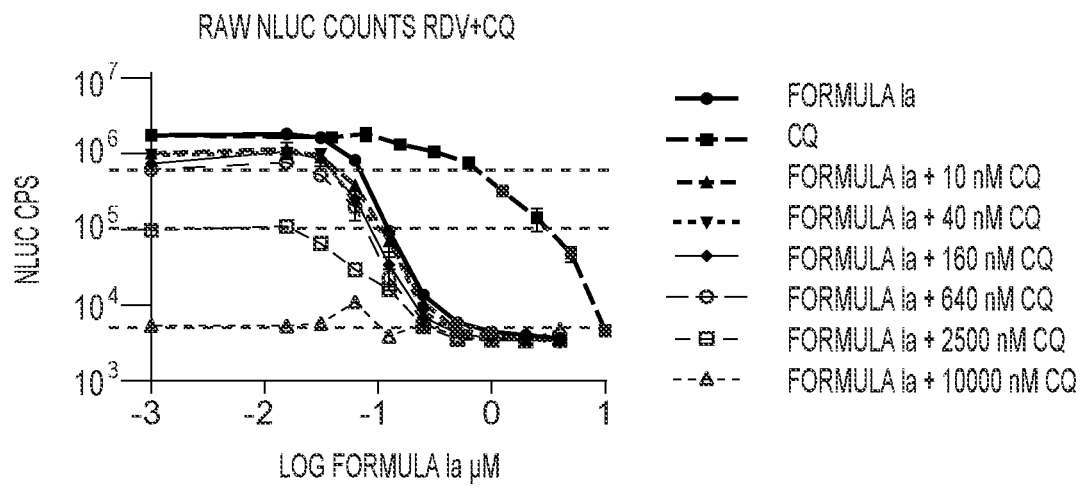
FIG. 4A. Shows SARS-CoV-2 antiviral data for the compound of Formula Ia in combination with CQ in A549-hACE2 cells.
Figure 4B:
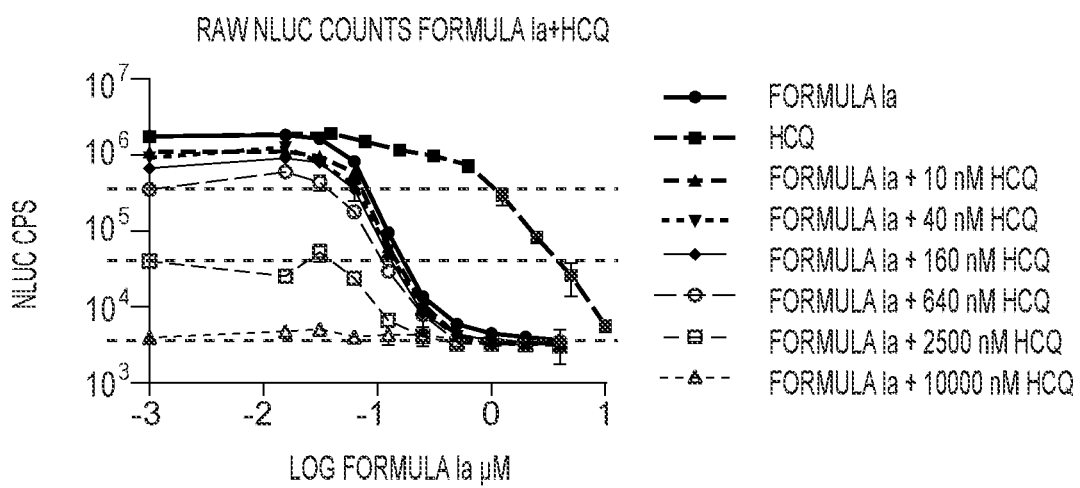
FIG. 4B. Shows SARS-CoV-2 antiviral data for the compound of Formula Ia in combination with HCQ in A549-hACE2 cells.

The anti-SARS-CoV-2 activities of the compound of Formula Ia and either CQ or HCQ were evaluated in A549-hACE2 transformed airway epithelial cells. The compound of Formula Ia, CQ, and HCQ individually exhibit potent in vitro antiviral activities against SARS-CoV-2, with $EC_{50}$ values of approximately 59.5 nM, 451 nM, and 365 nM, respectively (Table 5). The compound of Formula Ia $EC_{50}$ values were not observably different when combined with CQ or HCQ at concentrations up to 2.5 µM (Table 5); however, the overall Nluc signal in the assay decreased in the presence of CQ or HCQ in a dose-dependent manner (FIG. 4A and FIG. 4B). As shown in FIG. 4A, the Nluc signal at 0 µM Formula Ia (DMSO)+CQ corresponds to the Nluc signal at the specific CQ concentration in that treatment condition. The baseline Nluc signal of each Formula Ia titration curve is lowered to levels corresponding to the CQ concentration in that treatment condition. Similar effects are observed in the HCQ-treatment conditions FIG. 4B). At 10 µM of either CQ or HCQ alone, the Nluc signal was fully suppressed, indicating a complete inhibition of SARS-CoV-2 replication by either CQ or HCQ alone. Due to the potent antiviral activity of CQ and HCQ at the 10 µM concentration, a standard $EC_{50}$ value comparison is unable to reveal the potential decrease in Formula Ia activity against SARS-CoV-2 when combined with CQ or HCQ. Cytotoxicity was not observed at Formula Ia and HCQ combination concentrations analyzed (data not shown).

TABLE 5

SARS-CoV-2 Nluc EC50 values of RDV + CQ or HCQ in A549-hACE2 cells

| Treatment | $EC_{50}$ (nM)[b] |
|---|---|
| Formula Ia + DMSO | 59.5 |
| CQ + DMSO | 451 |
| HCQ + DMSO | 365 |
| Formula Ia + 10 nm CQ | 52.0 |
| Formula Ia + 40 nm CQ | 52.4 |
| Formula Ia + 160 nm CQ | 52.2 |
| Formula Ia + 640 nm CQ | 46.0 |
| Formula Ia + 2500 nm CQ | 39.8 |
| Formula Ia + 10000 nm CQ | ND[c] |
| Formula Ia + 10 nm HCQ | 63.6 |
| Formula Ia + 40 nm HCQ | 50.7 |
| Formula Ia + 160 nm HCQ | 60.0 |
| Formula Ia + 640 nm HCQ | 56.2 |
| Formula Ia + 2500 nm HCQ | 63.0 |
| Formula Ia + 10000 nm HCQ | ND[c] |

[a] n = 1
[b] $EC_{50}$ values were defined in GraphPad Prism 8.1.2 as the concentration at which there was a 50% decrease in the Nluc counts per second (CPS) relative to DMSO vehicle alone (0% virus inhibition) and uninfected control culture (100% virus inhibition).
[c] ND denotes where $EC_{50}$ values could not be calculated due to complete inhibition of Nluc signal by CQ or HCQ.

Although the foregoing disclosure has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A method of treating a viral infection in a human in need thereof, the method comprising administering to the human a therapeutically effective amount of a compound of Formula Ia, or a pharmaceutically acceptable salt thereof:

Formula Ia

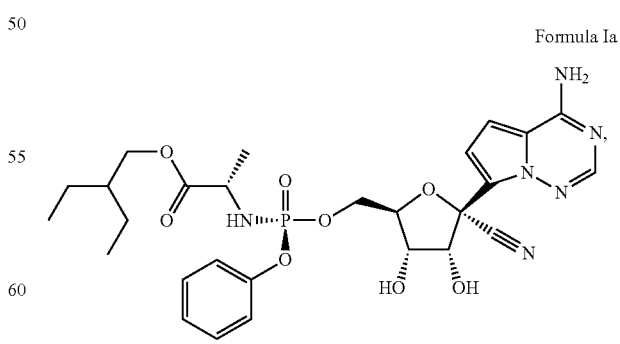

wherein the human is not being treated with chloroquine, or an analog or salt thereof, thereby treating the viral infection.

2. The method of claim 1, wherein the viral infection is caused by SARS-CoV-2.

3. The method of claim 1, wherein the compound of Formula Ia, or a pharmaceutically acceptable salt thereof is administered intravenously.

4. The method of claim 1, comprising administering to the human the therapeutically effective amount of the compound of Formula Ia:

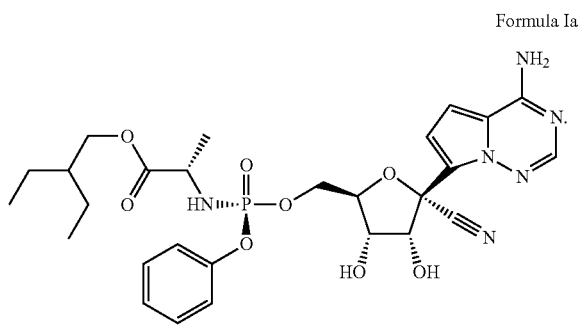 [SMILES: CCC(CC)COC(=O)[C@H](C)N[P@](=O)(OC[C@H]1O[C@@](C#N)(c2ccc3c(N)ncnn23)[C@H](O)[C@@H]1O)Oc1ccccc1]

Formula Ia

5. The method of claim 1, wherein the chloroquine, or an analog or salt thereof, is chloroquine, desethylchloroquine, hydroxychloroquine, desethylhydroxychloroquine, or bidesethylhydroxychloroquine, or a pharmaceutically acceptable salt thereof.

6. The method of claim 5, wherein the chloroquine, or an analog or salt thereof, is chloroquine, or a pharmaceutically acceptable salt thereof.

7. The method of claim 6, wherein the chloroquine, or an analog or salt thereof, is chloroquine phosphate.

8. The method of claim 5, wherein the chloroquine, or an analog or salt thereof, is hydroxychloroquine, or a pharmaceutically acceptable salt thereof.

9. The method of claim 8, wherein the chloroquine, or an analog or salt thereof, is hydroxychloroquine sulfate.

10. The method of claim 1, wherein the human weighs at least 40 kg, and the compound of Formula Ia, or a pharmaceutically acceptable salt thereof, is administered intravenously in the first dose of 200 mg on day 1, and administered intravenously in a second dose of 100 mg on each of the following 4 days.

11. The method of claim 10, wherein the second dose of 100 mg is administered for an additional 1 to 5 days.

12. The method of claim 10, wherein the human weighs at least 40 kg, and the compound of Formula Ia, or a pharmaceutically acceptable salt thereof, is administered intravenously in the first dose of 200 mg on day 1, and administered intravenously in a second dose of 100 mg on each of the following 9 days.

13. The method of claim 1, wherein the human weighs from 3.5 kg to less than 40 kg, and the compound of Formula Ia, or a pharmaceutically acceptable salt thereof, is administered intravenously in the first dose of 5 mg/kg on day 1, and administered intravenously in a second dose of 2.5 mg/kg on each of the following 4 days.

14. The method of claim 13, wherein the second dose of 2.5 mg/kg is administered for an additional 1 to 5 days.

15. The method of claim 13, wherein the human weighs from 3.5 kg to less than 40 kg, and the compound of Formula Ia, or a pharmaceutically acceptable salt thereof, is administered intravenously in the first dose of 5 mg/kg on day 1, and administered intravenously in a second dose of 2.5 mg/kg on each of the following 9 days.

16. The method of claim 1, wherein the compound of Formula Ia, or a pharmaceutically acceptable salt thereof, is administered intravenously over from about 30 to about 120 minutes.

17. The method of claim 1, wherein the human has not been administered chloroquine, or an analog or salt thereof, within 1 day of receiving a first dose of the compound of Formula Ia, or pharmaceutically acceptable salt thereof.

18. The method of claim 1, wherein the human has not been administered chloroquine, or an analog or salt thereof, within 10 days of receiving the first dose of the compound of Formula Ia, or pharmaceutically acceptable salt thereof.

19. The method of claim 1, wherein the human has not been administered chloroquine, or an analog or salt thereof, within 90 days of receiving the first dose of the compound of Formula Ia, or pharmaceutically acceptable salt thereof.

20. The method of claim 1, wherein the human has not been administered chloroquine, or an analog or salt thereof, within 365 days of receiving the first dose of the compound of Formula Ia, or pharmaceutically acceptable salt thereof.

21. The method of claim 1, wherein the human is not administered chloroquine, or an analog or salt thereof, during the treatment of the viral infection.

22. The method of claim 1, further comprising instructing the human not to take chloroquine, or an analog or salt thereof, during the treatment of the viral infection.

23. The method of claim 1, further comprising instructing the human to wait at least 10 days after taking chloroquine, or an analog or salt thereof, before administering the compound of Formula Ia, or pharmaceutically acceptable salt thereof.

24. The method of claim 1, wherein the human has a plasma or blood concentration of the chloroquine, or an analog or salt thereof, of less than 50 ng/mL at the time a first dose of the compound of Formula Ia, or pharmaceutically acceptable salt thereof, is administered to the human.

* * * * *

UNITED STATES PATENT AND TRADEMARK OFFICE
CERTIFICATE OF CORRECTION

PATENT NO. : 11,491,169 B2
APPLICATION NO. : 17/676920
DATED : November 8, 2022
INVENTOR(S) : Tomas Cihlar Page 1 of 1

It is certified that error appears in the above-identified patent and that said Letters Patent is hereby corrected as shown below:

In the Specification

Column 13, Lines 16-17, delete ""bidesethylhydroxychloroquine" and insert
-- bisdesethylhydroxychloroquine --;

Column 13, Lines 54-55, delete ""bidesethylhydroxychloroquine" and insert
-- bisdesethylhydroxychloroquine --;

In the Claims

Column 39, Lines 24-25, Claim 5, delete ""bidesethylhydroxychloroquine" and insert
-- bisdesethylhydroxychloroquine --.

Signed and Sealed this
Twenty-eighth Day of February, 2023

Katherine Kelly Vidal
*Director of the United States Patent and Trademark Office*